US012396981B2

(12) United States Patent
Shulman

(10) Patent No.: US 12,396,981 B2
(45) Date of Patent: Aug. 26, 2025

(54) METHODS OF USING DMT

(71) Applicant: William Shulman, Kentfield, CA (US)

(72) Inventor: William Shulman, Kentfield, CA (US)

( * ) Notice: Subject to any disclaimer, the term of this patent is extended or adjusted under 35 U.S.C. 154(b) by 0 days.

(21) Appl. No.: 18/601,926

(22) Filed: Mar. 11, 2024

(65) Prior Publication Data
US 2024/0299355 A1   Sep. 12, 2024

Related U.S. Application Data

(60) Provisional application No. 63/451,164, filed on Mar. 9, 2023.

(51) Int. Cl.
A61K 31/4045   (2006.01)
A61K 9/00        (2006.01)
A61K 31/135     (2006.01)
A61K 31/5513   (2006.01)

(52) U.S. Cl.
CPC ........ *A61K 31/4045* (2013.01); *A61K 9/0043* (2013.01); *A61K 31/135* (2013.01); *A61K 31/5513* (2013.01)

(58) Field of Classification Search
None
See application file for complete search history.

(56) References Cited

U.S. PATENT DOCUMENTS

| | | | |
|---|---|---|---|
| 6,107,499 | A  | 8/2000  | Shashoua |
| 6,258,836 | B1 | 7/2001  | Shashoua |
| 7,335,379 | B2 | 2/2008  | Carrara et al. |
| 9,708,315 | B2 | 7/2017  | Cid-Núñez et al. |
| 9,849,125 | B1 | 12/2017 | Yang et al. |
| 9,861,629 | B1 | 1/2018  | Hughey et al. |
| 10,071,095 | B2 | 9/2018 | Cid-Nunez et al. |
| 10,106,542 | B2 | 10/2018 | Alonso-De Diego et al. |
| 10,226,432 | B2 | 3/2019 | Teles et al. |
| 10,537,573 | B2 | 1/2020 | Klein et al. |
| 10,933,073 | B2 | 3/2021 | Chadeayne |
| 10,947,257 | B2 | 3/2021 | Londesbrough et al. |
| 11,071,729 | B2 | 7/2021 | Cid-Nunez et al. |
| 11,332,441 | B2 | 5/2022 | Chadeayne |
| 11,358,934 | B2 | 6/2022 | Chadeayne |
| 11,369,606 | B2 | 6/2022 | Klein et al. |
| 11,414,423 | B1 | 8/2022 | Olson et al. |
| 11,440,879 | B2 | 9/2022 | Kruegel |
| 11,471,439 | B2 | 10/2022 | Chadeayne |
| 11,478,449 | B1 | 10/2022 | Witowski et al. |
| 2008/0220441 | A1 | 9/2008 | Birnbaum et al. |
| 2011/0245215 | A1 | 10/2011 | Carrara et al. |
| 2015/0283087 | A1 | 10/2015 | Vamvakas et al. |
| 2018/0221396 | A1 | 8/2018 | Chadeayne |
| 2019/0142851 | A1 | 5/2019 | Chadeayne |
| 2019/0249173 | A1 | 8/2019 | Vargeese et al. |
| 2019/0380978 | A1 | 12/2019 | Rands et al. |
| 2020/0024535 | A1 | 1/2020 | Tusa et al. |
| 2020/0060997 | A1 | 2/2020 | Goren et al. |
| 2020/0157040 | A1 | 5/2020 | Pearson et al. |
| 2020/0278346 | A1 | 9/2020 | Zahler et al. |
| 2020/0368169 | A1 | 11/2020 | Gosangari et al. |
| 2021/0085671 | A1 | 3/2021 | Chadeayne |
| 2021/0113644 | A1 | 4/2021 | Chadeayne |
| 2021/0137854 | A1 | 5/2021 | Goren et al. |
| 2021/0145851 | A1 | 5/2021 | Stamets |
| 2021/0254056 | A1 | 8/2021 | Liu et al. |
| 2021/0292278 | A1 | 9/2021 | Chadeayne |
| 2021/0300870 | A1 | 9/2021 | Chadeayne |
| 2021/0346346 | A1 | 11/2021 | Chadeayne |
| 2021/0353615 | A1 | 11/2021 | Chadeayne |
| 2021/0361679 | A1 | 11/2021 | Chadeayne |
| 2022/0003741 | A1 | 1/2022 | Gibbs |
| 2022/0017550 | A1 | 1/2022 | Slassi et al. |
| 2022/0024956 | A1 | 1/2022 | Slassi et al. |
| 2022/0041540 | A1 | 2/2022 | Kruegel |
| 2022/0079881 | A1 | 3/2022 | Modi |
| 2022/0112162 | A1 | 4/2022 | Chadeayne |
| 2022/0125742 | A1 | 4/2022 | Kagan et al. |
| 2022/0273620 | A1 | 9/2022 | Chadeayne |
| 2022/0276234 | A1 | 9/2022 | Gibbs |

(Continued)

FOREIGN PATENT DOCUMENTS

| | | |
|---|---|---|
| EP | 2084519 A2 | 8/2009 |
| EP | 2560687 A2 | 2/2013 |

(Continued)

OTHER PUBLICATIONS

US 8,796,311 B2, 08/2014, Nunez-Cid (withdrawn)
Experience:2.5g Mushrooms + 500mg DMT Graphene https://psychonautwiki.org/wiki/Experience:2.5g_Mushrooms_%2B_500mg_DMT (Year: 2022).*
Structure-Activity Relationships for Psilocybin, Baeocystin, Aeruginascin, and Related Analogues to Produce PharmacologicalEffects in Mice Glatfelter et al. ACS Pharmacol. Transl. Sci. 2022, 5, 1181-1196 (Year: 2022).*
Administration of N, N-dimethyltryptamine (DMT) in psychedelic therapeutics and research and the study of endogenous DMT Barker et al. Psychopharmacology (2022) 239: 1749-1763 (Year: 2022).*
"Follow the Path You Have Chosen, Traveler": An Experience with DMT & Alprazolam (Xanax) (exp86874) Curiosityandthecat https://www.erowid.org/experiences/exp.php?ID=86874 (Year: 2010).*

(Continued)

*Primary Examiner* — Jeffrey S Lundgren
*Assistant Examiner* — Eric Tran
(74) *Attorney, Agent, or Firm* — CALYX LAW; Graham Pechenik; Kody Zalewski

(57) ABSTRACT

The present disclosure relates in some aspects to methods for modulating and improving the subjective experience of N,N-dimethyltryptamine (DMT) by administering DMT after a long-acting tryptamine such as psilacetin, and in some embodiments, together with a benzodiazepine and/or ketamine, or in some further embodiments, together with a second long-acting psychedelic. In some aspects, disclosed methods are useful for treating medical conditions, such as mental health disorders and neurodegenerative disorders. In some aspects, disclosed methods are useful for improving health and wellbeing, such as in healthy people.

28 Claims, No Drawings

(56) References Cited

U.S. PATENT DOCUMENTS

| | | | |
|---|---|---|---|
| 2022/0347185 | A1 | 11/2022 | Chadeayne |
| 2022/0363635 | A1 | 11/2022 | Chadeayne |

FOREIGN PATENT DOCUMENTS

| | | | |
|---|---|---|---|
| WO | 2006110642 | A2 | 10/2006 |
| WO | 2011050206 | A2 | 4/2011 |
| WO | 2013167743 | A1 | 11/2013 |
| WO | 2016111731 | A1 | 7/2016 |
| WO | 2018057576 | A1 | 3/2018 |
| WO | 2018104729 | A1 | 6/2018 |
| WO | 2018148605 | A1 | 8/2018 |
| WO | 2019058145 | A1 | 3/2019 |
| WO | 2019099745 | A1 | 5/2019 |
| WO | 2020023084 | A1 | 1/2020 |
| WO | 2020176597 | A1 | 9/2020 |
| WO | 2020181194 | A1 | 9/2020 |
| WO | 2020263941 | A1 | 12/2020 |
| WO | 2021016423 | A1 | 1/2021 |
| WO | 2021041407 | A1 | 3/2021 |
| WO | 2021076849 | A1 | 4/2021 |
| WO | 2021155468 | A1 | 8/2021 |
| WO | 2021173989 | A1 | 9/2021 |
| WO | 2021188782 | A1 | 9/2021 |
| WO | 2021188812 | A1 | 9/2021 |
| WO | 2021207137 | A1 | 10/2021 |
| WO | 2021209815 | A1 | 10/2021 |
| WO | 2021226041 | A1 | 11/2021 |
| WO | 2021236759 | A2 | 11/2021 |
| WO | 2021252692 | A1 | 12/2021 |
| WO | 2021255737 | A1 | 12/2021 |
| WO | 2022047256 | A1 | 3/2022 |
| WO | 2022072467 | A1 | 4/2022 |
| WO | 2022081549 | A1 | 4/2022 |
| WO | 2022082058 | A1 | 4/2022 |
| WO | 2022109050 | A1 | 5/2022 |
| WO | 2022115796 | A1 | 6/2022 |
| WO | 2022115798 | A2 | 6/2022 |
| WO | 2022120475 | A1 | 6/2022 |
| WO | 2022125616 | A1 | 6/2022 |
| WO | 2022132691 | A1 | 6/2022 |
| WO | 2022150530 | A1 | 7/2022 |
| WO | 2022150675 | A1 | 7/2022 |
| WO | 2022155284 | A1 | 7/2022 |
| WO | 2022173584 | A1 | 8/2022 |
| WO | 2022183287 | A1 | 9/2022 |
| WO | 2022212789 | A1 | 10/2022 |
| WO | 2022272176 | A1 | 12/2022 |

OTHER PUBLICATIONS

A Night Conversing with Elves: An Experience with 4-AcO-DMT & Ketamine (exp105657) Nov. 3 https://www.erowid.org/experiences/exp.php?ID=105657 (Year: 2016).*

Hierarchies of Hyperspace A Collection: An Experience with DMT (with 4-HO-MiPT, 4-AcO-DiPT, LSD, DPT, Ketamine, Methoxetamine, 5-MeO-DMT, Nitrous Oxide, & MDMA) (exp101485) Psychedaniellia https://www.erowid.org/experiences/exp.php?ID=101485 (Year: 2014).*

Ativan FDA Drug Label (Year: 2016).*

Literature Review: Neurological Mechanisms That Underlie the Therapeutic Potential of the Dissociative Compounds: Ketamine, Psilocybin, LSD, and DMT Sexauer The University of Arizona, Aug. 2021 (Year: 2021).*

Moss-Mason. Drugs on the internet: Mapping the terrain of engagement with darknet drug cryptomarkets in New Zealand. Open Access Te Herenga Waka-Victoria University of Wellington. Thesis. 2019.

Nichols De, Psychedelics, Pharmacological Reviews, 2016; 68(2):264-355.

Nichols De. Hallucinogens. Pharmacol Ther. 2004;101(2):131-181.

Nichols. Chemistry and Structure-Activity Relationships of Psychedelics. Curr Top Behav Neurosci. 2018;36:1-43.

Nowhereman. Reflections in the Obsidian Fountain: An Experience with 4-AcO-DMT, Ketamine & Psilocin (exp71909). Erowid.org. Jul. 8, 2008.

Palamar et al. Correlates of new psychoactive substance use among a self-selected sample of nightclub attendees in the United States. The American Journal on Addiction. 2016;25(5):400-407.

Pierlugi. Evaluating and Expanding Knowledge and Awareness of Health Professionals on the Consumption and Adverse Consequences of Novel Psychoactive Substances (NPS) Through Innovative Information Technologic Tools. University of Hertfordshire. 2015.

Ray Ts, Psychedelics and the Human Receptorome, PloS one, 2010; 5(2), e9019.

Rodrigues et al. Dimethyltryptamine: Endogenous Role and Therapeutic Potential. J Psychoactive Drugs. 2019;51(4):299-310.

Santos. Arfendazam User Guide (A Harm-Reduction Approach). Tripsitter. 2024.

Santos. Bretazenil: A Jumping-Off Point For New Social Psychoactive Drugs ?. Tripsitter. 2025.

Santos. Bromazepam 101: Safety, Risks, Dosage & More. Tripsitter. 2024.

Santos. Clobazam: Safety, Risks, Dosage & Harm Reduction. Tripsitter. 2024.

Santos. Clotiazepam (Clozan) Fact Sheet & Harm Reduction Guide. Tripsitter. 2024.

Santos. Demoxepam: Fact Sheet & Harm Reduction Guide. Tripsitter. 2024.

Santos. Desmethylflunitrazepam Fact Sheet & Harm Reduction Guide. Tripsitter. 2024.

Santos. Devazepide: An Atypical Benzodiazepine For Boosting Appetite. Tripsitter. (2024).

Santos. Diclazepam: Fact Sheet & Harm Reduction Guide. Tripsitter. 2024.

Santos. Etizolam (Etilaam) Fact Sheet & Harm Reduction Guide. Tripsitter. 2024.

Santos. Everything You Need To Know About Alprazolam (Xanax). Tripsitter. 2024.

Santos. Flubromazepam: Fact Sheet & Harm Reduction Guide. Tripsitter. 2024.

Santos. Flumazenil (Anexate): The Benzodiazepine Antidote. Tripsitter. 2024.

Santos. Haloxazolam Fact Sheet: Dosage, Safety, & Harm-Reduction Tips. Tripsitter. 2024.

Santos. Medazepam (Nobrium) Fact Sheet: Dosage, Safety, & Closest Alternatives. Tripsitter. 2024.

Santos. Prazepam (Centrax) Fact Sheet: Uses, Characteristics, & Risks. Tripsitter. 2024.

Shih et al. Role of Mao A and B in neurotransmitter metabolism and behavior. Pol J Pharmacol. 1999;51(1):25-29.

Shulgin & Shulgin. PiHKAL: A Chemical Love Story, 1992 Transform Press, Berkeley CA.

Shulgin & Shulgin. TiHKAL: The Continuation, 1997 Transform Press.

Simms. 7 Common LSD Myths & Misconceptions Debunked. Tripsitter. 2024.

Studerus et al. Psychometric Evaluation of the Altered States of Consciousness Rating Scale (OAV). PloS one, 2010; 5(8), e12412.

Szabo. Psychedelics and Immunomodulation: Novel Approaches and Therapeutic Opportunities. Front Immunol. 2015;6:358.

Timmermann et al. Effects of DMT on mental health outcomes in healthy volunteers. Scientific Reports. 2024; 14(1):3097.

Uporova. Northern Trends in Ecstasy and Related Drug Markets 2017: Findings from the Ecstasy and Related Drugs Reporting System (EDRS). Australian Drug Trends Series. 2017;197.

Vogt et al. Acute effects of intravenous DMT in a randomized placebo-controlled study in healthy participants. Transl Psychiatry. 2023;13(1):172.

Vollenweider & Kometer. The neurobiology of psychedelic drugs: implications for the treatment of mood disorders. Nat Rev Neurosci. 2010;11(9):642-651.

(56) References Cited

OTHER PUBLICATIONS

Walters. Brotizolam (Lendormin): Uses, Safety, & Harm Reduction Tips. Tripsitter. 2024.
White Powder ID: 12209. DrugsData.Org. 2022.
Yuen et al. Activation of 5-HT2A/C Receptors Counteracts 5-HT1A Regulation of N-Methyl-D-aspartate Receptor Channels in Pyramidal NeuronsofPrefrontal Cortex. Journal of Biological Chemistry. 2008;283(25):17194-17204.
Zhang & Hashimoto. An update on ketamine and its two enantiomers as rapid-acting antidepressants. Expert Rev Neurother. 2019;19(1):83-92. doi:10.1080/14737175.2019.1554434.
38th International Congress of the European Association of Poisons Centres and Clinical Toxicologists (EAPCCT) May 22-25, 2018, Bucharest, Romania. Clinical Toxicology. 2018;56(6):453-608.
Andersson et al. Psychoactive substances as a last resort—a qualitative study of self-treatment of migraine and cluster headaches. Harm Reduction Journal. 2017;14-60:1-10.
Armenta et al. Analysis of hazardous chemicals by "stand alone" drift tube ion mobility spectrometry: a review. Analytical Methods. 2020;12(9).
Backberg et al. Phencyclidine analog use in Sweden—intoxication cases involving 3-MeO-PCP and 4-MeO-PCP from the STRIDA project. Clinical Toxicology. 2015;53(9):856-864.
Barker SA. Administration of N,N-dimethyltryptamine (DMT) in psychedelic therapeutics and research and the study of endogenous DMT. Psychopharmacology (Berl). 2022;239(6):1749-1763.
Barrett et al. The Challenging Experience Questionnaire: Characterization of challenging experiences with psilocybin mushrooms. J Psychopharmacol. 2016;30(12):1279-1295.
Barrett et al. Validation of the revised Mystical Experience Questionnaire in experimental sessions with psilocybin. J Psychopharmacol. 2015;29(11):1182-1190.
Benschop et al. Why do people use new psychoactive substances? Development of a new measurement tool in six European countries. Jounral of Psychopharmacology. 2020;34(6):600-611.
Berge et al., Pharmaceutical Salts. J.Pharm. Sci., 1977;66:1-19.
Brito-Da-Costa et al. Toxicokinetics and Toxicodynamics of Ayahuasca Alkaloids N,N-Dimethyltryptamine (DMT), Harmine, Harmaline and Tetrahydroharmine: Clinical and Forensic Impact. Pharmaceuticals (Basel). 2020;13(11):334.
Cameron and Olson. Dark Classics in Chemical Neuroscience: N,N-Dimethyltryptamine (DMT). ACS Chem Neurosci. 2018;9(10):2344-2357.
Chou & Talalay. Quantitative analysis of dose-effect relationships: the combined effects of multiple drugs or enzyme inhibitors. Adv Enzyme Regul. 1984;22:27-55.
Christin N. AnEU-focused analysis of drug supply on the online anonymous marketplace ecosystem. Carnegie Mellon University. 2017.
Christin. An EU-focused analysis of drug supply on the AlphaBay marketplace. Carnegie Mellon University. 2017.
Cloos & Ferreira. Current use of benzodiazepines in anxiety disorders. Current Opinion in Psychiatry. 2009;22(1):90-95.
Czarny et al. Validation of a simple and quick method for determination of psychoactive substances, drugs and their metabolites from human blood by LC-MS/MS. Microchemical Journal. 2022;182:107922.
Dell'Osso & Lader. Do benzodiazepines still deserve a major role in the treatment of psychiatric disorders? A critical reappraisal. European Psychiatry. 2013;28(1):7-20.
Di Trana et al. Molecular Insights and Clinical Outcomes of Drugs of Abuse Adulteration: New Trends and New Psychoactive Substances. Int. J. Mol. Sci. 2022;23(23):14619.
Dominguez-Clave et al. Ayahuasca: Pharmacology, neuroscience and therapeutic potential. Brain Res Bull. 2016;126(Pt 1):89-101.
DoNotRepeat. Use a Scale: An Experience with 4-AcO-DMT & Benzodiazepines (exp110569). Erowid.org. Apr. 27, 2018.
Edinoff et al. Benzodiazepines: Uses, Dangers, and Clinical Considerations. Neurol Int. 2021;13(4):594-607.

Finberg & Tenne. Relationship between tyramine potentiation and selective inhibition of monoamine oxidase types A and B in the rat vas deferens. Br J Pharmacol. 1982;77(1):13-21.
Fontanilla et al. The hallucinogen N,N-dimethyltryptamine (DMT) is an endogenous sigma-1 receptor regulator. Science. 2009;323(5916):934-937.
Frecska et al. A possibly sigma-1 receptor mediated role of dimethyltryptamine in tissue protection, regeneration, and immunity. J Neural Transm (Vienna). 2013; 120(9):1295-1303.
Gonzalez Munoz-Caballero. Patrones de consumo de nuevas drogas de síntesis. Farmacología de la 2C-B. Universitat Autonoma de Barcelona. 2016.
Gorgan & Press. Pharmacokinetics. StatsPearls Publishing. (2024).
Gotvaldova et al. Extensive Collection of Psychotropic Mushrooms with Determination of Their Tryptamine Alkaloids. Int. J. Mol. Sci. 2022;23(22):14068.
Griffiths et al. Mystical-type experiences occasioned by psilocybin mediate the attribution of personal meaning and spiritual significance 14 months later. J Psychopharmacol. 2008;22(6):621-632.
Griffiths et al. Psilocybin-occasioned mystical-type experience in combination with meditation and other spiritual practices produces enduring positive changes in psychological functioning and in trait measures of prosocial attitudes and behaviors. J Psychopharmacol. 2018;32(1):49-69.
Grob CS & Grigsby J, Handbook of Medical Hallucinogens, 2021.
Halberstadt & Geyer. Multiple receptors contribute to the behavioral effects of indoleamine hallucinogens. Neuropharmacology. 2011;61(3):364-381.
Halberstadt et al. 5-HT(2A) and 5-HT(2C) receptors exert opposing effects on locomotor activity in mice. Neuropsychopharmacology. 2009;34(8):1958-1967.
Halberstadt et al. Behavioral Neurobiology of Psychedelic Drugs. Current Topics in Behavioral Neruoscience. 2018;36.
Holford & Sheiner. Understanding the dose-effect relationship: clinical application of pharmacokinetic-pharmacodynamic models. Clin Pharmacokinet. 1981;6(6):429-453.
Honderbrink et al. New psychoactive substances (NPS) in the Netherlands: occurrence in forensic drug samples, consumer drug samples and poisons center exposures between 2013 and 2017. Addiction. 2019;115(4):716-725.
Hood R. The Construction and Preliminary Validation of a Measure of Reported Mystical Experience. Journal for the Scientific Study of Religion. 1975;14(1):29-41.
Huang et al. Isobologram Analysis: A Comprehensive Review of Methodology and Current Research. Front Pharmacol. 2019;10:1222.
Ionescu et al. Ketamine-Associated Brain Changes: A Review of the Neuroimaging Literature. Harv Rev Psychiatry. 2018;26(6):320-339.
Jones et al. In vivo validation of psilacetin as a prodrug yielding modestly lower peripheral psilocin exposure than psilocybin. Front Psychiatry. 2024;14:1303365.
Keiser et al. Predicting new molecular targets for known drugs. Nature. 2009;462(7270):175-181.
Ko et al. Psychedelics, Mystical Experience, and Therapeutic Efficacy: A Systematic Review. Front Psychiatry. 2022;13:917199.
Liester & Prickett. Hypotheses regarding the mechanisms of ayahuasca in the treatment of addictions. J Psychoactive Drugs. 2012;44(3):200-208.
Ly et al. Psychedelics Promote Structural and Functional Neural Plasticity. Cell Rep. 2018;23(11):3170-3182.
MacLean et al. The American Psychiatric Publishing Textbook of Substance Abuse Treatment—Chapter 15—Hallucinogens and Club Drugs. 2021.
Mathai et al. The relationship between subjective effects induced by a single dose of ketamine and treatment response in patients with major depressive disorder: A systematic review. J Affect Disord. 2020;264:123-129.
McIntyre et al. A Fatality Related to Two Novel Hallucinogenic Compounds: 4-Methoxyphencyclidine and 4-Hydroxy-N-methyl-N-ethyltryptamine. Journal of Analytical Toxicology. 2015;39(9):751-755.

(56) References Cited

OTHER PUBLICATIONS

Melt Pharmaceuticals, Inc. Melt Pharmaceuticals' MELT-300 (Midazolam 3mg and Ketamine 50mg Sublingual Tablet) Achieves Primary Sedation Endpoint in Phase 2 Pivotal Efficacy and Safety Study. BioSpace. (2022).

Melt Pharmaceuticals. Melt Pharmaceuticals' MELT-300 (Midazolam 3mg and Ketamine 50mg Sublingual Tablet) Achieves Primary Sedation Endpoint in Phase 2 Pivotal Efficacy and Safety Study. (2022).

Moliner et al. Psychedelics promote plasticity by directly binding to BDNF receptor TrkBNat. Neurosci. 2023;26:1032-1041.

Moreira. Targeted, semitargeted and nontargeted screening for drugs in whole blood by UPLCTOF-MS with dataindependent acquisition (DIA). University of Copenhagen.

\* cited by examiner

METHODS OF USING DMT

CROSS-REFERENCE

This application claims the benefit of U.S. Provisional App No. 63/451,164, filed Mar. 9, 2023, incorporated by reference for all purposes as if fully set forth herein.

FIELD OF THE INVENTION

This disclosure relates in some aspects to methods for modulating and improving the subjective experience of N,N-dimethyltryptamine (DMT), through drug administration protocols with a long-acting tryptamine such as psilacetin, optionally together with other drugs.

BACKGROUND OF THE INVENTION

N,N-dimethyltryptamine (often just "dimethyltryptamine" or "DMT") is an endogenous agonist for the serotonin 2A ($5-HT_{2A}$) receptor, that is naturally-occurring in many species of plants, some of which have long been used for their psychoactive properties.

DMT was first synthesized by the Canadian chemist Richard Manske in 1931, but its responsibility for psychedelic effects was not recognized until 1956, when the Hungarian chemist and psychiatrist Stephen Szara extracted DMT from *Mimosa hostilis* and administered it to himself intramuscularly. Clinical research on the effects of DMT in humans has been ongoing since the work of Rick Strassman in the 1990s, and at present DMT (and related deuterated DMT derivatives) is being investigated for its therapeutic potential in mental health disorders such as major depressive disorder (MDD), treatment-resistant depression (TRD), generalized anxiety disorder (GAD), post-traumatic stress disorder (PTSD), and obsessive-compulsive disorder (OCD), as well as for its ability to treat other health conditions such as for stroke recovery and traumatic brain injury (TBI).

DMT is rapidly inactivated by monoamine oxidase (MAO) enzymes during first-pass metabolism, and is thus not orally active, although it may be rendered such by taking it together with an MAO inhibitor (e.g., with plant beta-carbolines, as in the brew ayahuasca), or when administered by a different route (Nichols. Pharmacol Rev. 2016:68(2); 264-355).

By far the most common route of administration for DMT is inhalation. The rapid onset of inhaled DMT is one of the defining characteristics of its psychedelic effects. Indeed, describing one of his experiences with inhaled DMT, the pioneering psychedelic chemist Alexander (Sasha) Shulgin wrote: "I was being destroyed—all that was familiar, all reference points, all identity—all viciously shattered in a few seconds. . . . I couldn't even mourn the loss—there was no one left to do the mourning. Up, up, out, out, eyes closed, I am at the speed of light, expanding, expanding, expanding, faster and faster until I have become so large that I no longer exist" (Shulgin & Shulgin, PiHKAL: A Chemical Love Story, Transform Press (1991)).

Despite being a hallmark of inhaled DMT, the rapidity and intensity of the onset of action can be disorienting and anxiety-producing. This may undermine the subjective DMT experience in some individuals, as well as under certain conditions, and may reduce or eliminate certain beneficial effects (as well as produce or increase certain negative effects).

A growing interest in using psychedelics to treat a variety of conditions, such as mental health and neuropsychiatric disorders, and for the betterment of the well, such as through improvements in creativity and wellbeing, as well as simply for the appreciation of psychedelic subjective effects and non-ordinary states of consciousness, has created an ongoing need for the development of improved methods for administering DMT.

Further, state-level legal changes may increasingly permit supervised "adult use" of psychedelics outside of a medical context. For example, in Oregon in 2020, and in Colorado in 2022, ballot measures were passed (as Proposition 109 and Proposition 122, respectively) to enact regulated-access regimes whereby healthy adults over 21 years old will be able to legally obtain and use certain psychedelics, under the supervision of a licensed facilitator, and in a licensed service center, and numerous other states appear poised to enact similar reforms.

There is therefore an increasing need for new methods of using psychedelics for improving health and wellbeing in healthy and unhealthy people alike. Methods which improve the DMT experience by reducing feelings of anxiety, enhancing feelings of control during the experience, and producing an overall improved positive subjective experience, will be highly sought in both clinical and regulated adult use contexts.

Provided herein are methods to meet these needs and others, and that have such advantages and improvements as will become readily apparent through the disclosure below.

INCORPORATION BY REFERENCE

Each cited patent, publication, and non-patent literature is hereby incorporated by reference in its entirety, as if each was incorporated by reference individually, and as if each is fully set forth herein. However, no such citation should be construed as an admission that a cited reference comes from an area that is analogous or directly applicable to the invention, nor should any citation be construed as an admission that a document or underlying information, in any jurisdiction, is prior art or forms part of the common general knowledge in the art.

BRIEF SUMMARY OF THE INVENTION

The following presents a simplified summary of some embodiments of the invention in order to provide a basic understanding of the invention. This summary is not an extensive overview of the invention. It is not intended to identify key or critical elements of the invention or to delineate the scope of the invention. Its sole purpose is to present some embodiments of the invention in a simplified form as a prelude to the more detailed description that is presented later.

In a first aspect, provided is a method of improving an individual's subjective experience of DMT, comprising administering to the individual: (i.) a long-acting tryptamine, or a pharmaceutically acceptable salt thereof; and (ii.) DMT, or a pharmaceutically acceptable salt thereof; wherein administering the long-acting tryptamine is prior to administering the DMT.

In some embodiments, the long-acting tryptamine is psilacetin, psilocybin, or psilocin.

In some embodiments, the long-acting tryptamine is psilacetin. In some embodiments, the psilacetin is administered at a dose of from about 5 to 50 mg, 10 to 40 mg, 15 to 30 mg, or 20 to 25 mg.

In some embodiments, the DMT is administered by inhalation. In some embodiments, the DMT is administered between 1 and 5 times during the 5 hours following administering to the individual the long-acting psychedelic. In some embodiments, each dose of DMT is from about 5 to 50 mg, 10 to 30 mg, or 15 to 25 mg.

In some embodiments, the method further comprises administering to the individual a benzodiazepine, or a pharmaceutically acceptable salt thereof. In some embodiments, the benzodiazepine is selected from the group consisting of alprazolam, bromazepam, chlordiazepoxide, clobazam, clonazepam, clorazepate, diazepam, estazolam, etizolam, flunitrazepam, flurazepam, flutoprazepam, halazepam, ketazolam, loprazolam, lorazepam, lormetazepam, midazolam, nimetazepam, nitrazepam, oxazepam, prazepam, quazepam, temazepam, tetrazepam, and triazolam.

In some embodiments, the benzodiazepine is lorazepam. In some embodiments, the lorazepam is administered at a dose of from about 0.5 to 2 mg.

In some embodiments, the method comprises administering the benzodiazepine prior to the long-acting tryptamine.

In some embodiments, the method further comprises administering to the individual ketamine, or a pharmaceutically acceptable salt thereof. In some embodiments, the ketamine is administered between 1 and 5 times during the 5 hours following administering to the individual the long-acting psychedelic. In some embodiments, each dose of ketamine is from about 5 to 50 mg, 10 to 30 mg, or 15 to 25 mg. In some embodiments, the ketamine is administered intranasally.

In some embodiments, the method further comprises administering to the individual a second long-acting psychedelic, or a pharmaceutically acceptable salt thereof. In embodiments, the second long-acting psychedelic is 4-hydroxy-N-methyl-N-ethyltryptamine (4-HO-MET) or 4-hydroxy-N-methyl-N-isopropyltryptamine (4-HO-MiPT).

In some embodiments, the individual's subjective experience of DMT is improved in at least one respect compared to the administration of an equal amount of DMT alone.

In some embodiments, the improvement in at least one respect comprises a decrease in a physical or psychological side effect of DMT. In some embodiments, the physical or psychological side effect of DMT is any of disorientation, acute anxiety, emotional distress, diarrhea, nausea, vomiting, elevated heart rate, elevated blood pressure, dizziness, agitation, and muscle incoordination.

In some embodiments, the improvement in at least one respect comprises an increase in a positive effect of DMT. In some embodiments, the positive effect of DMT is any of euphoria, positive mood, internal unity, external unity, transcendence of time and space, ineffability, paradoxicality, sacredness, and noetic quality.

In some embodiments, the improvement in at least one respect comprises an increase in the score of any of the Mystical, Positive Mood, Transcendence of Time and Space, and Ineffability subscales of the 30-item revised Mystical Experience Questionnaire (MEQ30).

In some embodiments, the improvement in at least one respect comprises a decrease in the score of any of the Fear, Grief, Physical Distress, Insanity, Isolation, Death, and Paranoia subscales of the Challenging Experience Questionnaire (CEQ).

In another aspect, provided is a method of improving an individual's subjective experience of DMT, comprising administering to the individual:
 i. psilacetin, or a pharmaceutically acceptable salt thereof;
 ii. DMT, or a pharmaceutically acceptable salt thereof;
 iii. lorazepam, or a pharmaceutically acceptable salt thereof; and
 iv. ketamine, or a pharmaceutically acceptable salt thereof;
wherein the psilacetin is administered prior to the DMT; and wherein the individual's subjective experience of DMT is improved in at least one respect compared to the administration of an equal amount of DMT alone.

Also provided is a kit, useful for the practice of disclosed methods, comprising:
 i. a long-acting tryptamine, or a pharmaceutically acceptable salt thereof;
 ii. DMT, or a pharmaceutically acceptable salt thereof; and
 iii. instructions for use.

In some embodiments, the kit comprises:
 i. psilacetin, or a pharmaceutically acceptable salt thereof;
 ii. DMT, or a pharmaceutically acceptable salt thereof;
 iii. lorazepam, or a pharmaceutically acceptable salt thereof;
 iv. ketamine, or a pharmaceutically acceptable salt thereof; and
 v. instructions for use.

The foregoing has outlined broadly and in summary certain pertinent features of the disclosure so that the detailed description of the invention that follows may be better understood, and so that the present contribution to the art can be more fully appreciated. Hence, this summary is to be considered as a brief and general synopsis of only some of the objects and embodiments disclosed herein, is provided solely for the benefit and convenience of the reader, and is not intended to limit in any manner the scope, or range of equivalents, to which the claims are lawfully entitled. Additional features of the invention are described hereinafter. It should be appreciated by those in the art that all disclosed specific compositions and methods are only exemplary, and may be readily utilized as a basis for modifying or designing other compositions and methods for carrying out the same purposes. Such equivalent compositions and methods will be appreciated to be also within the scope and spirit of the invention as set forth in the claims.

The headings within this document are being utilized only to expedite its review by a reader. They should not be construed as limiting the invention in any manner.

DETAILED DESCRIPTION OF THE INVENTION

While various aspects and features of certain embodiments are summarized above, the following detailed description illustrates several exemplary embodiments in further detail to enable one of skill in the art to practice such embodiments, and to make and use the full scope of the invention claimed. The described examples are provided for illustrative purposes and are not intended to limit the scope of the invention or its applications. It will be understood that many modifications, substitutions, changes, and variations in the described examples, embodiments, applications, and details of the invention illustrated herein can be made by those skilled in the art without departing from the spirit of the invention, or the scope of the invention as described in the appended claims.

The scope of the invention includes all embodiments and formulations thereof, not only those expressly described below, and it will be understood that many modifications, substitutions, changes, and variations in the described embodiments, applications, and details of the invention illustrated herein can be made by those skilled in the art without departing from the spirit of the invention, or the scope of the invention as set forth in the appended claims.

A. GENERAL DEFINITIONS AND TERMS

As used in this specification and the appended claims, the singular forms "a," "an," and "the" include plural referents unless the context clearly dictates otherwise. Thus, for example, reference to "an active agent" includes reference to a combination of two or more active agents, and reference to "an excipient" includes reference to a combination of two or more excipients. While the term "one or more" may be used, its absence (or its replacement by the singular) does not signify the singular only, but simply underscores the possibility of multiple agents or ingredients in particular embodiments.

The terms "comprising," "including," "such as," and "having" are intended to be inclusive and not exclusive (i.e., there may be other elements in addition to the recited elements). Thus, the term "including" as used herein means, and is used interchangeably with, the phrase "including but not limited to." The term "or" is used herein to mean, and is used interchangeably with, the term "and/or," unless context clearly indicates otherwise.

"Alkyl" will be understood to include straight or branched radicals having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" can also be used. Preferably, an alkyl group comprises from 1 to 10 carbon atoms, more preferably from 1 to 6 carbon atoms, more preferably from 1 to 4 carbon atoms, and most preferably from 1 to 3 carbon atoms. For any alkyl, the alkyl may be optionally substituted at one or more positions by deuterium, halogen, alkyl, alkyl ester, hydroxy, alkoxy, carboxy, formyl, aryl, cycloalkyl, heterocycloalkyl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate, $-OP(O)(OH)_2$, $-OC(O)H$, $-OSO_2OH$, $-OC(O)NH_2$, and $-SONH_2$.

A comprehensive list of the abbreviations utilized by organic chemists of ordinary skill in the art appears in the first issue of each volume of the Journal of Organic Chemistry; this list is typically presented in a table entitled Standard List of Abbreviations; the current list as of the date of this filing is hereby incorporated by reference as if fully set forth herein.

Unless otherwise indicated, all numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, "about" refers to plus or minus five percent (±5%) of the recited unit of measure. In some embodiments, "about" refers to plus or minus ten percent (±10%) of the recited unit of measure.

The term "substantially," where it is applied to modify a feature or limitation herein, will be read in the context of the invention and in light of the knowledge in the art to provide the appropriate certainty, e.g., by using a standard that is recognized in the art for measuring the meaning of "substantially" as a term of degree, or by ascertaining the scope as would one of skill in the art.

In some embodiments (equivalently, and simply as shorthand, "in embodiments"), the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments may contain certain errors necessarily resulting from the standard deviation found in their respective testing measurements.

Herein, "an effective amount" refers to an amount of active agent(s) that is non-toxic and sufficient to provide the desired effect with performance at a reasonable benefit/risk ratio attending any similar use of a like agent, such as a comparable psychedelic, or such as inhaled DMT alone. The effective amount will vary depending upon the subject and the effect sought, the manner of administration, and the like, all of which can readily be determined by one of skill.

Herein, "effect" or "efficacy" means the responses(s) in a mammal, and preferably a human, after administration by a disclosed combination or with a disclosed method that are judged to be desirable and beneficial. Hence, depending on the effect or improvement sought, and depending on the particular agent(s) in the disclosed combination or method, those responses may differ, but would be readily understood by those of skill.

Herein, "half-life" or "elimination half-life" refers to the amount of time it takes for the concentration of a substance to decrease to half of its starting dose in the body. For a majority of substances, drug elimination rates are proportional to plasma concentrations. Thus, elimination half-life is typically measured based on the change in plasma drug concentration with time (Hallare & Gerriets. Half Life. [Updated 2023 Jun. 20]. In: StatPearls [Internet]. Treasure Island (FL): StatPearls Publishing; 2024 January).

Herein, "administration period" refers to the period of time between the initial administration of a compound to a subject and its elimination from the subject's body as determined by the half-life of the compound administered. Approximately 93% of an administered compound is reached within four of that compound's half lives (Grogan & Preuss. Pharmacokinetics. [Updated 2023 Jul. 30]. In: StatPearls [Internet]. Treasure Island (FL): StatPearls Publishing; 2024 January). In some embodiments, "administration period" refers to the period of time between the initial administration of a compound and four of said compound's half lives. In some embodiments, "administration period" refers to the period of time between the initial administration of a first compound and the elimination (e.g., at least 93% elimination) of the final administered compound of a disclosed method.

In some embodiments, "administration period" is defined as the period in which the subjective effects of a compound are felt by a subject. Whether a subject is feeling one or more subjective effects of a compound (and what those one or more subjective effects are, as well as the intensity of those one or more subjective effects) can be determined by quantitative methods (e.g., measurement or estimation of serum concentration of the compound, evaluation with the Mystical Experience Questionnaire, the Challenging Experience Questionnaire, or the Hallucinogen Rating Scale), by qualitative methods (e.g., reports from the subject, interviewing the subject), or otherwise by someone of skill in the art, using the general knowledge in the art together with the teachings herein.

Generally, the nomenclature used and procedures performed herein are those known in fields relating to one or more aspects of the invention, such as biology, pharmacology, psychopharmacology, psychology, psychiatry, neuroscience, organic chemistry, synthetic chemistry, and/or medicinal chemistry, and are those that will be well known and commonly employed in such fields. Standard techniques and procedures will be those generally performed according to conventional methods in the art.

Unless defined otherwise, all technical and scientific terms herein have the meaning as commonly understood by one having ordinary skill in the art to which this invention belongs, who as a shorthand may be referred to simply as "one of skill."

Further definitions that may assist the reader in understanding the disclosed embodiments are as follows; however, it will be appreciated that such definitions are not intended to limit the scope of the invention, which shall be properly interpreted and understood by reference to the full specification (as well as any plain meaning known to one of skill in the relevant art) in view of the language used in the appended claims. The terminology used herein is for the purpose of describing particular embodiments only and is not intended to be limiting.

Still additional definitions and abbreviations are provided elsewhere herein.

B. COMPOUNDS a. Long-Acting Psychedelics

"Psychedelics" refers to a class of drugs which elicit certain cognitive, emotional, perceptual, physiological, psychological, and other effects. These effects may result in an altered or "non-ordinary" state of consciousness, which can include vivid visual and auditory perceptual changes, often accompanied by intense emotional, mystical, or "spiritual" experiences.

Psychedelic effects include effects on the mind, effects on mood, and visual effects. The duration of psychedelic effects experienced by an individual after consuming a psychedelic substance can vary depending on the type of substance, dose, as well as the genetic and physiological disposition of the subject.

"Long-acting psychedelics" refers in some embodiments to psychedelics with a duration of effects of at least 1 hour, 2 hours, 3 hours, 4 hours, 5 hours, 6 hours, 7 hours, 8 hours, 9 hours, 10 hours, 11 hours, or 12 hours. Measures of duration of effects may be known by reference to general knowledge in the art, or where not known in the art, may be determined by methods known by those of ordinary skill. For example, the duration of effects from a known dose of a known substance may be proportional to its elimination half life. In some embodiments, a "long-acting psychedelic" has an elimination half-life of at least 30 minutes, 1 hour, 2 hours, 3 hours, 4 hours, 5 hours, or 6 hours.

In some embodiments, the long-acting psychedelic has a duration of effects of between 1 and 4 hours. In some embodiments, the long-acting psychedelic is any of DPT, EPT, 4-AcO-DiPT, and 4-HO-DiPT.

In some embodiments, the long-acting psychedelic has a duration of effects of between 4 and 8 hours. In some embodiments, the long-acting psychedelic is any of psilocybin, ayahuasca, 1cP-MiPLA, LAE-32, MiPLA, PARGY-LAD, PRO-LAD, DET, DiPT, MiPT, 4-AcO-DET, 4-AcO-DMT (psilacetin), 4-AcO-MET, 4-AcO-MiPT, 4-HO-DET, 4-HO-DPT, 4-HO-EPT, 4-HO-MET, 4-HO-MiPT, 4-HO-MPT, 5-MeO-DALT, 5-MeO-DiPT, 5-MeO-MiPT, 4-HO-DMT (psilocin), 2C-B, 2C-C, 2C-D, 2C-T, 2, 5-DMA, and 2C-D.

In some embodiments, the long-acting psychedelic has a duration of effects of between 8 and 12 hours. In some embodiments, the long-acting psychedelic is any of LSD, 1B-LSD, mescaline, 1cP-AL-LAD, 1cP-LSD, 1P-ETH-LAD, 1P-LSD, 1V-LSD, AL-LAD, ALD-52 (1A-LSD), ETH-LAD, LSA, LSM-775, LSZ, allylescaline, escaline, mescaline, methallylescaline, proscaline, 2C-E, 2C-I, 2C-T-2, 2C-T-7, 2C-T-21, 2C-B-FLY, Bk-2C-B, B-MeO-2C-D (BOD), TMA-2, and TMA.

In some embodiments, the long-acting psychedelic has a duration of effects of greater than 12 hours. In some embodiments, the long-acting psychedelic is any of AMT, 5-MeO-aMT, ibogaine, 3C-E, 3C-P, 2C-P, DOB, DOC, DOI, DOM, and TMA-6.

In some embodiments, the long-acting psychedelic is a tryptamine. "Tryptamines" are as readily understood by those in the art, and include for example any substituted tryptamine having the structure below, wherein $R^{N1}$, $R^{N2}$, $R^{\alpha}$, $R^{\beta}$, $R^2$, $R^4$, $R^5$, $R^6$, and $R^7$ are as taught herein and as generally understood in the art:

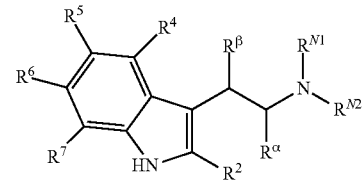

For example, in some embodiments, $R^{N1}$, $R^{N2}$, $R^{\alpha}$, $R^{\beta}$, $R^2$, $R^4$, $R^5$, $R^6$, and $R^7$ are independently hydrogen, deuterium, halogen, hydroxy, methoxy, phosphoryloxy, $C_1$-$C_5$ alkyl, $C_2$-$C_8$ alkenyl, $C_2$-$C_8$ alkynyl, $C_3$-$C_8$ cycloalkyl (independently or ring closed with the nitrogen), $C_3$-$C_8$ cycloalkenyl (independently or ring closed with the nitrogen), aryl, or heterocyclyl, any of which are optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate, —OP(O)(OH)$_2$, —OC(O)H, —OSO$_2$OH, —OC(O)NH$_2$, and —SONH. In some embodiments, such tryptamines are useful in the practice of disclosed methods, and include tryptamines which are long-acting psychedelics according to embodiments herein.

Other non-limiting examples of tryptamines, useful in the practice of disclosed methods, and including tryptamines which are long-acting psychedelics according to embodiments herein, include as examples N,N-dibutyltryptamine (DBT), N,N-diethyltryptamine (DET), N,N-diisopropyltryptamine (DiPT), 5-methoxy-α-methyltryptamine (α,O-DMS), 2,α-dimethyltryptamine (2,α-DMT), α,N-dimethyltryptamine (α,N-DMT), N,N-dipropyltryptamine (DPT), N-ethyl-N-isopropyltryptamine (EiPT), α-ethyltryptamine (AET), 3,4-dihydro-7-methoxy-1-methylcarboline (Harmaline), 7-methoxy-1-methylcarboline (Harmine), N,N-dibutyl-4-hydroxytryptamine (4-HO-DBT), N,N-diethyl-4-hydroxytryptamine (4-HO-DET), N,N-diisopropyl-4-hydroxytryptamine (4-HO-DiPT), N,N-dimethyl-4- hydroxytryptamine (4-HO-DMT), N,N-dipropyl-4-hydroxytryptamine (4-HO-DPT), N-ethyl-4-hydroxy-N-methyltryptamine (4-HO-MET), 4-hydroxy-N-isopropyl-N-methyltryptamine (4-HO-MiPT), 4-hydroxy-N-methyl-N-propyl-tryptamine (4-HO-MPT), 4-hydroxy-N,N-tetramethylenetryptamine (4-HO-pyr-T), 12-methoxyibogamine (Ibogaine), N-butyl-N-methyltryptamine (MBT), N,N-diisopropyl-4,5-methylenedioxytryptamine (4,5-MDO-DiPT), N,N-diisopropyl-5,6-methylenedioxytryptamine (5,6-MDO-DiPT), N,N-dimethyl-4,5-methylenedioxytryptamine (4,5-MDO-DMT), N,N-dimethyl-5,6-methylenedioxytryptamine (5,6-MDO-DMT), N-isopropyl-N-methyl-5,6-methylenedioxytryptamine (5,6-MDO-MiPT), N,N-diethyl-2-methyltryptamine (2-Me-DET), 2,N,N-trimethyltryptamine (2-Me-DMT), N-acetyl-5-methoxytryptamine (melatonin), N,N-diethyl-5-methoxytryptamine (5-MeO-DET), N,N-diisopropyl-5-methoxytryptamine (5-MeO-DiPT), N-isopropyl-4-methoxy-N-methyltryptamine (4-MeO-MiPT), N-isopropyl-5-methoxy-N-methyltryptamine (5-MeO-MiPT), 5,6-dimethoxy-N-isopropyl-N-methyltryptamine (5,6-MeO-MiPT), 5-methoxy-N-methyl-tryptamine (5-MeO-NMT), 5-methoxy-N,N-tetramethylenetryptamine (5-MeO-pyr-T), 6-methoxy-1-methyl-1,2,3,4-tetrahydrocarboline (6-MeO-THH), 5-methoxy-2,N,N-trimethyl-tryptamine (5-MeO-TMT), N,N-dimethyl-5-methylthiotryptamine (5-MeS-DMT), N-isopropyl-N-methyltryptamine (MiPT), α-methyltryptamine (α-MT), N-ethyltryptamine (NET), N-methyltryptamine (NMT), N,N-tetramethylenetryptamine (pyr-T), Tryptamine (T), 7-methoxy-1-methyl-1,2,3,4-tetrahydrocarboline (Tetrahydroharmine), and α,N-dimethyl-5-methoxytryptamine (α,N,O-TMS), as well as any pharmaceutically acceptable salt, hydrate, solvate, prodrug, stereoisomer, tautomer, analog, derivative, metabolite, variant, or isotopolog thereof, and combination of any of the foregoing thereof. See, e.g., Shulgin & Shulgin, TiHKAL: The Continuation, Transform Press (1997) ("TiHKAL"), which is incorporated by reference as if fully set forth herein.

In some embodiments, the tryptamine is not psilocybin or psilocin. In some embodiments, the tryptamine is not psilocybin. In some embodiments, the tryptamine is not psilocin. In some embodiments, the tryptamine is not a tryptamine found naturally occurring in *Psilocybe* or any other species of psychedelic or magic mushrooms.

In some embodiments, the tryptamine is a "complex tryptamine" or other indolamine and including such examples as ergolines, lysergamides, ergot alkaloids, iboga alkaloids such as ibogaine, and their analogs, derivatives, metabolites, variants, and isotopologs, as well as pharmaceutically acceptable salts, hydrates, solvates, prodrugs, stereoisomers, and tautomers thereof, and combinations of any of the foregoing thereof.

In some embodiments, the long-acting psychedelic is a lysergamide. "Lysergamides" are as readily understood by those in the art, and include for example any substituted lysergamide having the general structure below, wherein $R^1$, $R^2$, $R^3$, and $R^6$ are as taught herein and as generally understood in the art:

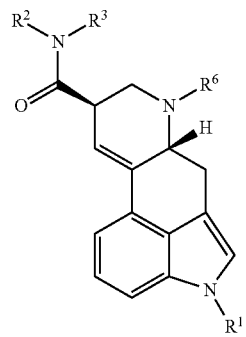

For example, in some embodiments, $R^1$, $R^2$, $R^3$, and $R^6$ are each independently hydrogen, deuterium, halogen, $C_1$-$C_5$ alkyl, $C_2$-$C_8$ alkenyl, $C_2$-$C_8$ alkynyl, or $C_3$-$C_8$ cycloalkyl; and any of which are optionally substituted at one or more positions by deuterium, halogen, alkyl, alkyl ester, hydroxy, alkoxy, carboxy, formyl, aryl, aryloxy, heterocyclyl, amino, alkylamino, arylamido, alkylamido, thiol, thioalkyl, thioaryl, alkylsulfonyl, alkylcarbamoyl, arylcarbamoyl, nitro, cyano, nitrate, —OP(O)(OH)$_2$, —OC(O)H, —OSO$_2$OH, —OC(O)NH$_2$, and —SONH. In some embodiments, such lysergamides are useful in the practice of disclosed methods, and include lysergamides which are long-acting psychedelics according to embodiments herein.

Other non-limiting examples of lysergamides, useful in the practice of disclosed methods, and including lysergamides which are long-acting psychedelics according to embodiments herein, include as examples lysergic acid diethylamide (i.e., LSD, LSD-25), 6-ethyl-6-nor-lysergic acid diethylamide (ETH-LAD), 6-propynyl-6-nor-lysergic acid diethylamide (PARGY-LAD), 6-allyl-6-nor-lysergic acid diethylamide (AL-LAD), 6-propyl-6-nor-lysergic acid diethylamide (PRO-LAD), 6-isopropyl-6-nor-lysergic acid diethylamide (IP-LAD), 6-cylopropyl-6-nor-lysergic acid diethylamide (CIP-LAD), 6-butyl-6-nor-lysergic acid diethylamide (BU-LAD), 6-(2-fluoroethyl)-6-nor-lysergic acid diethylamide (FLUOROETH-LAD), 1-acetyl-lysergic acid diethylamide (i.e., ALD, ALD-52, N-acetyl-LSD), 1-propionyl-lysergic acid diethylamide (1P-LSD), 1-butyryl-lysergic acid diethylamide (1B-LSD), 1-valeryl-lysergic acid diethylamide (1V-LSD), 1-(cyclopropylmethanoyl)-lysergic acid diethylamide (1 cP-LSD), 1-(1,2-dimethylcyclobutane-1-carbonyl)-lysergic acid diethylamide (1D-LSD), 1-propionyl-6-allyl-6-nor-lysergic acid diethylamide (1P-AL-LAD), 1-(cyclopropylmethanoyl)-6-allyl-6-nor-lysergic acid diethylamide (1cP-AL-LAD), 1-propionyl-6-ethyl-6-nor-lysergic acid diethylamide (1P-ETH-LAD), lysergic acid 2,4-dimethylazetidide (i.e., LA-SS-Az, LSZ), lysergic acid piperidide (LSD-Pip), and lysergic acid methylisopropyl amide (MIPLA), as well as any pharmaceutically acceptable salt, hydrate, solvate, prodrug, stereoisomer, tautomer, analog, derivative, metabolite, variant, or isotopolog thereof, and combination of any of the foregoing thereof.

Other tryptamines, complex tryptamines, and lysergamides useful in disclosed methods will be apparent to those of skill in the art in view of general references well-known in the art. See, e.g., TiHKAL; Nichols, D. E. Chemistry and Structure-Activity Relationship of Psychedelics. In: Halberstadt, A. L., Vollenweider, F. X., Nichols, D. E. (eds) Behavioral Neurobiology of Psychedelic Drugs. Current Topics in Behavioral Neurosciences, vol 36. Springer, Berlin, Heidelberg); Grob & Grigsby, Handbook of Medical Hallucinogens, 2021; Nichols, Pharmacological Reviews, 2016; 68(2), 264-355; and references cited therein.

In some embodiments, the lysergamide is not LSD.

In some embodiments, the long-acting tryptamine is a 4-hydroxytryptamine (e.g., psilocin). In some embodiments, the long-acting tryptamine is a 4-phosphoryloxytryptamine (e.g., psilocybin). In some embodiments, the long-acting tryptamine is a 4-acetoxytryptamine (e.g., psilacetin). In some embodiments, the long-acting tryptamine is psilocin or psilocybin, or a pharmaceutically acceptable salt thereof. In some embodiments, the long-acting tryptamine is psilocin, psilocybin, or psilacetin, or a pharmaceutically acceptable salt thereof.

In some embodiments, the long-acting psychedelic is a long-acting tryptamine having the structure of Formula (1):

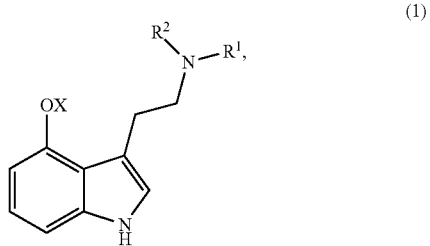

(1)

or a pharmaceutically acceptable salt thereof, wherein $R^1$ and $R^2$ are each independently H or alkyl; and X is H, $-PO_3H_2$, or $-C(O)$-alkyl.

In some embodiments, the long-acting psychedelic is selected from the group consisting of:
4-hydroxy-N,N-dimethyltryptamine (4-OH-DMT; psilocin),
4-phosphoryloxy-N,N-dimethyltryptamine (4-OPO$_3$H$_2$-DMT; psilocybin),
4-acetoxy-N,N-dimethyltryptamine (4-AcO-DMT; psilacetin),
N,N-diethyltryptamine (DET),
4-hydroxy-N,N-diethyltryptamine (4-HO-DET),
4-phosphoryloxy-N,N-diethyltryptamine (4-OPO$_3$H$_2$-DET),
4-acetoxy-N,N-diethyltryptamine (4-AcO-DET),
N,N-diisopropyltryptamine (DiPT),
4-hydroxy-N,N-diisopropyltryptamine (4-HO-DiPT),
4-phosphoryloxy-N,N-diisopropyltryptamine (4-OPO$_3$H$_2$-DiPT),
4-acetoxy-N,N-diisopropyltryptamine (4-AcO-DiPT),
5-methoxy-N,N-diisopropyltryptamine (5-MeO-DiPT),
N,N-dipropyltryptamine (DPT),
4-hydroxy-N,N-dipropyltryptamine (4-HO-DPT),
4-phosphoryloxy-N,N-dipropyltryptamine (4-OPO$_3$H$_2$-DPT),
4-acetoxy-N,N-dipropyltryptamine (4-AcO-DPT),
N,N-dibutyltryptamine (DBT),
4-hydroxy-N,N-dibutyltryptamine (4-HO-DBT),
4-phosphoryloxy-N,N-dibutyltryptamine (4-OPO$_3$H$_2$-DBT),
4-acetoxy-N,N-dibutyltryptamine (4-AcO-DBT),
4-hydroxy-N-methyl-N-ethyltryptamine (4-HO-MET),
4-phosphoryloxy-N-methyl-N-ethyltryptamine (4-OPO$_3$H$_2$-MET),
4-acetoxy-N-methyl-N-ethyltryptamine (4-AcO-MET),
N-methyl-N-isopropyltryptamine (MiPT),
4-hydroxy-N-methyl-N-isopropyltryptamine (4-HO-MiPT),
4-phosphoryloxy-N-methyl-N-isopropyltryptamine (4-OPO$_3$H$_2$-MiPT),
4-acetoxy-N-methyl-N-isopropyltryptamine (4-AcO-MiPT),
5-methoxy-N-methyl-N-isopropyltryptamine (5-MeO-MiPT),
4-hydroxy-N-methyl-N-propyltryptamine (4-HO-MPT),
4-phosphoryloxy-N-methyl-N-propyltryptamine (4-OPO$_3$H$_2$-MPT),
4-acetoxy-N-methyl-N-propyltryptamine (4-AcO-MPT),
5-methoxy-4-hydroxy-N,N-dimethyltryptamine (psilomethoxin), and
5-methoxy-N,N-diallyltryptamine (5-MeO-DALT);
and pharmaceutically acceptable salts thereof.

In some embodiments, the long-acting tryptamine is a 4-substituted tryptamine. In some embodiments, the 4-substituted tryptamine is a 4-hydroxytryptamine (e.g., psilocin). In some embodiments, the 4-substituted tryptamine is a 4-phosphoryloxytryptamine (e.g., psilocybin). In some embodiments, the 4-substituted tryptamine is a 4-acetoxytryptamine (e.g., psilacetin). In some embodiments, the 4-substituted tryptamine is psilocin or psilocybin, or a pharmaceutically acceptable salt thereof. In some embodiments, the 4-substituted tryptamine is psilocin, psilocybin, or psilacetin, or a pharmaceutically acceptable salt thereof.

In some embodiments, the long-acting tryptamine is a 4-substituted tryptamine selected from the group consisting of:
4-hydroxy-N,N-dimethyltryptamine (4-OH, DMT; psilocin),
4-phosphoryloxy-N,N-dimethyltryptamine (4-OPO$_3$H$_2$-DMT; psilocybin),
4-acetoxy-N,N-dimethyltryptamine (4-AcO-DMT; psilacetin),
4-hydroxy-N,N-diethyltryptamine (4-HO-DET),
4-phosphoryloxy-N,N-diethyltryptamine (4-OPO$_3$H$_2$-DET),
4-acetoxy-N,N-diethyltryptamine (4-AcO-DET),
4-hydroxy-N,N-diisopropyltryptamine (4-HO-DiPT),
4-phosphoryloxy-N,N-diisopropyltryptamine (4-OPO$_3$H$_2$-DiPT),
4-acetoxy-N,N-diisopropyltryptamine (4-AcO-DiPT),
4-hydroxy-N,N-dipropyltryptamine (4-HO-DPT),
4-phosphoryloxy-N,N-dipropyltryptamine (4-OPO$_3$H$_2$-DPT),
4-acetoxy-N,N-dipropyltryptamine (4-AcO-DPT),
4-hydroxy-N,N-dibutyltryptamine (4-HO-DBT),
4-phosphoryloxy-N,N-dibutyltryptamine (4-OPO$_3$H$_2$-DBT),
4-acetoxy-N,N-dibutyltryptamine (4-AcO-DBT),
4-hydroxy-N-methyl-N-ethyltryptamine (4-HO-MET),
4-phosphoryloxy-N-methyl-N-ethyltryptamine (4-OPO$_3$H$_2$-MET),
4-acetoxy-N-methyl-N-ethyltryptamine (4-AcO-MET),
4-hydroxy-N-methyl-N-isopropyltryptamine (4-HO-MiPT),
4-phosphoryloxy-N-methyl-N-isopropyltryptamine (4-OPO$_3$H$_2$-MiPT),
4-acetoxy-N-methyl-N-isopropyltryptamine (4-AcO-MiPT),
4-hydroxy-N-methyl-N-propyltryptamine (4-HO-MPT),
4-phosphoryloxy-N-methyl-N-propyltryptamine (4-OPO$_3$H$_2$-MPT), and
4-acetoxy-N-methyl-N-propyltryptamine (4-AcO-MPT);
and pharmaceutically acceptable salts thereof.

In some preferred embodiments, the long-acting tryptamine is psilacetin, or a pharmaceutically acceptable salt thereof. Psilacetin (4-AcO-DMT) is a synthetic analog of psilocybin and psilocin, the prodrug and active compound found in hallucinogenic species of the *Psilocybe* fungal genus. Psilacetin is known to produce similar subjective effects as psilocin with a comparable duration of 4-8 hours, likely due to psilacetin's conversion to psilocin in vivo (Jones et al. Front Psychiatry. 2024:14; 1303365). In some embodiments, the subjective effects of a disclosed method comprising psilacetin are improved compared to a method comprising psilocybin. In some embodiments, the subjective effects of a disclosed method comprising psilacetin are improved compared to a method comprising psilocin. In some embodiments, the subjective effects of a disclosed method comprising psilacetin are improved compared to a method comprising psilocybin and/or psilocin.

In some embodiments, the subjective effects of a disclosed method comprising psilacetin are improved compared to a different long-acting tryptamine. In some embodiments, the subjective effects of a disclosed method comprising psilacetin are improved compared to a different 4-substituted tryptamine. In some embodiments, the subjective effects of a disclosed method comprising psilacetin are improved compared to a 4-hydroxy (4-HO) tryptamine. In some embodiments, the subjective effects of a disclosed method comprising psilacetin are improved compared to a 4-phosphoryloxy (4-OPO$_3$H$_2$) tryptamine. In some embodiments, the subjective effects of a disclosed method comprising psilacetin are improved compared to a different 4-acetoxy (4-AcO) tryptamine.

In some embodiments, the subjective effects of a disclosed method comprising psilocybin are improved compared to a different long-acting tryptamine. In some embodiments, the subjective effects of a disclosed method comprising psilocybin are improved compared to a different 4-substituted tryptamine. In some embodiments, the subjective effects of a disclosed method comprising psilocybin are improved compared to a 4-hydroxy (4-HO) tryptamine. In some embodiments, the subjective effects of a disclosed method comprising psilocybin are improved compared to a different 4-phosphoryloxy (4-OPO$_3$H$_2$) tryptamine. In some embodiments, the subjective effects of a disclosed method comprising psilocybin are improved compared to a different 4-acetoxy (4-AcO) tryptamine.

In some embodiments, the subjective effects of a disclosed method comprising psilocin are improved compared to a different long-acting tryptamine. In some embodiments, the subjective effects of a disclosed method comprising psilocin are improved compared to a different 4-substituted tryptamine. In some embodiments, the subjective effects of a disclosed method comprising psilocin are improved compared to a different 4-hydroxy (4-HO) tryptamine. In some embodiments, the subjective effects of a disclosed method comprising psilocin are improved compared to a 4-phosphoryloxy (4-OPO$_3$H$_2$) tryptamine. In some embodiments, the subjective effects of a disclosed method comprising psilocin are improved compared to a 4-acetoxy (4-AcO) tryptamine.

In some embodiments, the long-acting tryptamine is a 4-acetoxy (4-AcO) tryptamine. In some embodiments, the long-acting tryptamine is a 4-hydroxy (4-HO) tryptamine. In some embodiments, the long-acting tryptamine is a 4-phosphoryloxy (4-OPO$_3$H$_2$) tryptamine.

In some embodiments, the long-acting tryptamine is psilocybin and/or psilocin. In some embodiments, the psilocybin and/or psilocin is administered in the form of a psilocybin-producing fungus, or an extract thereof, such as a liquid extract or a powdered extract.

Methods of producing extracts of a psilocybin-producing fungus will be well known to those of ordinary skill, and include extracts using a variety of solvents, such as aqueous extracts, alcohol extracts (e.g., ethanol, methanol), extracts in an acidified solvent, extracts in a basified solvent, and mixtures thereof. Extracts can be standardized (e.g., by alkaloid content).

A "psilocybin-producing" fungus (or psilocybin-producing fungi) is any fungus that produces or is capable of producing psilocybin. Over 100 species in the *Psilocybe* genus of fungi produce psilocybin. Psilocybin-producing species also can be found in a number of other genera, including *Athelia, Conocybe, Copelandia, Fibularhizoctonia, Galerina, Gymnopilus, Inocybe, Mycena, Panaeolus, Pholiotina*, and *Pluteus*. In some embodiments, the psilocybin-producing species is from any of these genera. In embodiments, the psilocybin-producing species is from any of the genera *Copelandia, Galerina, Gymnopilus, Inocybe, Panaeolus, Pholiotina, Pluteus*, and *Psilocybe*. In embodiments, it is from *Psilocybe*. Different species of psilocybin mushrooms, and different strains thereof, will be readily known or readily identifiable to those in the art.

In some embodiments, the psilocybin-producing fungus is a *Psilocybe* spp. fungus. In some embodiments, the *Psilocybe* spp. fungus is any of a *P. acutipilea, P. allenii, P. alutacea, P. angulospora, P. antioquiensis, P. araucariicola, P. atlantis, P. aquamarina, P. armandii (mexicana), P. aucklandiae, P. aztecorum, P. azurescens, P. baeocystis, P. banderillensis, P. bispora, P. brasiliensis, P. brunneocystidiata, P. caeruleoannulata, P. caerulescens, P. caerulipes, P. callosa, P. carbonaria, P. caribaea, P. chuxiongensis, P. collybioides, P. columbiana, P. congolensis, P. cordispora, P. cubensis, P. cyanescens, P. cyanofibrillosa, P. dumontii, P. egonii, P. eximia, P. fagicola, P. farinacea, P. fimetaria, P. fuliginosa, P. furtadoana, P. galindoi, P. gallaeciae, P. graveolens, P. guatapensis, P. heimii, P. herrerae, P. hispanica, P. hoogshagenii, P. inconspicua, P. indica, P. isabelae, P. jacobsii, P. jaliscana, P. kumaenorum, P. laurae, P. lazoi, P. liniformans, P. mexicana, P. mairei, P. makarorae, P. mammillata, P. medullosa, P. meridensis, P. meridionalis, P. mescaleroensis, P. moseri, P. muliercula, P. naematoliformis, P. natalensis, P. natarajanii, P. neorhombispora, P. neoxalapensis, P. ovoideocystidiata, P. papuana, P. paulensis, P. pelliculosa, P. pintonii, P. pleurocystidiosa, P. plutonia, P. portoricensis, P. pseudoaztecorum, P. puberula, P. quebecensis, P. rickii, P. rostrate, P. rzedowskii, P. samuiensis, P. schultesii, P. semilanceata, P. septentrionalis, P. serbica, P. sierrae, P. sylvatica, P. singer, P. strictipes, P. stuntzii, P. subacutipilea, P. subaeruginascens, P. subaeruginosa, P. subcaerulipes, P. subcubensis, P. subpsilocybioides, P. subtropicalis, P. tampanensis, P. thaicordispora, P. thaiaerugineomaculans, P. thaiduplicatocystidiata, P. uruguayensis, P. uxpanapensis, P. venenata, P. villarrealiae, P. weilii, P. weldenii, P. weraroa, P. wrightii, P. yungensis, P. zapotecoantillarum, P. zapotecocaribaea*, or *P. zapotecorum* species, including strains thereof.

Other psilocybin-producing fungi, not of the *Psilocybe* genus, will be readily known to those in the art. Non-limiting examples include *Conocybe siligineoides, Conocybe velutipes, Copelandia tropica, Inocybe aeruginascens, Inocybe caerulata, Inocybe coelestium, Inocybe corydalina, Inocybe haemacta, Inocybe tricolor, Galerina steglichii, Gymnopilus aeruginosus, Gymnopilus braendlei, Gymnopilus cyanopalmicola, Gymnopilus dilepis, Gymnopilus dunensis, Gymnopilus intermedius, Gymnopilus lateritius, Gymnopilus luteofolius, Gymnopilus luteoviridis, Gymnopilus luteus, Gymnopilus palmicola, Gymnopilus purpuratus, Gymnopilus subpurpuratus, Gymnopilus subspectabilis, Gymnopilus validipes, Gymnopilus viridans, Panaeolus venezolanus, Panaeolus tropicalis, Panaeolus tirunelveliensis, Panaeolus*

*rubricaulis, Panaeolus olivaceus, Panaeolus moellerianus, Panaeolus microsporus, Panaeolus lentisporus, Panaeolus fimicola, Panaeolus cyanescens, Panaeolus cinctulus, Panaeolus chlorocystis, Panaeolus cambodginiensis, Panaeolus bisporus, Panaeolus axfordii, Panaeolus africanus, Panaeolus affinis, Pholiotina cyanopus, Pholiotina smithii, Pluteus albostipitatus, Pluteus americanus, Pluteus cyanopus, Pluteus glaucus, Pluteus glaucotinctus, Pluteus nigroviridis, Pluteus phaeocyanopus, Pluteus salicinus, Pluteus saupei, Pluteus velutinornatus,* and *Pluteus villosus.*

Average concentrations of psilocybin and psilocin in psilocybin-producing fungi have been characterized (see, e.g., Gotvaldová et al. Int J Mol Sci. 2022; 23(22):14068; Stamets P. Psilocybin Mushrooms of the World: An Identification Guide. Ten Speed Press; 1996), from which a quantity of psilocybin and/or psilocin can be determined for a selected species or strain of psilocybin-producing fungus, reliably enough for use in certain disclosed embodiments. Additionally, the quantity of psilocybin and/or psilocin can be readily determined in fungal biomaterial or extracts thereof by standard techniques known to one of skill, such as by high-performance liquid chromatography (HPLC), or by using a rapid personal quantification means for determination of psilocybin concentration, one example of which is the PSILO-QTest (Miraculix; Jena, Germany), which uses a chemical color reaction to detect the concentration of psilocybin, with color intensity proportional to the concentration.

In some embodiments, a disclosed method comprises administering the long-acting tryptamine, or a pharmaceutically acceptable salt thereof, in a dose of between about 0.02 mg/kg and 0.20 mg/kg, 0.03 mg/kg and 0.13 mg/kg, 0.03 mg/kg and 0.07 mg/kg, 0.05 mg/kg and 0.10 mg/kg, or about 0.08 mg/kg. In some embodiments, the dose of the long-acting tryptamine is between about 0.02 mg/kg and 0.20 mg/kg. In some embodiments, the dose of the long-acting tryptamine is between about 0.03 mg/kg and 0.13 mg/kg. In some embodiments, the dose of the long-acting tryptamine is between about 0.03 mg/kg and 0.07 mg/kg. In some embodiments, the dose of the long-acting tryptamine is between about 0.05 mg/kg and 0.10 mg/kg. In some embodiments, the dose of the long-acting tryptamine is about 0.08 mg/kg. In some embodiments, the dose of the long-acting tryptamine is about 0.05 mg/kg. In some embodiments, the dose of the long-acting tryptamine, or a pharmaceutically acceptable salt thereof, is from about 0.1 to 1.0 mg/kg, 0.2 to 0.7 mg/kg, 0.2 to 0.5 mg/kg, or 0.3 to 0.4 mg/kg.

In some embodiments, a disclosed method comprises administering the long-acting tryptamine, or a pharmaceutically acceptable salt thereof, in a dose of between about 0.20 mg/kg and 1.0 mg/kg, 0.20 mg/kg and 0.80 mg/kg, 0.20 mg/kg and 0.60 mg/kg, 0.30 mg/kg and 0.80 mg/kg, or 0.30 mg/kg and 0.60 mg/kg. In some embodiments, the dose of the long-acting tryptamine is between about 0.20 mg/kg and 1.0 mg/kg. In some embodiments, the dose of the long-acting tryptamine is between about 0.20 mg/kg and 0.80 mg/kg. In some embodiments, the dose of the long-acting tryptamine is between about 0.20 mg/kg and 0.60 mg/kg. In some embodiments, the dose of the long-acting tryptamine is between about 0.30 mg/kg and 0.80 mg/kg. In some embodiments, the dose of the long-acting tryptamine is between about 0.30 mg/kg and 0.60 mg/kg.

In some embodiments, a disclosed method comprises administering long-acting tryptamine, or a pharmaceutically acceptable salt thereof, in a dose of between about 15 mg and 300 mg, 25 mg and 200 mg, 20 mg and 50 mg, or 50 mg and 100 mg, as well as ranges between these values. In some embodiments, the dose of the long-acting tryptamine is between about 15 mg and 300 mg. In some embodiments, the dose of the long-acting tryptamine is between about 25 mg and 200 mg. In some preferred embodiments, the dose of the long-acting tryptamine is between about 20 mg and 50 mg. In some embodiments, the dose of the long-acting tryptamine is between about 50 mg and 100 mg. In some embodiments, the dose of the long-acting tryptamine is about 5 to 50 mg, 10 to 40 mg, 15 to 30 mg, or 20 to 25 mg. In some embodiments, the dose of the long-acting tryptamine is about 5 to 50 mg. In some embodiments, the dose of the long-acting tryptamine is about 10 to 40 mg. In some embodiments, the dose of the long-acting tryptamine is about 15 to 30 mg. In some embodiments, the dose of the long-acting tryptamine is about 20 to 25 mg. In some embodiments, the dose of the long-acting tryptamine is about 5 mg. In some embodiments, the dose of the long-acting tryptamine is about 10 mg. In some embodiments, the dose of the long-acting tryptamine is about 15 mg. In some embodiments, the dose of the long-acting tryptamine is about 20 mg. In some embodiments, the dose of the long-acting tryptamine is about 25 mg. In some embodiments, the dose of the long-acting tryptamine is about 30 mg. In some embodiments, the dose of the long-acting tryptamine is about 40 mg. In some embodiments, the dose of the long-acting tryptamine is about 50 mg. In some embodiments, the dose of the long-acting tryptamine is about 75 mg. In some embodiments, the dose of the long-acting tryptamine is about 100 mg.

In some embodiments, a disclosed method comprises administering long-acting tryptamine, or a pharmaceutically acceptable salt thereof, in a dose (in a microgram dosage amount calculated based on the kilogram weight of the patient), of about 0.25 µg/kg or less (including a dose of 0.10 µg/kg or less, 0.05 µg/kg or less, and 0.01 µg/kg or less), at least 0.50 µg/kg, at least 0.55 µg/kg, at least 0.60 µg/kg, at least 0.65 µg/kg, at least 0.70 µg/kg, at least 0.75 µg/kg, at least 0.80 µg/kg, at least 0.85 µg/kg, at least 0.90 µg/kg, at least 0.95 µg/kg, at least 1.0 µg/kg, at least 1.1 µg/kg, at least 1.2 µg/kg, at least 1.3 µg/kg, at least 1.4 µg/kg, at least 1.5 µg/kg, at least 1.6 µg/kg, at least 1.7 µg/kg, at least 1.8 µg/kg, at least 1.9 µg/kg, at least 2.0 µg/kg, at least 2.1 µg/kg, at least 2.2 µg/kg, at least 2.3 µg/kg, at least 2.4 µg/kg, at least 2.5 µg/kg, at least 2.6 µg/kg, at least 2.7 µg/kg, at least 2.8 µg/kg, at least 2.9 µg/kg, or at least 3.0 µg/kg, as well as amounts within these ranges.

In some embodiments, a disclosed method comprises administering long-acting tryptamine, or a pharmaceutically acceptable salt thereof, in a dose of between about 0.01 µg/kg and 0.1 µg/kg, such as about 0.01 µg/kg, about 0.02 µg/kg, about 0.03 µg/kg, about 0.04 µg/kg, about 0.05 µg/kg, about 0.06 µg/kg, about 0.07 µg/kg about 0.08 µg/kg about 0.09 µg/kg, and about 0.1 µg/kg, as well as ranges between these values. In some embodiments, a single dose is between about 0.1 µg/kg and 3.0 µg/kg, such as about 0.1 µg/kg, about 0.2 µg/kg, about 0.3 µg/kg, about 0.4 µg/kg, about 0.5 µg/kg, about 0.6 µg/kg, about 0.7 µg/kg about 0.8 µg/kg about 0.9 µg/kg, about 1.0 µg/kg, about 1.2 µg/kg, about 1.4 µg/kg, about 1.6 µg/kg, about 1.8 µg/kg, about 2.0 µg/kg, about 2.2 µg/kg, about 2.4 µg/kg, about 2.6 µg/kg, about 2.8 µg/kg, about 3.0 µg/kg, as well as ranges between these values.

In some embodiments, a disclosed method comprises administering long-acting tryptamine, or a pharmaceutically acceptable salt thereof, in a dose of about 25 µg or less (including a dose of 10 µg or less, 5 µg or less, and 1 µg or less), from about 25 to 100 μg, 25 to 1000 μg, 50 to 100 μg, 50 to 250 μg, 50 to 1000 μg, 100 to 200 μg, 100 to 250 μg, 100 to 300 μg, 200 to 300 μg, 200 to 500 μg, 300 to 1000 μg, 400 to 1000 μg, 500 to 1000 μg, or greater than 1000 μg, as well as ranges between these values.

In some embodiments, the long-acting tryptamine is administered sublingually, buccally, orally, intramuscularly, or intravenously. In some embodiments, the long-acting tryptamine is administered orally. In some embodiments, the long-acting tryptamine is provided to an individual for oral consumption in the form of a fungus (e.g., a raw mushroom or dried mushroom; e.g., in embodiments wherein the long-acting tryptamine is psilocybin and/or psilocin). In some embodiments, the long-acting tryptamine is consumed orally in the form of a capsule, tablet, confectionery product (e.g., an infused chocolate or gummy, such as a psilacetin-infused chocolate or gummy). In some embodiments, the long-acting tryptamine is consumed orally in the form of an extract, such as an aqueous extract (e.g., a tea or other beverage form) or alcoholic extract (e.g., a tincture) of a fungus (e.g., in embodiments wherein the long-acting tryptamine is psilocybin and/or psilocin).

In some embodiments, a disclosed method comprises administering a combination of any two or more long-acting tryptamines. In some embodiments, a disclosed method comprises administering a combination of a long-acting tryptamine with another long-acting psychedelic. In some embodiments, a disclosed method comprises administering a combination comprising psilacetin and another long-acting psychedelic. In some embodiments, a disclosed method comprises administering a combination comprising psilacetin and another long-acting tryptamine. In some embodiments, a disclosed method comprises administering a combination comprising psilocybin and/or psilocin and another long-acting psychedelic. In some embodiments, a disclosed method comprises administering a combination comprising psilocybin and/or psilocin and another long-acting tryptamine.

For example, in some embodiments, a disclosed method comprises administering a combination comprising psilacetin and a 4-substituted tryptamine, such as selected from the group disclosed herein. In some embodiments, a disclosed method comprises administering a combination comprising psilacetin and a 4-acetoxy tryptamine, such as selected from the group disclosed herein. In some embodiments, a disclosed method comprises administering a combination comprising psilacetin and a 4-phosphoryloxy tryptamine, such as selected from the group disclosed herein. In some embodiments, a disclosed method comprises administering a combination comprising psilacetin and psilocybin. In some embodiments, a disclosed method comprises administering a combination comprising psilacetin and a 4-hydroxy tryptamine, such as selected from the group disclosed herein. In some embodiments, a disclosed method comprises administering a combination comprising psilacetin and psilocybin and/or psilocin. In some embodiments, a disclosed method comprises administering a combination comprising psilacetin and 4-HO-MiPT. In some embodiments, a disclosed method comprises administering a combination comprising psilacetin and 4-HO-MET.

In some embodiments, a disclosed method comprises administering a combination comprising psilocybin and/or psilocin and a 4-substituted tryptamine, such as selected from the group disclosed herein. In some embodiments, a disclosed method comprises administering a combination comprising psilocybin and/or psilocin and a 4-acetoxy tryptamine, such as selected from the group disclosed herein. In some embodiments, a disclosed method comprises administering a combination comprising psilocybin and/or psilocin and a 4-phosphoryloxy tryptamine, such as selected from the group disclosed herein. In some embodiments, a disclosed method comprises administering a combination comprising psilocybin and/or psilocin and 4-HO-MiPT. In some embodiments, a disclosed method comprises administering a combination comprising psilocybin and/or psilocin and 4-HO-MET.

b. Dimethyltryptamine (DMT)

In some embodiments, disclosed methods comprise administering dimethyltryptamine (N,N-dimethyltryptamine, DMT), or pharmaceutically acceptable salt thereof, to an individual that has been administered a long-acting tryptamine.

DMT is a psychoactive substituted tryptamine and a structural analog of tryptamine. It occurs naturally in a range of plants and animals, occurring notably in plants native to South and Central America such as *Psychotria viridis, Mimosa tenuiflora,* and *Diplopterys cabrerana* (Domínguez-Clavé et al. Brain Research Bulletin. 2016:126(1); 89-101).

DMT may be represented by the structure as follows:

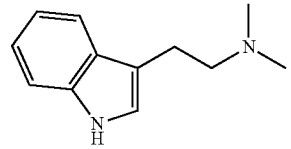

In some embodiments, a disclosed method comprises administering DMT freebase. In some embodiments, a disclosed method comprises administering a pharmaceutically acceptable salt of DMT. In some embodiments, a disclosed method comprises administering DMT fumarate.

In some embodiments, a disclosed method comprises administering a deuterated DMT. A "deuterated DMT" includes any compound having the structure of DMT, wherein at least one hydrogen, at any position, is replaced by a deuterium. In some embodiments, a disclosed method comprises administering a deuterated DMT in place of administering DMT.

DMT is principally administered intravenously (IV), intramuscularly (IM), or by inhalation (generally, by different methods of vaporization). DMT also can be administered by other means that avoid first-pass metabolism, such as insufflation (e.g., in nasal sprays or snuffs), as well as by transdermal and mucosal (e.g., sublingual, buccal, or rectal) absorption (see generally, Barker. Psychopharmacol. (Berl). 2022; 239(6):1749-1763).

In the brain, DMT binds with nanomolar affinity to a variety of serotonin receptors, though its biological effects have been attributed to its agonistic and/or partial agonistic effect at $5-HT_{2A}$, $5-HT_{1A}$, and $5-HT_{2C}$ receptors (Keiser et al. Nature. 2009:462; 175-181). The subjective effects of DMT are specifically attributed to its agonism of $5-HT_{2A}$ receptors (Nichols. Pharmacol Ther. 2004:101; 131-181; Nichols. Pharmacol Rev. 2016:68(2); 264-355). DMT is rapidly eliminated from the body; the half life of DMT from the brain is less than six minutes, and less than 16 minutes from the blood (Brito-da-Costa et al. Pharmaceuticals (Basel). 2020; 13(11):334; Vogt et al. Transl Psychiatry. 2023; 13(1):172).

Consumption of DMT produces a brief, intense psychedelic experience characterized by an altered emotional state, a feeling of dissociation from the body, and vivid visual hallucinations. Many DMT users report a feeling of being launched into another dimension or realm that transcends time and space. Many leave the experience with a profound, changed perspective on life and strong persisting positive changes in life satisfaction, purpose, and meaning (Liester & Prickett. J Psychoactive Drugs. 2012:44(3); 200-208).

The known physiological and psychological effects and anecdotal reports of users suggest that DMT has significant therapeutic potential (Lancelotta R, Davis A K. Therapeutic potential of fast-acting synthetic tryptamines. In: Handbook of Medical Hallucinogens. The Guilford Press; 2021:215-226). Studies suggest that endogenous DMT may be involved in neuroprotection, development, growth, maintenance, and repair in the brain (Frecska et al. J Neural Transm. 2013; 120(9):1295-1303; Barker. Psychopharmacology (Berl). 2022; 239(6):1749-1763). Further, DMT has been implicated in immunomodulatory and inflammatory pathways linked to depression and Alzheimer's disease (Szabo. Front Immunol. 2015; 6:358). Finally, evidence from both animal and human studies suggest that DMT may be useful in the treatment of anxiety disorders, depression, and substance abuse disorders (Rodrigues et al. J Psychoactive Drugs. 2019; 51(4):299-310).

Despite the therapeutic potential of DMT, the rapid onset and intensity of the drug's effects can cause psychological effects including disorientation, acute anxiety, and emotional distress. DMT can also cause adverse physical effects including diarrhea, nausea, vomiting, elevated heart rate, and elevated blood pressure (Cameron et al. ACS Chem Neurosci. 2018; 9(10):2344-2357). Other adverse effects include, as examples, dizziness, agitation, and muscle incoordination. Determinations and measurements of such adverse effects (e.g., physical and/or psychological side effects) will be known to those of ordinary skill.

These adverse effects may undermine the potential benefits of the DMT experience in some individuals, or under certain conditions. In some embodiments, reducing adverse effects of the DMT experience may lead to improvements in the DMT experience, thereby enhancing therapeutic or personal outcomes in an individual.

In some embodiments, a disclosed method comprises administering DMT, or a pharmaceutically acceptable salt thereof, in a dose of between about 0.02 mg/kg and 0.20 mg/kg, 0.03 mg/kg and 0.13 mg/kg, 0.03 mg/kg and 0.07 mg/kg, 0.05 mg/kg and 0.10 mg/kg, or about 0.08 mg/kg. In some embodiments, the dose of the DMT is between about 0.02 mg/kg and 0.20 mg/kg. In some embodiments, the dose of the DMT is between about 0.03 mg/kg and 0.13 mg/kg. In some embodiments, the dose of the DMT is between about 0.03 mg/kg and 0.07 mg/kg. In some embodiments, the dose of the DMT is between about 0.05 mg/kg and 0.10 mg/kg. In some embodiments, the dose of the DMT is about 0.08 mg/kg. In some embodiments, the dose of the DMT is about 0.05 mg/kg.

In some embodiments, a disclosed method comprises administering DMT, or a pharmaceutically acceptable salt thereof, in a dose of between about 0.20 mg/kg and 1.0 mg/kg, 0.20 mg/kg and 0.80 mg/kg, 0.20 mg/kg and 0.60 mg/kg, 0.30 mg/kg and 0.80 mg/kg, or 0.30 mg/kg and 0.60 mg/kg. In some embodiments, the dose of the DMT is between about 0.20 mg/kg and 1.0 mg/kg. In some embodiments, the dose of the DMT is between about 0.20 mg/kg and 0.80 mg/kg. In some embodiments, the dose of the DMT is between about 0.20 mg/kg and 0.60 mg/kg. In some embodiments, the dose of the DMT is between about 0.30 mg/kg and 0.80 mg/kg. In some embodiments, the dose of the DMT is between about 0.30 mg/kg and 0.60 mg/kg. In some embodiments, the DMT is administered at a dose of from about 0.1 to 1.0 mg/kg, 0.2 to 0.7 mg/kg, 0.2 to 0.5 mg/kg, or 0.3 to 0.4 mg/kg In some embodiments, a disclosed method comprises administering DMT, or a pharmaceutically acceptable salt thereof, in a dose of between about 1 mg and 10 mg, 2 mg and 8 mg, 3 mg and 6 mg, or about 5 mg. In some embodiments, the dose of DMT is between about 1 mg and 10 mg. In some embodiments, the dose of DMT is between about 10 mg and 30 mg. In some embodiments, the dose of DMT is between about 15 mg and 25 mg. In some embodiments, the dose of DMT is between about 2 mg and 8 mg. In some embodiments, the dose of DMT is between about 3 mg and 6 mg. In some embodiments, the dose of DMT is about 3 mg. In some embodiments, the dose of DMT is about 5 mg. In some embodiments, the dose of DMT is about 6 mg. In some embodiments, the dose of DMT is about 8 mg. In some embodiments, the dose of DMT is about 10 mg. In some embodiments, the dose of DMT is about 12 mg. In some embodiments, the dose of DMT is about 15 mg.

In some embodiments, a disclosed method comprises administering DMT, or a pharmaceutically acceptable salt thereof, in a dose of between about 15 mg and 150 mg, 25 mg and 125 mg, 20 mg and 50 mg, or 50 mg and 100 mg. In some embodiments, the dose of DMT is between about 15 mg and 150 mg. In some embodiments, the dose of the DMT is between about 25 mg and 125 mg. In some preferred embodiments, the dose of the DMT is between about 20 mg and 50 mg. In some embodiments, the dose of the DMT is between about 50 mg and 100 mg. In some embodiments, the dose of the DMT is about 5 to 50 mg, 10 to 40 mg, 15 to 30 mg, or 20 to 25 mg. In some embodiments, the dose of the DMT is about 5 to 50 mg. In some embodiments, the dose of the DMT is about 10 to 40 mg. In some embodiments, the dose of the DMT is about 15 to 30 mg. In some embodiments, the dose of the DMT is about 20 to 25 mg. In some embodiments, the dose of the DMT is about 5 mg. In some embodiments, the dose of the DMT is about 10 mg. In some embodiments, the dose of the DMT is about 15 mg. In some embodiments, the dose of the DMT is about 20 mg. In some embodiments, the dose of the DMT is about 25 mg. In some embodiments, the dose of the DMT is about 30 mg. In some embodiments, the dose of the DMT is about 40 mg. In some embodiments, the dose of the DMT is about 50 mg. In some embodiments, the dose of the DMT is about 75 mg. In some embodiments, the dose of the DMT is about 100 mg.

In some embodiments, the disclosed method comprises multiple administrations of DMT during the administration period of the long-acting tryptamine. In some embodiments, the DMT is administered at least once per hour. In some embodiments, the DMT is administered twice per hour, three times per hour, or more than three times per hour. In some embodiments, the DMT is administered about once per hour. In some embodiments, the DMT is administered about once every two hours. In some embodiments, the DMT is administered about once every three hours.

In some embodiments, a disclosed method comprises administering DMT, or a pharmaceutically acceptable salt thereof, in a total dose (i.e., a cumulative amount of DMT doses administered in an administration session which comprises two or more separate administrations of DMT) of between about 50 mg and 500 mg, 30 mg and 300 mg, 20 mg and 200 mg, or 10 mg and 100 mg. A total dose of DMT may be the cumulative amount of two DMT doses, three DMT doses, four DMT doses, five DMT doses or more than five DMT doses.

In some embodiments, the DMT is administered before or during the subjective peak of the effects of the long-acting tryptamine. In other embodiments, including in some preferred embodiments, the DMT is administered after the subjective peak of the effects of the long-acting tryptamine. In some embodiments, the DMT is administered during or after the subjective peak of the effects of the long-acting tryptamine. The subjective peak of the effects of the long-acting tryptamine can be readily determined by one of skill, including by both quantitative methods (e.g., measurement or estimation of the maximum serum concentration ($C_{max}$) of the long-acting tryptamine, evaluating an individual using a questionnaire, for instance, the Mystical Experience Questionnaire, the Challenging Experience Questionnaire, or the Hallucinogen Rating Scale), or by qualitative methods (e.g., interviewing the subject).

In some embodiments, the DMT is administered intramuscularly, intravenously, or by inhalation. In some embodiments, the DMT is administered intramuscularly. In some embodiments, the DMT is administered intravenously.

In some embodiments, the DMT is administered to the subject by inhalation. In some embodiments, the DMT is prepared as a dry powder for inhalation (e.g., using a dry powder inhaler (e.g., ProAir®). In some embodiments, inhaling the DMT comprises vaporizing the DMT. In some embodiments, the DMT is prepared as a liquid formulation for vaporization and inhalation, and is administered, e.g., using a device having a vape cartridge, a refillable pen (Uwell, SMOK®, Vaporesso, Geekvape), a single-use pen, a variable voltage pen (e.g., CCell® Fino Battery, a variable temperature pen, a modified pen, an e-cigarette (e.g., Puff Bar™, NJOY®, Breeze Smoke™), a cigalike, an e-cigar, an e-pipe (e.g., ePuffer®), or a heat-not-burn device.

In some embodiments, wherein the DMT is prepared as a vaporizable formulation, the formulation comprises DMT dissolved in a suitable base liquid. Base liquids include, for example, propylene glycol (PG), vegetable glycerin (VG), or a combination thereof. In some embodiments, the base liquid comprises between about 1% and 100% (v/v) of PG. In some embodiments, the base liquid comprises between about 1% and 100% (v/v) of VG. In some embodiments, the base liquid comprises only PG. In some embodiments, the base liquid comprises only VG. Where the formulation comprises a base liquid which is a mixture, such as a mixture of PG and VG, the mixture can be in any ratio, such as from 1:100 to 100:1 PG:VG. In embodiments, the ratio of PG:VG is any of 80:20, 70:30, 60:40, 50:50, 40:60, 30:70, or 20:80.

Vaporizable formulations can be prepared according to known methods. An exemplary method comprises dissolving a weighed quantity of DMT into a measured (e.g., weighed, or measured by volume) amount of base liquid. In some embodiments, heat is applied to the DMT/base liquid mixture to melt the DMT and/or facilitate its dissolution and mixing into a homogeneous solution. In some embodiments, the formulation may comprise one or more excipients. Suitable excipients include, for example, flavoring agents, colorants, dyes, pigments, antioxidants, solvents, humectants, viscosity modifiers, solubilizers, complexing agents, preservatives, pH adjusting agents, opacifiers, surfactants, and gelling agents.

In some embodiments, wherein the DMT is prepared as a vaporizable formulation, the formulation comprises DMT and a base liquid (e.g., PG, VG, or a mixture of PG and VG) in a ratio from about 1:1 to about 10:1, on a weight/weight (w/w) or weight/volume (w/v) basis. In some embodiments, the formulation comprises DMT and a base liquid in a ratio of about 1:1, 2:1, 3:1, 4:1, 5:1, 6:1, 7:1, 8:1, 9:1, or 10:1 (w/w). In some embodiments, the formulation comprises DMT and a base liquid in a weight ratio of about 2:1, 3:1, 4:1, 5:1, or 6:1 (w/w). In some embodiments, the formulation comprises DMT and a base liquid in a ratio of about 1:1, 2:1, 3:1, 4:1, 5:1, 6:1, 7:1, 8:1, 9:1, or 10:1 (w/v). In some embodiments, the formulation comprises DMT and a base liquid in a weight ratio of about 2:1, 3:1, 4:1, 5:1, or 6:1 (w/v). In some such embodiments, the base liquid is PG.

In some embodiments, wherein the DMT is prepared as a vaporizable formulation, the formulation comprises DMT and a base liquid (e.g., PG, VG, or a mixture of PG and VG) in a ratio from about 10:1 to about 1:1, on a weight/weight (w/w) or weight/volume (w/v) basis. In some embodiments, the formulation comprises DMT and a base liquid in a ratio of about 1:1, 1:2, 1:3, 1:4, 1:5, 1:6, 1:7, 1:8, 1:9, or 1:10 (w/w). In some embodiments, the formulation comprises DMT and a base liquid in a weight ratio of about 1:2, 1:3, 1:4, 1:5, or 1:6 (w/w). In some embodiments, the formulation comprises DMT and a base liquid in a ratio of about 1:1, 1:2, 1:3, 1:4, 1:5, 1:6, 1:7, 1:8, 1:9, or 1:10 (w/v). In some embodiments, the formulation comprises DMT and a base liquid in a weight ratio of about 1:2, 1:3, 1:4, 1:5, or 1:6 (w/v). In some such embodiments, the base liquid is PG.

In some embodiments, for example wherein DMT is vaporized directly, the DMT is freebase DMT. In some embodiments, the DMT is directly vaporized by applying heat using any suitable apparatus known to those of skill in the art (such as a glass pipe, a handheld vaporizer, or a desktop vaporizer (e.g., a VOLCANO® vaporizer (Storz & Bickel), Ditanium Vapor, Arizer Tech), or any other like means, as appreciated by those in the art).

c. Benzodiazepines

In some embodiments, the disclosed method comprises administering to an individual a benzodiazepine, or a pharmaceutically acceptable salt thereof, in combination with the long-acting tryptamine, the DMT, and optionally the NMDA receptor antagonist (e.g., ketamine).

Benzodiazepines are positive allosteric modulators of $GABA_A$ receptors. $GABA_A$ receptors are ligand-gated chloride ion channels located at the postsynaptic cell sites in synapses around the central nervous system (Dell'osso et al. Eur Psychiatry. 2013; 28(1):7-20). Unlike other positive allosteric modulators that increase ligand binding, benzodiazepine binding increases the total conduction of chloride ions through the $GABA_A$ receptor into the cell when GABA is already bound to the receptor. The increased flux of chloride ions into the neuron hyperpolarizes it, decreasing the chances it will fire an action potential. The inhibitory effect of GABA is thus potentiated by benzodiazepines, leading to their depressant-related effects (Edinoff et al. Neurol Int. 2021; 13(4):594-607).

The effects of benzodiazepines have resulted in their use for treating a variety of conditions including anxiety disorders, affective disorders, sleep disorders, alcohol withdrawal, delirium, neuroleptic related conditions, and psychosis-related behaviors (Dell'osso et al. Eur Psychiatry. 2013; 28(1):7-20). Benzodiazepines can have a strong anxiolytic effect, and thus have been prescribed for anxiety disorders such as panic disorder and generalized anxiety disorder (Edinoff et al. Neurol Int. 2021; 13(4):594-607; Cloos et al. Curr Opin Psychiatry. 2009; 22(1):90-95). In some embodiments, administration of a benzodiazepine is useful in ameliorating acute anxiety symptoms in an individual.

In some embodiments, the benzodiazepine used in a disclosed method is selected from the group consisting of alprazolam, bromazepam, chlordiazepoxide, clobazam, clonazepam, clorazepate, diazepam, estazolam, etizolam, flunitrazepam, flurazepam, flutoprazepam, halazepam, ketazolam, loprazolam, lorazepam, lormetazepam, midazolam, nimetazepam, nitrazepam, oxazepam, prazepam, quazepam, temazepam, tetrazepam, and triazolam; or a pharmaceutically acceptable salt thereof. In some embodiments, the benzodiazepine is alprazolam. In some embodiments, the benzodiazepine is bromazepam. In some embodiments, the benzodiazepine is chlordiazepoxide. In some embodiments, the benzodiazepine is clobazam. In some embodiments, the benzodiazepine is clorazepate. In some embodiments, the benzodiazepine is diazepam. In some embodiments, the benzodiazepine is estazolam. In some embodiments, the benzodiazepine is etizolam. In some embodiments, the benzodiazepine is flunitrazepam. In some embodiments, the benzodiazepine is flurazepam. In some embodiments, the benzodiazepine is flutoprazepam. In some embodiments, the benzodiazepine is halazepam. In some embodiments, the benzodiazepine is ketazolam. In some embodiments, the benzodiazepine is loprazolam. In some embodiments, the benzodiazepine is lorazepam. In some embodiments, the benzodiazepine is lormetazepam. In some embodiments, the benzodiazepine is midazolam. In some embodiments, the benzodiazepine is nimetazepam. In some embodiments, the benzodiazepine is nitrazepam. In some embodiments, the benzodiazepine is oxazepam. In some embodiments, the benzodiazepine is prazepam. In some embodiments, the benzodiazepine is quazepam. In some embodiments, the benzodiazepine is temazepam. In some embodiments, the benzodiazepine is tetrazepam. In some embodiments, the benzodiazepine is triazolam.

In some preferred embodiments, the benzodiazepine is lorazepam, or a pharmaceutically acceptable salt thereof. Lorazepam is the generic name for ±7-chloro-5-(2-chlorophenyl)-1,3-dihydro-3-hydroxy-2H-1,4-benzodiazepin-2-one, which has the following structure:

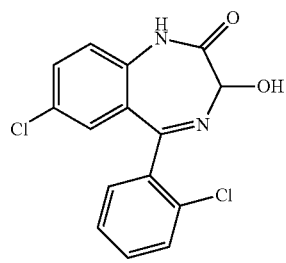 [SMILES: O=C1Nc2ccc(Cl)cc2C(c2ccccc2Cl)=NC1O]

Lorazepam is sold commercially in tablet form under the brand name ATIVAN®. The ATIVAN® tablets contain 0.5 mg, 1 mg, or 2 mg of lorazepam. The peak plasma concentrations ($C_{max}$) typically occur about 2 hours ($T_{max}$) after oral administration. Lorazepam has a half-life in human plasma of about 12 hours.

In some embodiments, wherein a disclosed method comprises administering to an individual lorazepam, or a pharmaceutically acceptable salt thereof, the dose of lorazepam is about 0.5 to 6 mg, including, 0.5 mg, 1 mg, 2 mg, 2.5 mg, 3 mg, 5 mg, and 6 mg. In some preferred embodiments, the dose of lorazepam is about 0.5 mg, 1 mg, or 2 mg. In some embodiments, the dose of lorazepam is about 0.5 mg. In some embodiments, the dose of lorazepam is about 1 mg. In some embodiments, the dose of lorazepam is about 2 mg.

In some embodiments, wherein a disclosed method comprises administering to an individual a benzodiazepine other than lorazepam, the dose will be adjusted according to the potency and therapeutic index of the benzodiazepine to be administered, according to methods known to those of skill in the art. For example, benzodiazepine dose equivalency charts (which are used by medical professionals to interconvert doses of different benzodiazepines) are one exemplary resource available to determine a suitable dose for use in a disclosed method.

In some embodiments, the benzodiazepine is administered before, during, or after the subjective peak of the effects of the long-acting tryptamine. In some preferred embodiments, the benzodiazepine is administered before the subjective peak of the effects of the long-acting tryptamine. In some preferred embodiments, the benzodiazepine is administered prior to the long-acting tryptamine. In such embodiments, the subjective effects of the benzodiazepine may be experienced by the subject prior to the onset of the effects of the long-acting tryptamine. In some embodiments, the benzodiazepine serves to reduce the anxiety associated with the onset of the physical or psychological effects of the long-acting tryptamine.

In some embodiments, the disclosed method does not comprise administering a benzodiazepine (e.g., if the subject declines the benzodiazepine, or if the subject's use of benzodiazepine would be contraindicated by a medical condition).

In some embodiments, the benzodiazepine is administered intranasally, sublingually, buccally, orally, intramuscularly, intravenously, or subcutaneously. In some embodiments, the benzodiazepine is administered orally, sublingually, or buccally. In some embodiments, the benzodiazepine is administered orally. In some embodiments, the benzodiazepine is administered sublingually or buccally.

In some embodiments, the benzodiazepine administered orally is a lorazepam tablet, such as an ATIVAN® tablet. In some embodiments, the benzodiazepine administered sublingually or buccally is a lorazepam sublingual tablet, such as an ATIVAN® sublingual tablet.

In some embodiments, a benzodiazepine analog or derivative, or a pharmaceutically acceptable salt thereof, can be used in a disclosed method in place of, or in addition to, the benzodiazepine. In some embodiments, a disclosed method comprises administering a thienodiazepine, or a pharmaceutically acceptable salt thereof. In some embodiments, the thienodiazepine is bentazepam, clotiazepam, etizolam, metizolam, deschloroetizolam, or fluclotizolam, or a pharmaceutically acceptable salt thereof. In some embodiments, a disclosed method comprises administering a thienotriazolodiazepine, or a pharmaceutically acceptable salt thereof. In some embodiments, the thienotriazolodiazepine is brotizolam, ciclotizolam, deschloroetizolam, etizolam, fluclotizolam, or metizolam, or a pharmaceutically acceptable salt thereof.

d. NMDA Antagonists

In some embodiments, the disclosed method comprises administering to an individual an NMDA receptor antagonist, or a pharmaceutically acceptable salt thereof, in combination with the long-acting tryptamine, the DMT, and optionally a benzodiazepine.

NMDA receptor antagonists (equivalently, "NMDA antagonists" or "NMDAR antagonists") are a class of drugs that antagonize the N-methyl-D-aspartate receptor (NMDAR). At high doses, NMDA antagonists can induce dissociative anesthesia, while lower subanesthetic doses can have mildly stimulating effects. Ketamine, an NMDA antagonist used in some disclosed methods, has been used for several therapeutic indications including pain and treatment-resistant depression (Zhang et al. Expert Rev Neurother. 2019:19(1); 83-92).

Ketamine is active at multiple neurotransmitter receptors and transporters, including some shared with psychedelics (Mathai et al. J Affect Disord. 2020; 264:123-129). These shared signaling pathways may underlie the effects of ketamine, which induces comparable brain activity and shared phenomenology with that of tryptamine, ergoline, and phenethylamine psychedelics (Vollenweider et al. Nat Rev Neurosci. 2010; 11(9):642-651). Further, neuroimaging studies have shown that ketamine reduces brain activation in regions associated with self-monitoring, increases activity in regions associated with emotional blunting, and increases neural activity in reward processing areas (Ionescu et al. Harv Rev Psychiatry. 2018; 26(6):320-339). Together, these effects suggest that ketamine may have synergistic effects with psychedelics, and improve the overall psychedelic experience at low doses.

In some embodiments, the NMDA antagonist is ketamine, or a pharmaceutically acceptable salt thereof. In some embodiments, the ketamine is racemic (±)-ketamine, or a pharmaceutically acceptable salt thereof. In other embodiments, the ketamine is S(+)-ketamine (esketamine) or R(−)-ketamine (arketamine), or a pharmaceutically acceptable salt thereof. In some embodiments, the ketamine is a non-racemic mixture of esketamine and arketamine, in any enantiomeric excess between 0% and 100% of either enantiomer.

Ketamine, and the individual enantiomers of ketamine, have the following structures:

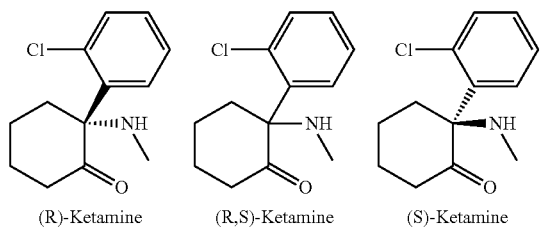

(R)-Ketamine    (R,S)-Ketamine    (S)-Ketamine

In some embodiments, the NMDA antagonist is ketamine, esketamine, arketamine, or a non-racemic mixture of ketamine enantiomers, in any proportions.

In some embodiments, the NMDA antagonist is a ketamine metabolite, or a pharmaceutically acceptable salt thereof. In some embodiments, the ketamine metabolite is a norketamine, a dehydronorketamine, a hydroxyketamine, or a hydroxynorketamine, including isomers thereof, and pharmaceutically acceptable salts thereof. In some embodiments, the ketamine metabolite is any of the 12 HNK metabolites formed from the metabolism of ketamine in vivo, including any of the stereoselective metabolites of esketamine or arketamine, including (R,S)-norketamine (NK), (R,S)-dehydronorketamine, hydroxyketamines, and hydroxynorketamines (HNKs), including by example (2S,6S;2R,6R)-HNK, (2R,4R;2S,4S-2S,6R;2R,6S)-HNK, and (2R,4S;2S,4R-2S,5S;2R,5R)-HNK (see, e.g., Farmer, 2020), and 2R,6R-hydroxynorketamine as well as its prodrugs (see, e.g., U.S. Pub. No. 2019/0380978A1), 2S,6S-hydroxynorketamine (see, e.g., U.S. Pub. No. 2020/0157040A1), as well as conformationally stabilized analogs of ketamine metabolites, e.g., 6-hydroxyketamine and 6-hydroxynorketamine (see, e.g., PCT Pub. No. WO2018/104729A1), and dehydronorketamines (DHNKs) such as R-5,6-dehydronorketamine and S-5,6-dehydronorketamine (see, e.g., PCT Pub. No. WO2019/058145A1).

In some embodiments, the NMDA antagonist is memantine, amantadine, rimantadine, nitromemantine (YQW-36), or acamprosate. In some embodiments, the NMDA antagonist is pethidine, levorphanol, methadone, dextropropoxyphene, tramadol, or ketobemidone. In some embodiments, the NMDA antagonist is dextromethorphan (DXM), dextrorphan, or dextrallorphan (DXA). In some embodiments, the NMDA antagonist is ephenidine (NEDPA, EPE), β-keto-ephenidine, diphenidine (1,2-DEP, DPD, DND), isopropylphenidine (NPDPA), methoxphenidine (MXP), fluorolintane (2-FPPP, 2-F-DPPy), remacemide, or another diarylethylamine. In some embodiments, the NMDA antagonist is gacyclidine (GK-11), neramexane, lanicemine (AZD6765), dizocilpine (MK-801), 8a-phenyldecahydroquinoline (8A-PDHQ), remacemide, ifenprodil, traxoprodil (CP-101,606), eliprodil (SL-82.0715), etoxadrol (CL-1848C), dexoxadrol, WMS-2539, NEFA, delucemine (NPS-1506), aptiganel (Cerestat; CNS-1102), midafotel (CPPene; SDZ EAA 494), dexanabinol (HU-211 or ETS2101), selfotel (CGS-19755), 7-chlorokynurenic acid (7-CKA), 5,7-dichlorokynurenic acid (5,7-DCKA), L-683344, L-689560, L-701324, GV150526A, GV196771A, CERC-301 (MK-0657), atomoxetine, LY-235959, CGP 61594, CGP 37849, CGP 40116 or CGP 37849, LY-233536, PEAQX (NVP-AAM077), ibogaine or noribogaine (or an ibogaine metabolite, ibogaine analog, or ibogaine derivative), Ro 25-6981, GW468816, EVT-101, indantadol, perzinfotel (EAA-090), SSR240600, 2-MDP (U-23807A) or AP-7.

In some embodiments, the NMDA antagonist is ketamine (and its analogs, e.g., tiletamine), phencyclidine (and its analogs, e.g., tenocyclidine, eticyclidine, rolicyclidine), or methoxetamine (and its analogs). In some embodiments, the ketamine analog is DXE (2'-Oxo-PCM, DCK), methoxetamine (2-MeO-2-deschloroketamine, MXE), 3-MeO-PCE, KEA-1010, N-ethyldeschloroketamine (2'-Oxo-PCE, O-PCE), 2-fluoro-deschloroketamine (2-(2-fluorophenyl)-2-methylamino-cyclohexanone, 2-FDCK), deschloro-ketamine (2-phenyl-2-methylamino-cyclohexanone), or alkyne-norketamine (A-NK), including isomers thereof, and pharmaceutically acceptable salts thereof. In some embodiments, the NMDA antagonist is an arylcyclohexylamine or an arylcyclohexylamine derivative, such as disclosed in, e.g., WO2022/047256A1, US2022/0041540A1, and WO2021/255737A1, incorporated by reference as if fully set forth herein.

In general, it will be appreciated that a single dose of NMDA antagonist (in a mg dose amount to be administered to the subject), may be e.g., 1 mg or less, at least 1 mg, at least 10 mg, at least 15 mg, at least 20 mg, at least 25 mg, at least 30 mg, at least 35 mg, at least 40 mg, at least 45 mg, or at least 50 mg, as well as amounts within these ranges. In some embodiments, the dose of ketamine is between about 10 mg and about 50 mg, including 10 mg, 15 mg, 20 mg, 25 mg, 30 mg, 35 mg, 40 mg, 45 mg, and 50 mg. In some preferred embodiments, the dose of ketamine is between about 20 mg and 30 mg.

In some embodiments, the disclosed method comprises multiple administrations of an NMDA antagonist, or a pharmaceutically acceptable salt thereof, during the administration period of the long-acting tryptamine. In some embodiments, the NMDA antagonist is administered at least once per hour. In some embodiments, the NMDA antagonist is administered twice per hour, three times per hour, or more than three times per hour. In some embodiments, the NMDA antagonist is administered about once per hour. In some embodiments, the NMDA antagonist is administered about once every two hours. In some embodiments, the NMDA antagonist is administered about once every three hours.

In some embodiments, the NMDA antagonist is administered intranasally, sublingually, buccally, orally, intramuscularly, intravenously, or subcutaneously. In some preferred embodiments, the NMDA antagonist is administered orally or intranasally. In some embodiments, the NMDA antagonist is administered orally. In some embodiments, the NMDA antagonist is administered intranasally.

For every disclosed NMDA receptor antagonist, the disclosure also will be understood to include the pharmaceutically acceptable salts thereof.

In some embodiments, the disclosed method does not comprise administering an NMDA antagonist (e.g., if the subject declines the NMDA antagonist, or if the subject's use of NMDA antagonist would be contraindicated by a medical condition).

D. ADDITIONAL ACTIVE AGENTS

In some embodiments, a disclosed method comprises administering to an individual an additional active agent in combination with any of a long-acting psychedelic, DMT, a benzodiazepine, and an NMDA antagonist. The additional active agent may contribute to or provide an additional therapeutic effect, or contribute to or provide a synergistic effect.

In embodiments, the additional active agent may be any of amino acids, antioxidants, anti-inflammatory agents, analgesics, antineuropathic and antinociceptive agents, antimigraine agents, anxiolytics, antidepressants, antipsychotics, anti-PTSD agents, cannabinoids, NMDA antagonists, dissociatives, antiemetics, antihistamines, antihypertensives, anticonvulsants, antiepileptics, neuroprotectants, nootropics, entheogens, entactogens and empathogens, psychedelics, monoamine oxidase inhibitors (including RIMAs), tryptamines, terpenes, phenethylamines, sedatives, stimulants, serotonergic agents, and vitamins. These agents may be in ion, freebase, or salt form, and may be isomers, prodrugs, derivatives (preferably physiologically functional derivatives), or analogs.

In some embodiments, the additional active agent is a monoamine oxidase inhibitor (MAOI). There are two isoforms of MAO, monoamine oxidase-A (MAO-A) and monoamine oxidase-B (MAO-B). MAO-A has been shown to break down serotonin, melatonin, norepinephrine, epinephrine, and other monoamines ingested in food. MAO-B metabolizes similar compounds with a preference to oxidize phenylethylamines, such as dopamine. (Shih et al., Pol J Pharmacol. 1999; 51(1):25-29). Certain substrates, like tyramine, are metabolized by both MAO-A and MAO-B. (Finberg et al., Br. J Pharmacol, 1982; 77(1):13). Herein, the terms "monoamine oxidase inhibitor" and "MAOI" refers to any compound, whether natural or synthetic, that exhibits the ability to inhibit the enzymatic activity of MAO, including MAO-A and MAO-B. It encompasses all chemical structures, including organic molecules, peptides, proteins, nucleic acids, derivatives, analogs, and combinations thereof, capable of interfering with the catalytic function of monoamine oxidase enzymes, thereby preventing or reducing the metabolism or breakdown of monoamine neurotransmitters. The terms "monoamine oxidase inhibitor" and "MAOI" further encompasses reversible, irreversible, competitive, non-competitive, selective, and non-selective inhibitors, as well as any substance that indirectly modulates or regulates monoamine oxidase activity through allosteric, regulatory, or indirect mechanisms. In some embodiments, the MAOI is an MAO-A-selective inhibitor. In some embodiments, the MAOI is an MAO-B-selective inhibitor. In some embodiments, the MAOI is a non-selective inhibitor.

In some embodiments, a disclosed method comprises administering to an individual a MAOI as a pure or substantially pure compound. In some embodiments, the MAOI is selected from the group consisting of isocarboxazid, pargyline, selegiline, furazolidone, phenelzine, amiflamine, iproniazid, nialamide, tranylcypromine, octamoxin, phenoxypropazine, pivalyl benzhydrazine, iproclozide, iproniazide, bifemelane, prodipine, benmoxin, etryptamine, fenoxypropazine, mebanazine, pheniprazine, safrazine, hypericine, iproniazid phosphate, phenelzine sulphate, tranylcypromine sulphate, methylene blue, moclobemide, brofaromine, befloxatone, toloxatone, clorgyline, cimoxatone, bazinaprine, harmine, harmaline, sercloremine, esuprone, pirlindole, metralindole, and tetrindole.

In some embodiments, a disclosed method comprises administering to an individual a MAOI as as a mixture of compounds, for example, obtained by combining any two or more MAOIs disclosed herein or otherwise known to one of skill; or obtained by extraction of a biological substance that contains naturally occurring MAOIs. For example, beta-carboline (β-carboline)-type MAOIs (e.g., harmala alkaloids such as harmine and harmaline) are naturally occurring in numerous botanical sources, including *Banisteriopsis caapi*, tobacco, *Peganum harmala*, *Peganum nigellastrum*, *Zygophyllum fabago*, *Passiflora* spp., *Malpighiaceae* spp., lemon balm (*Melissa officinalis*), *Callaeum antifebrile*, and numerous others.

In some embodiments, a MAOI is administered to an individual as a component of a formulation comprising any of a long-acting psychedelic, DMT, a benzodiazepine, and an NMDA antagonist. In some embodiments, a disclosed method comprises administering a MAOI in the same formulation as the DMT. For example, the MAOI (whether present as a pure compound, mixture of pure compounds, or botanical extract) is in some embodiments included in a vaporizable formulation that also comprises DMT.

E. COMBINATIONS

In some embodiments, a disclosed method comprises administering a combination comprising any of a long-acting psychedelic, DMT, a benzodiazepine, and an NMDA antagonist.

In some embodiments, the method comprises administering a long-acting psychedelic and DMT. In some embodiments, the method comprises administering a long-acting psychedelic, DMT, and a benzodiazepine. In some embodiments, the method comprises administering a long-acting psychedelic, DMT, and an NMDA antagonist. In some embodiments, the method comprises administering a long-acting psychedelic, DMT, a benzodiazepine, and an NMDA antagonist.

In some embodiments, the long-acting tryptamine is psilacetin. In some embodiments, the long-acting tryptamine is psilocybin. In some embodiments, the long-acting tryptamine is psilocin. In some embodiments, the method comprises administering psilacetin at a dose of from about 0.1 to 1.0 mg/kg, 0.2 to 0.7 mg/kg, 0.2 to 0.5 mg/kg, or 0.3 to 0.4 mg/kg. In some embodiments, the method comprises administering psilacetin at a dose of between about 15 mg and 300 mg, 25 mg and 200 mg, 20 mg and 50 mg, or 50 mg and 100 mg. In some embodiments, the method comprises administering psilocybin at a dose of from about 0.1 to 1.0 mg/kg, 0.2 to 0.7 mg/kg, 0.2 to 0.5 mg/kg, or 0.3 to 0.4 mg/kg. In some embodiments, the method comprises administering psilocybin at a dose of between about 15 mg and 300 mg, 25 mg and 200 mg, 20 mg and 50 mg, or 50 mg and 100 mg. In some embodiments, the method comprises administering psilocin at a dose of from about 0.1 to 1.0 mg/kg, 0.2 to 0.7 mg/kg, 0.2 to 0.5 mg/kg, or 0.3 to 0.4 mg/kg. In some embodiments, the method comprises administering psilocin at a dose of between about 15 mg and 300 mg, 25 mg and 200 mg, 20 mg and 50 mg, or 50 mg and 100 mg.

In some embodiments, the DMT is freebase DMT. In some embodiments, the DMT is a pharmaceutically acceptable salt of DMT. In some embodiments, the DMT is DMT fumarate. In some embodiments, the DMT is administered at a dose of about 5 to 50 mg, 10 to 40 mg, 15 to 30 mg, 20 to 25 mg. In some embodiments, the DMT is administered at a dose of about 0.1 to 1.0 mg/kg, 0.2 to 0.7 mg/kg, 0.2 to 0.5 mg/kg, or 0.3 to 0.4 mg/kg.

In some embodiments, the benzodiazepine is any benzodiazepine disclosed herein. In some embodiments, the benzodiazepine is lorazepam, or a pharmaceutically acceptable salt thereof. In some embodiments, the method comprises administering lorazepam at a dose of from about 0.5 to 2 mg, about 0.5 to 1.5 mg, about 0.5 to 1 mg, about 0.5 mg, about 1.0 mg, about 1.5 mg, or about 2.0 mg.

In some embodiments, the NMDA antagonist is ketamine, or a pharmaceutically acceptable salt thereof. In some embodiments, the method comprises administering ketamine at a dose of from about 10 to 50 mg, 10 to 30 mg, 10 to 20 mg, 15 to 30 mg, 15 to 20 mg, or 20 to 30 mg. In some embodiments, the ketamine is administered at a dose of about 0.1 to 2.0 mg/kg, 0.15 to 1.5 mg/kg, 0.15 to 1.0 mg/kg, 0.15 to 0.5 mg/kg, 0.15 to 0.4 mg/kg, 0.2 to 1.5 mg/kg, 0.2 to 1.0 mg/kg, 0.2 to 0.5 mg/kg, or 0.2 to 0.4 mg/kg.

The bioavailability of ketamine may differ depending on the method of administration utilized, but will be known or ascertainable to those of skill, and therefore dose and dosage may be modified according to that bioavailability and ordinary skill. For example, the relative bioavailability of oral ketamine is said to be between about 17% and about 24%, intramuscular ketamine is about 93%, intranasal ketamine is about 50%, rectal ketamine is about 30%, sublingual ketamine is about 30%, and nasal ketamine is about 45% (see, e.g., U.S. Pat. App. No. 2022/0125742A1, incorporated herein by reference).

In some embodiments wherein a disclosed method is used to treat a disease or disorder, it will be readily appreciated that dose and dosage may vary depending upon the onset, progression, severity, frequency, duration, probability of, or susceptibility of the symptom to which treatment is directed, clinical endpoint desired, previous, simultaneous or subsequent treatments, general health, age, gender, and race of the individual, bioavailability, potential adverse systemic, regional, or local side effects, the presence of other disorders or diseases in the individual, and other factors that will be appreciated by those in the art (e.g., medical or familial history).

In some embodiments, the method comprises administering a first long-acting tryptamine, a second long-acting tryptamine, and DMT. In some embodiments, the first long-acting tryptamine is psilacetin and the second long-acting tryptamine is another tryptamine (e.g., as disclosed herein or otherwise known to one of skill). In some embodiments, the first long-acting tryptamine is psilacetin and the second long-acting tryptamine is a 4-substituted tryptamine. In some embodiments, the first long-acting tryptamine is psilacetin and the second long-acting tryptamine is a 4-acetoxytryptamine. In some embodiments, the first long-acting tryptamine is psilacetin and the second long-acting tryptamine is a 4-phosphoryloxytryptamine. In some embodiments, the first long-acting tryptamine is psilacetin and the second long-acting tryptamine is psilocybin. In some embodiments, the first long-acting tryptamine is psilacetin and the second long-acting tryptamine is a 4-hydroxytryptamine. In some embodiments, the first long-acting tryptamine is psilacetin and the second long-acting tryptamine is psilocin. In some embodiments, the first long-acting tryptamine is psilacetin and the second long-acting tryptamine is 4-HO-MiPT. In some embodiments, the first long-acting tryptamine is psilacetin and the second long-acting tryptamine is 4-HO-MET.

In some embodiments, the method comprises administering:
  i. a first long-acting tryptamine, or a pharmaceutically acceptable salt thereof;
  ii. DMT, or a pharmaceutically acceptable salt thereof;
  iii. optionally, a benzodiazepine, or a pharmaceutically acceptable salt thereof; and
  iv. optionally, an NMDA antagonist, or a pharmaceutically acceptable salt thereof.

In some embodiments, the method comprises administering:
  i. a first long-acting tryptamine, or a pharmaceutically acceptable salt thereof;
  ii. optionally, a second long-acting tryptamine, or a pharmaceutically acceptable salt thereof;
  iii. DMT, or a pharmaceutically acceptable salt thereof;
  iv. optionally, a benzodiazepine, or a pharmaceutically acceptable salt thereof; and
  v. optionally, an NMDA antagonist, or a pharmaceutically acceptable salt thereof.

In some embodiments, the method comprises administering:
  i. psilacetin, or a pharmaceutically acceptable salt thereof;
  ii. optionally, a second long-acting tryptamine, or a pharmaceutically acceptable salt thereof;
  iii. DMT, or a pharmaceutically acceptable salt thereof;
  iv. optionally, a benzodiazepine, or a pharmaceutically acceptable salt thereof; and
  v. optionally, an NMDA antagonist, or a pharmaceutically acceptable salt thereof.

In some embodiments, the method comprises administering:
  i. psilacetin, or a pharmaceutically acceptable salt thereof;
  ii. optionally, a 4-substituted tryptamine, or a pharmaceutically acceptable salt thereof;
  iii. DMT, or a pharmaceutically acceptable salt thereof;
  iv. optionally, a benzodiazepine, or a pharmaceutically acceptable salt thereof; and
  v. optionally, an NMDA antagonist, or a pharmaceutically acceptable salt thereof.

In some embodiments, the method comprises administering:
  i. psilacetin, or a pharmaceutically acceptable salt thereof;
  ii. optionally, a 4-acetoxytryptamine, or a pharmaceutically acceptable salt thereof;
  iii. DMT, or a pharmaceutically acceptable salt thereof;
  iv. optionally, a benzodiazepine, or a pharmaceutically acceptable salt thereof; and
  v. optionally, an NMDA antagonist, or a pharmaceutically acceptable salt thereof.

In some embodiments, the method comprises administering:
  i. psilacetin, or a pharmaceutically acceptable salt thereof;
  ii. optionally, a 4-phosphoryloxytryptamine, or a pharmaceutically acceptable salt thereof;
  iii. DMT, or a pharmaceutically acceptable salt thereof;
  iv. optionally, a benzodiazepine, or a pharmaceutically acceptable salt thereof; and
  v. optionally, an NMDA antagonist, or a pharmaceutically acceptable salt thereof.

In some embodiments, the method comprises administering:
  i. psilacetin, or a pharmaceutically acceptable salt thereof;
  ii. optionally, psilocybin, or a pharmaceutically acceptable salt thereof;
  iii. DMT, or a pharmaceutically acceptable salt thereof;
  iv. optionally, a benzodiazepine, or a pharmaceutically acceptable salt thereof; and
  v. optionally, an NMDA antagonist, or a pharmaceutically acceptable salt thereof.

In some embodiments, the method comprises administering:
  i. psilacetin, or a pharmaceutically acceptable salt thereof;
  ii. optionally, a 4-hydroxytryptamine, or a pharmaceutically acceptable salt thereof;
  iii. DMT, or a pharmaceutically acceptable salt thereof;
  iv. optionally, a benzodiazepine, or a pharmaceutically acceptable salt thereof; and
  v. optionally, an NMDA antagonist, or a pharmaceutically acceptable salt thereof.

In some embodiments, the method comprises administering:
  i. psilocybin, or a pharmaceutically acceptable salt thereof;
  ii. psilocin, or a pharmaceutically acceptable salt thereof;
  iii. DMT, or a pharmaceutically acceptable salt thereof;
  iv. optionally, a benzodiazepine, or a pharmaceutically acceptable salt thereof; and
  v. optionally, an NMDA antagonist, or a pharmaceutically acceptable salt thereof.

In some embodiments, the method comprises administering:
  i. psilocybin and psilocin, as a psilocybin-producing fungus;
  ii. DMT, or a pharmaceutically acceptable salt thereof;
  iii. optionally, a benzodiazepine, or a pharmaceutically acceptable salt thereof; and
  iv. optionally, an NMDA antagonist, or a pharmaceutically acceptable salt thereof.

In some embodiments, the method comprises administering:
  i. psilocybin and psilocin, as an extract from a psilocybin-producing fungus;
  ii. DMT, or a pharmaceutically acceptable salt thereof;
  iii. optionally, a benzodiazepine, or a pharmaceutically acceptable salt thereof; and
  iv. optionally, an NMDA antagonist, or a pharmaceutically acceptable salt thereof.

In some embodiments, the method comprises administering:
  i. psilacetin, or a pharmaceutically acceptable salt thereof;
  ii. optionally, psilocin, or a pharmaceutically acceptable salt thereof;
  iii. DMT, or a pharmaceutically acceptable salt thereof;
  iv. optionally, a benzodiazepine, or a pharmaceutically acceptable salt thereof; and
  v. optionally, an NMDA antagonist, or a pharmaceutically acceptable salt thereof.

In some embodiments, the method comprises administering:
  i. psilacetin, or a pharmaceutically acceptable salt thereof;
  ii. optionally, 4-HO-MiPT, or a pharmaceutically acceptable salt thereof;
  iii. DMT, or a pharmaceutically acceptable salt thereof;
  iv. optionally, a benzodiazepine, or a pharmaceutically acceptable salt thereof; and
  v. optionally, an NMDA antagonist, or a pharmaceutically acceptable salt thereof.

In some embodiments, the method comprises administering:
  i. psilacetin, or a pharmaceutically acceptable salt thereof;
  ii. optionally, 4-HO-MET, or a pharmaceutically acceptable salt thereof;
  iii. DMT, or a pharmaceutically acceptable salt thereof;
  iv. optionally, a benzodiazepine, or a pharmaceutically acceptable salt thereof; and
  v. optionally, an NMDA antagonist, or a pharmaceutically acceptable salt thereof.

In some embodiments, the method comprises administering:
  i. a first long-acting tryptamine, or a pharmaceutically acceptable salt thereof;
  ii. optionally, a second long-acting tryptamine, or a pharmaceutically acceptable salt thereof;
  iii. DMT, or a pharmaceutically acceptable salt thereof;
  iv. optionally, lorazepam, or a pharmaceutically acceptable salt thereof; and
  v. optionally, an NMDA antagonist, or a pharmaceutically acceptable salt thereof.

In some embodiments, the method comprises administering:
  i. a first long-acting tryptamine, or a pharmaceutically acceptable salt thereof;
  ii. optionally, a second long-acting tryptamine, or a pharmaceutically acceptable salt thereof;
  iii. DMT, or a pharmaceutically acceptable salt thereof;
  iv. optionally, a benzodiazepine, or a pharmaceutically acceptable salt thereof; and
  v. optionally, ketamine, or a pharmaceutically acceptable salt thereof.

In some embodiments, the method comprises administering:
  i. a first long-acting tryptamine, or a pharmaceutically acceptable salt thereof;
  ii. DMT, or a pharmaceutically acceptable salt thereof;
  iii. a benzodiazepine, or a pharmaceutically acceptable salt thereof; and
  iv. optionally, ketamine, or a pharmaceutically acceptable salt thereof.

In some embodiments, the method comprises administering:
  i. a first long-acting tryptamine, or a pharmaceutically acceptable salt thereof;
  ii. DMT, or a pharmaceutically acceptable salt thereof;
  iii. optionally, a benzodiazepine, or a pharmaceutically acceptable salt thereof; and
  iv. ketamine, or a pharmaceutically acceptable salt thereof.

In some embodiments, the method comprises administering:
  i. psilacetin, or a pharmaceutically acceptable salt thereof;
  ii. DMT, or a pharmaceutically acceptable salt thereof;

iii. a benzodiazepine, or a pharmaceutically acceptable salt thereof; and
iv. optionally, ketamine, or a pharmaceutically acceptable salt thereof.

In some embodiments, the method comprises administering:
i. psilacetin, or a pharmaceutically acceptable salt thereof;
ii. DMT, or a pharmaceutically acceptable salt thereof;
iii. optionally, a benzodiazepine, or a pharmaceutically acceptable salt thereof; and
iv. ketamine, or a pharmaceutically acceptable salt thereof.

In some embodiments, the method comprises administering:
i. psilacetin, or a pharmaceutically acceptable salt thereof;
ii. DMT, or a pharmaceutically acceptable salt thereof;
iii. lorazepam, or a pharmaceutically acceptable salt thereof; and
iv. optionally, ketamine, or a pharmaceutically acceptable salt thereof.

In some embodiments, the method comprises administering:
i. psilacetin, or a pharmaceutically acceptable salt thereof;
ii. DMT, or a pharmaceutically acceptable salt thereof;
iii. lorazepam, or a pharmaceutically acceptable salt thereof; and
iv. ketamine, or a pharmaceutically acceptable salt thereof.

In some embodiments, the method comprises administering:
i. a first long-acting tryptamine, or a pharmaceutically acceptable salt thereof;
ii. DMT, or a pharmaceutically acceptable salt thereof; and
iii. a monoamine oxidase inhibitor, or a pharmaceutically acceptable salt thereof.

In some embodiments, the method comprises administering:
i. a first long-acting tryptamine, or a pharmaceutically acceptable salt thereof;
ii. DMT, or a pharmaceutically acceptable salt thereof;
iii. a benzodiazepine, or a pharmaceutically acceptable salt thereof; and
iv. a monoamine oxidase inhibitor, or a pharmaceutically acceptable salt thereof.

In some embodiments, the method comprises administering:
i. a first long-acting tryptamine, or a pharmaceutically acceptable salt thereof;
ii. DMT, or a pharmaceutically acceptable salt thereof;
iii. ketamine, or a pharmaceutically acceptable salt thereof; and
iv. a monoamine oxidase inhibitor, or a pharmaceutically acceptable salt thereof.

In some embodiments, the method comprises administering:
i. a first long-acting tryptamine, or a pharmaceutically acceptable salt thereof;
ii. DMT, or a pharmaceutically acceptable salt thereof;
iii. a benzodiazepine, or a pharmaceutically acceptable salt thereof;
iv. ketamine, or a pharmaceutically acceptable salt thereof; and
v. a monoamine oxidase inhibitor, or a pharmaceutically acceptable salt thereof.

In some embodiments, the method comprises administering:
i. a first long-acting tryptamine, or a pharmaceutically acceptable salt thereof;
ii. DMT, or a pharmaceutically acceptable salt thereof;
iii. lorazepam, or a pharmaceutically acceptable salt thereof;
iv. ketamine, or a pharmaceutically acceptable salt thereof; and
v. a monoamine oxidase inhibitor, or a pharmaceutically acceptable salt thereof.

In some embodiments, the method comprises administering:
i. a first long-acting tryptamine, or a pharmaceutically acceptable salt thereof; and
ii. a composition comprising DMT, or a pharmaceutically acceptable salt thereof, and a monoamine oxidase inhibitor, or a pharmaceutically acceptable salt thereof.

In some embodiments, the method comprises administering:
i. a first long-acting tryptamine, or a pharmaceutically acceptable salt thereof;
ii. a composition comprising DMT, or a pharmaceutically acceptable salt thereof, and a monoamine oxidase inhibitor, or a pharmaceutically acceptable salt thereof; and
iii. a benzodiazepine, or a pharmaceutically acceptable salt thereof.

In some embodiments, the method comprises administering:
i. a first long-acting tryptamine, or a pharmaceutically acceptable salt thereof;
ii. a composition comprising DMT, or a pharmaceutically acceptable salt thereof, and a monoamine oxidase inhibitor, or a pharmaceutically acceptable salt thereof; and
iii. ketamine, or a pharmaceutically acceptable salt thereof.

In some embodiments, the method comprises administering:
i. a first long-acting tryptamine, or a pharmaceutically acceptable salt thereof;
ii. a composition comprising DMT, or a pharmaceutically acceptable salt thereof, and a monoamine oxidase inhibitor, or a pharmaceutically acceptable salt thereof;
iii. a benzodiazepine, or a pharmaceutically acceptable salt thereof; and
iv. ketamine, or a pharmaceutically acceptable salt thereof.

In some embodiments, the method comprises administering:
i. a first long-acting tryptamine, or a pharmaceutically acceptable salt thereof;
ii. a composition comprising DMT, or a pharmaceutically acceptable salt thereof, and a monoamine oxidase inhibitor, or a pharmaceutically acceptable salt thereof;
iii. lorazepam, or a pharmaceutically acceptable salt thereof; and
iv. ketamine, or a pharmaceutically acceptable salt thereof.

F. METHODS OF ADMINISTRATION

In some aspects, provided are methods of administration or methods of administering a combination disclosed herein.

As used herein, the terms "subject," "user," "patient," and "individual" are used interchangeably, and refer to any mammal, preferably a human. Such terms will be understood to include one who has an indication for which the combinations, compositions, or methods described herein may be efficacious, or who otherwise may benefit by the invention. In general, all of the combinations, compositions, and methods of the invention will be appreciated to work for all individuals, although individual variation is to be expected, and will be understood.

In some aspects, the invention provides methods for using pharmacologically effective amounts of the compositions of the invention comprising the compounds disclosed herein in a mammal, and preferably a human. Such methods include those for improving the DMT experience.

Administration of compounds or compositions in an "effective amount," a "therapeutically effective amount," a "therapeutically effective dose," or a "pharmacologically effective amount," refers to an amount of a compound that is sufficient to provide a desired effect, for example, relieving to some extent one or more of the adverse effects of DMT use. The result can be reduction and/or alleviation of an adverse effects of DMT, or any other desired alteration of a biological system.

It is understood that an effective amount can vary from individual to individual due to variation in metabolism, age, weight, and general condition of the individual. The effective amount will vary depending upon the individual and effect sought, the manner of administration, and the like, all of which can readily be determined by one of skill. Additionally, pharmacogenomic (the effect of genotype on the pharmacokinetic, pharmacodynamic or efficacy profile of a compound) information about a particular individual may affect dosage used.

In some embodiments, the order and timing of administration of the compounds of a disclosed combination to an individual are based on the onset, peak, and duration of the compounds and the dosages administered. In some embodiments, the onset, peak, and duration of a compound can be estimated using pharmacokinetic parameters such as compound half-lives, plasma concentrations, or other parameters known to those of skill in the art. In some embodiments, the onset, peak, and duration of the compounds and the dosage administered are based on the subjective experience of the subject, which can be determined by observation, interviewing, or other methods known to those of skill in the art.

In some embodiments, the compounds of a disclosed combination are administered to an individual in a predetermined order. In some embodiments, the compounds of a disclosed combination are administered to an individual at predetermined time points. In some embodiments, the order and time points at which compounds are administered are determined by the subject. In some embodiments, the order and time points at which compounds are administered are determined by the individual administering the compounds. In some embodiments, the order and time points at which compounds are administered are determined before administration. In some embodiments, the order and time points at which compounds are administered are determined after the first, second, and/or third compounds are administered.

Each compound in a disclosed combination has a distinct subjective onset, peak, and duration. Onset refers to the point in time when the subject first begins to feel subjective effects.

In some embodiments, more than one dose of a compound is administered. For example, an individual may opt to consume multiple doses of DMT or ketamine during the administration period. In some embodiments, a compound is not administered. For example, an individual may opt not to consume a benzodiazepine or an NMDA antagonist during the administration period.

In some embodiments, the first compound to be administered to an individual from a disclosed combination is a long-lasting psychedelic. In some embodiments, the second compound to be administered to an individual from a disclosed combination is DMT.

In some embodiments, the first compound to be administered to an individual from a disclosed combination is a benzodiazepine. In some embodiments, the second compound to be administered to an individual from a disclosed combination is long-lasting psychedelic. In some embodiments, the third compound to be administered to an individual from a disclosed combination is DMT.

In some embodiments, the first compound to be administered to an individual from a disclosed combination is a benzodiazepine. In some embodiments, the second compound to be administered to an individual from a disclosed combination is long-lasting psychedelic. In some embodiments, the third compound to be administered to an individual from a disclosed combination is DMT. In some embodiments, the fourth compound to be administered to an individual from a disclosed combination is ketamine.

In some embodiments, the first compound to be administered to an individual from a disclosed combination is a long-lasting psychedelic. In some embodiments, the second compound to be administered to an individual from a disclosed combination is a second long-lasting psychedelic. In some embodiments, the third compound to be administered to an individual from a disclosed combination is DMT.

In some embodiments, the first compound to be administered to an individual from a disclosed combination is a benzodiazepine. In some embodiments, the second compound to be administered to an individual from a disclosed combination is long-lasting psychedelic. In some embodiments, the third compound to be administered to an individual from a disclosed combination is long-lasting psychedelic. In some embodiments, the third compound to be administered to an individual from a disclosed combination is DMT.

In some embodiments, the first compound to be administered to an individual from a disclosed combination is a benzodiazepine. In some embodiments, the second compound to be administered to an individual from a disclosed combination is long-lasting psychedelic. In some embodiments, the third compound to be administered to an individual from a disclosed combination is long-lasting psychedelic. In some embodiments, the third compound to be administered to an individual from a disclosed combination is DMT. In some embodiments, the fourth compound to be administered to an individual from a disclosed combination is ketamine.

In some embodiments, "peak psychedelic effects" refers to intense and profound sensory and cognitive experiences typically associated with a time period within a psychedelic drug experience (e.g., within the administration period of the long-acting psychedelic in embodiments herein), often characterized by altered perceptions, hallucinations, and heightened emotional states. In some embodiments of disclosed methods, the DMT is administered before the peak of a first long-acting psychedelic. In some embodiments, the DMT is administered during the peak of a first long-acting psychedelic. In some embodiments, the DMT is administered after the peak of a first long-acting psychedelic. In some embodiments, a benzodiazepine is administered before the administration of a first long-acting psychedelic. In some embodiments, an NMDA antagonist is taken at a regular interval, such as every hour, after the administration of a first compound. In some embodiments, an NMDA antagonist is taken at a regular interval, such as every hour, after the administration of DMT.

In some embodiments, the method comprises administering a benzodiazepine prior to administering the long-acting psychedelic. In some embodiments, the benzodiazepine is administered about 15 minutes, 30 minutes, 45 minutes, 1 hour, 2 hours, 3 hours, or more than 3 hours before the long-acting psychedelic. In some embodiments, the method comprises administering a benzodiazepine after administering the long-acting psychedelic. In some embodiments, the benzodiazepine is administered about 15 minutes, 30 minutes, 45 minutes, 1 hour, 2 hours, 3 hours, or more than 3 hours after the long-acting psychedelic. In some embodiments, the benzodiazepine is administered simultaneously with the long-acting psychedelic.

In some embodiments, the method comprises administering a benzodiazepine prior to the peak of the effects of the long-acting psychedelic. In some embodiments, the benzodiazepine is administered about 15 minutes, 30 minutes, 45 minutes, 1 hour, 2 hours, 3 hours, or more than 3 hours before the peak of the effects of the long-acting psychedelic. In some embodiments, the method comprises administering a benzodiazepine after administering the long-acting psychedelic. In some embodiments, the benzodiazepine is administered about 15 minutes, 30 minutes, 45 minutes, 1 hour, 2 hours, 3 hours, or more than 3 hours after the peak of the effects of the long-acting psychedelic. In some embodiments, the method comprises administering benzodiazepine before administering the DMT. In some embodiments, the benzodiazepine is administered about 5 minutes, 15 minutes, 30 minutes, 45 minutes, 1 hour, 1.5 hours, 2 hours, 3 hours, or more than 3 hours before administering the DMT. In some embodiments, the benzodiazepine is administered simultaneously with the DMT. In some embodiments, the method comprises administering benzodiazepine after administering the DMT. In some embodiments, the benzodiazepine is administered about 5 minutes, 15 minutes, 30 minutes, 45 minutes, 1 hour, 1.5 hours, 2 hours, 3 hours, or more than 3 hours after administering the DMT.

In some embodiments, the method comprises administering DMT after administering the long-acting psychedelic. In some embodiments, the DMT is administered about 15 minutes, 30 minutes, 45 minutes, 1 hour, 1.5 hours, 2 hours, 3 hours, 4 hours, 4.5 hours, 5 hours, or more than 5 hours after the long-acting psychedelic. In some embodiments, the method comprises administering DMT prior to the peak of the effects of the long-acting psychedelic. In some embodiments, the DMT is administered about 15 minutes, 30 minutes, 45 minutes, 1 hour, 2 hours, 3 hours, or more than 3 hours before the peak of the effects of the long-acting psychedelic. In some embodiments, the method comprises administering DMT after the peak of the effects of the long-acting psychedelic. In some embodiments, the DMT is administered about 15 minutes, 30 minutes, 45 minutes, 1 hour, 2 hours, 3 hours, or more than 3 hours after the peak of the effects of the long-acting psychedelic. In some embodiments, the DMT is administered during the peak of the effects of the long-acting psychedelic.

In some embodiments, the disclosed method comprises multiple administrations of DMT during the administration period of the long-acting tryptamine. In some embodiments, the DMT is administered between 1 and 5 times during the 5 hours following administering to the individual the long-acting psychedelic. In some embodiments, the DMT is administered between 1 and 5 times during the 4 hours following administering to the individual the long-acting psychedelic. In some embodiments, the DMT is administered between 1 and 5 times during the 3 hours following administering to the individual the long-acting psychedelic. In some embodiments, the DMT is administered between 1 and 4 times during the 5 hours following administering to the individual the long-acting psychedelic. In some embodiments, the DMT is administered between 1 and 4 times during the 4 hours following administering to the individual the long-acting psychedelic. In some embodiments, the DMT is administered between 1 and 4 times during the 3 hours following administering to the individual the long-acting psychedelic. In some embodiments, the DMT is administered between 1 and 3 times during the 5 hours following administering to the individual the long-acting psychedelic. In some embodiments, the DMT is administered between 1 and 3 times during the 4 hours following administering to the individual the long-acting psychedelic. In some embodiments, the DMT is administered between 1 and 3 times during the 3 hours following administering to the individual the long-acting psychedelic.

In some embodiments, the method comprises administering ketamine after administering the long-acting psychedelic. In some embodiments, the ketamine is administered about 15 minutes, 30 minutes, 45 minutes, 1 hour, 1.5 hours, 2 hours, 3 hours, 4 hours, 4.5 hours, 5 hours, or more than 5 hours after the long-acting psychedelic. In some embodiments, the method comprises administering ketamine prior to the peak of the effects of the long-acting psychedelic. In some embodiments, the ketamine is administered about 15 minutes, 30 minutes, 45 minutes, 1 hour, 2 hours, 3 hours, or more than 3 hours before the peak of the effects of the long-acting psychedelic. In some embodiments, the method comprises administering the ketamine after the peak of the effects of the long-acting psychedelic. In some embodiments, the ketamine is administered about 15 minutes, 30 minutes, 45 minutes, 1 hour, 2 hours, 3 hours, or more than 3 hours after the peak of the effects of the long-acting psychedelic. In some embodiments, the ketamine is administered during the peak of the effects of the long-acting psychedelic. In some embodiments, the method comprises administering ketamine before administering the DMT. In some embodiments, the ketamine is administered about 5 minutes, 15 minutes, 30 minutes, 45 minutes, 1 hour, 1.5 hours, 2 hours, 3 hours, or more than 3 hours before administering the DMT. In some embodiments, the ketamine is administered no greater than 15 minutes prior to administering the DMT. In some preferred embodiments, the ketamine is administered about 5 minutes, about 10 minutes, or about 15 minutes prior to administering the DMT. In some embodiments, the ketamine is administered simultaneously with the DMT. In some embodiments, the method comprises administering ketamine after administering the DMT. In some embodiments, the ketamine is administered about 5 minutes, 15 minutes, 30 minutes, 45 minutes, 1 hour, 1.5 hours, 2 hours, 3 hours, or more than 3 hours after administering the DMT.

In some embodiments, the disclosed method comprises multiple administrations of ketamine during the administration period of the long-acting tryptamine. In some embodiments, the ketamine is administered between 1 and 5 times during the 5 hours following administering to the individual the long-acting psychedelic. In some embodiments, the ketamine is administered between 1 and 5 times during the 4 hours following administering to the individual the long-acting psychedelic. In some embodiments, the ketamine is administered between 1 and 5 times during the 3 hours following administering to the individual the long-acting psychedelic. In some embodiments, the ketamine is administered between 1 and 4 times during the 5 hours following administering to the individual the long-acting psychedelic. In some embodiments, the ketamine is administered between 1 and 4 times during the 4 hours following administering to the individual the long-acting psychedelic. In some embodiments, the ketamine is administered between 1 and 4 times during the 3 hours following administering to the individual the long-acting psychedelic. In some embodiments, the ketamine is administered between 1 and 3 times during the 5 hours following administering to the individual the long-acting psychedelic. In some embodiments, the ketamine is administered between 1 and 3 times during the 4 hours following administering to the individual the long-acting psychedelic. In some embodiments, the ketamine is administered between 1 and 3 times during the 3 hours following administering to the individual the long-acting psychedelic.

In some embodiments, wherein a disclosed method comprises administering a MAOI, the MAOI is administered before administering the long-acting psychedelic. In some embodiments, the MAOI is administered about 15 minutes, 30 minutes, 45 minutes, 1 hour, 1.5 hours, 2 hours, 3 hours, or more than 3 hours before administering the long-acting psychedelic. In some embodiments, the MAOI is administered after administering the long-acting psychedelic. In some embodiments, the MAOI is administered about 15 minutes, 30 minutes, 45 minutes, 1 hour, 1.5 hours, 2 hours, 3 hours, 3.5 hours, 4 hours, 4.5 hours, 5 hours, or more than 5 hours after administering the long-acting psychedelic In some embodiments, the method comprises administering the MAOI prior to the peak of the effects of the long-acting psychedelic. In some embodiments, the MAOI is administered about 15 minutes, 30 minutes, 45 minutes, 1 hour, 2 hours, 3 hours, or more than 3 hours before the peak of the effects of the long-acting psychedelic. In some embodiments, the MAOI is administered before administering the DMT. In some embodiments, the MAOI is administered about 5 minutes, 15 minutes, 30 minutes, 45 minutes, 1 hour, 1.5 hours, 2 hours, 3 hours, or more than 3 hours before administering the DMT. In some embodiments, the MAOI is administered simultaneously with the DMT. In some embodiments, the MAOI is administered after administering the DMT. In some embodiments, the MAOI is administered about 5 minutes, 15 minutes, 30 minutes, 45 minutes, 1 hour, 1.5 hours, 2 hours, 3 hours, or more than 3 hours after administering the DMT. In some embodiments, the MAOI is administered simultaneously with the ketamine.

G. COMPOSITIONS

The individual compounds of the disclosed methods will be understood to also encompass pharmaceutically acceptable salts of such compounds. The term "pharmaceutically acceptable salt" refers to salts prepared from pharmaceutically acceptable non-toxic acids or bases, and which may be synthesized by conventional chemical methods. Generally, such salts are prepared by reacting the free acid or base forms of these agents with a stoichiometric amount of the appropriate base or acid in water or in an organic solvent, or in a mixture of the two; generally, nonaqueous media (e.g., ether, ethyl acetate, ethanol, isopropanol, or acetonitrile) are preferred. For therapeutic use, salts of the compounds are those wherein the counter-ion is pharmaceutically acceptable. Exemplary salts include 2-hydroxyethanesulfonate, 2-naphthalenesulfonate, 2-napsylate, 3-hydroxy-2-naphthoate, 3-phenylpropionate, 4-acetamidobenzoate, acefyllinate, acetate, aceturate, adipate, alginate, aminosalicylate, ammonium, amsonate, ascorbate, aspartate, benzenesulfonate, benzoate, besylate, bicarbonate, bisulfate, bitartrate, borate, butyrate, calcium edetate, calcium, camphocarbonate, camphorate, camphorsulfonate, camsylate, carbonate, cholate, citrate, clavulariate, cyclopentanepropionate, cypionate, d-aspartate, d-camsylate, d-lactate, decanoate, dichloroacetate, digluconate, dodecylsulfate, edentate, edetate, edisylate, estolate, esylate, ethanesulfonate, ethyl sulfate, fumarate, furate, fusidate, galactarate (mucate), galacturonate, gallate, gentisate, gluceptate, glucoheptanoate, gluconate, glucuronate, glutamate, glutarate, glycerophosphate, glycolate, glycollylarsanilate, hemisulfate, heptanoate (enanthate), heptanoate, hexafluorophosphate, hexanoate, hexylresorcinate, hippurate, hybenzate, hydrabamine, hydrobromide, hydrobromide/bromide, hydrochloride, hydroiodide, hydroxide, hydroxybenzoate, hydroxynaphthoate, iodide, isethionate, isothionate, 1-aspartate, 1-camsylate, 1-lactate, lactate, lactobionate, laurate, laurylsulphonate, lithium, magnesium, malate, maleate, malonate, mandelate, meso-tartrate, mesylate, methanesulfonate, methylbromide, methylnitrate, methylsulfate, mucate, myristate, N-methylglucamine ammonium salt, napadisilate, naphthylate, napsylate, nicotinate, nitrate, octanoate, oleate, orotate, oxalate, p-toluenesulfonate, palmitate, pamoate, pantothenate, pectinate, persulfate, phenylpropionate, phosphate, phosphateldiphosphate, picrate, pivalate, polygalacturonate, potassium, propionate, pyrophosphate, saccharate, salicylate, salicylsulfate, sodium, stearate, subacetate, succinate, sulfate, sulfosaliculate, sulfosalicylate, suramate, tannate, tartrate, teoclate, terephthalate, thiocyanate, thiosalicylate, tosylate, tribrophenate, triethiodide, undecanoate, undecylenate, valerate, valproate, xinafoate, zinc and the like. Exemplary salts also include those in, for example, Berge et al. J. Pharm. Sci. 1977; 66:1-19.

In some embodiments, compounds used in a disclosed method may be administered to an individual as a pharmaceutical composition or multiple pharmaceutical compositions. Such pharmaceutical compositions can be formulated into any suitable dosage form, such as aqueous oral dispersions, aqueous oral suspensions, solid dosage forms including oral solid dosage forms, aerosols, controlled release formulations, fast melt formulations, effervescent formulations, self-emulsifying dispersions, solid solutions, liposomal dispersions, lyophilised formulations, tablets, capsules, pills, powders, pulsatile release formulations, multiparticulate formulations, immediate release, controlled release, sustained release, extended release, and modified release formulations, and mixed immediate release and controlled release formulations.

The pharmaceutical composition or multiple pharmaceutical compositions may be administered to the subject using any convenient administration protocol capable of resulting in the desired activity. In some embodiments, the pharmaceutical composition or multiple pharmaceutical compositions can be incorporated into a variety of formulations, e.g., pharmaceutically acceptable vehicles, for therapeutic administration. For example, in some embodiments, the active agents of the present disclosure can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments (e.g., skin creams), solutions, suppositories, injections, inhalants and aerosols.

As such, administration of the active agents can be achieved in various ways, for example, oral, buccal, rectal, parenteral, intraperitoneal, intradermal, transdermal, intracheal, intravenous, or intramuscular, administration, including combinations thereof.

H. KITS

Another aspect of the disclosure provides kits containing any of the disclosed active agents (e.g., any of the long-acting psychedelics, DMT, benzodiazepines, and NMDA antagonists) or compositions or formulations thereof, along with suggested administration guidelines, and a suitable container. Individual unit dosage forms can be included in multi-dose kits or containers. Compositions or formulations also can be packaged in single or multiple unit dosage forms for uniformity of dosage and ease of administration.

Kits generally comprise suitable packaging. The kits may comprise one or more containers comprising any compound or composition described herein. Each component (if there is more than one component) can be packaged in separate containers or some components can be combined in one container where cross-reactivity and shelf life permit. The kits may be in unit dosage forms, bulk packages (e.g., multi-dose packages) or sub-unit doses. For example, kits may be provided that contain sufficient dosages of a compound or composition as disclosed herein and/or an additional active agents useful for disclosed method to provide effective quantities for an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the compounds or compositions and instructions for use and be packaged in quantities sufficient for storage and use in both medical (e.g., hospitals, pharmacies) and non-medical (e.g., service centers, retreat centers) settings.

Information pertaining to dosing and proper administration (if needed) can be printed onto a kit directly (e.g., on a blister pack or other interior packaging holding the compounds or compositions); however, kits can further contain package inserts and other printed instructions (e.g., on exterior packaging) for administering disclosed compounds and compositions and for their appropriate use.

In some embodiments, wherein a disclosed method comprises administering multiple doses of a compound (e.g., DMT, ketamine) to the individual during a single session, the kit may include multiple discrete doses of the compound, or may include the compound as a single total quantity along with information (e.g., printed instructions for use or electronic instructions for use) for dividing the quantity into individual doses.

I. Applications of Disclosed Methods
a. Improving the DMT Experience

In some aspects, a disclosed method modulates the subjective effects of the DMT experience. In some embodiments, a disclosed method is useful for improving the DMT experience. In some embodiments, the improvements to the DMT experience are assessed relative to the experience of administering DMT alone (i.e., without co-administering another drug).

In some embodiments, improving the DMT experience comprises reduced feelings of a challenging experience, e.g., reducing feelings of grief, fear, death, insanity, isolation, physical distress, and paranoia. In some embodiments, improving the DMT experience comprises enhancing feelings of a mystical experience, e.g., feelings of internal unity, external unity, transcendence of time and space, ineffability and paradoxicality, a sense of sacredness, noetic quality, and a deeply-felt positive mood. Other improvements in subjective effects may be noted and assessed by one of skill in the art. Such improvements can facilitate repeated administration of DMT, which may prolong enhanced subjective effects.

In some embodiments, a disclosed method reduces or eliminates undesirable psychological effects of DMT in an individual including, but not limited to, any of disorientation, acute anxiety, and emotional distress. In some embodiments, a disclosed method reduces or eliminates undesirable physical effects in a user including, but not limited to, any of diarrhea, nausea, vomiting, elevated heart rate, and elevated blood pressure.

In some embodiments, an individual who has a DMT experience according to a disclosed method experiences less anxiety, as compared to administering DMT alone. In some embodiments, an individual who has a DMT experience according to a disclosed method experiences more euphoria, as compared to administering DMT alone. In some embodiments, an individual who has a DMT experience according to a disclosed method experiences less intensity, as compared to administering DMT alone. In some embodiments, an individual who has a DMT experience according to a disclosed method experiences a greater sense of control, as compared to administering DMT alone. In some embodiments, an individual who has a DMT experience according to a disclosed method experiences an improved capability to keep their eyes open, as compared to administering DMT alone.

In some embodiments, DMT administered according to a disclosed method has an increased duration of a subjective effect of DMT, compared to the duration of intravenous, intramuscular, or inhaled DMT alone. In some embodiments, the duration of a subjective effect of DMT is increased by at least 1.2-fold, 1.5-fold, 1.7-fold, 2-fold, or 5-fold. For example, in some embodiments, the duration of visual hallucinations associated with DMT is increased by at least 1.2-fold, 1.5-fold, 1.7-fold, 2-fold, or 5-fold, when the DMT is administered according to a disclosed method, as compared to the duration of visual hallucinations when intravenous, intramuscular, or inhaled DMT is administered alone.

In some embodiments, an individual who has a DMT experience according to a disclosed method, wherein the long-acting tryptamine is psilacetin, the subject experiences less anxiety, as compared to administering DMT and psilocybin and/or psilocin. In some embodiments, an individual who has a DMT experience according to a disclosed method, wherein the long-acting tryptamine is psilacetin, experiences more euphoria, as compared to administering DMT and psilocybin and/or psilocin. In some embodiments, an individual who has a DMT experience according to a disclosed method, wherein the long-acting tryptamine is psilacetin, experiences less intensity, as compared to administering DMT and psilocybin and/or psilocin. In some embodiments, an individual who has a DMT experience according to a disclosed method, wherein the long-acting tryptamine is psilacetin, experiences a greater sense of control, as compared to administering DMT and psilocybin and/or psilocin. In some embodiments, an individual who has a DMT experience according to a disclosed method, wherein the long-acting tryptamine is psilacetin, experiences an improved capability to keep their eyes open, as compared to administering DMT and psilocybin and/or psilocin. In some embodiments, administering DMT and psilacetin provides an improved subjective experience, as compared to a similar method, wherein the method comprises administering DMT and psilocybin and/or psilocin.

In some embodiments, wherein a disclosed method comprises administering to an individual a benzodiazepine in combination with a long-acting tryptamine and DMT (and optionally ketamine), the benzodiazepine can reduce the subject's anxiety and/or discomfort. In some embodiments, the reduction of the subject's anxiety and/or discomfort takes place during the onset of the physical or psychological effects of the long-acting tryptamine. In some embodiments, the reduction of the subject's anxiety and/or discomfort takes place during the peak of the physical or psychological effects of the long-acting tryptamine.

In some embodiments, wherein a disclosed method comprises administering to an individual ketamine in combination with a long-acting tryptamine and DMT (and optionally a benzodiazepine), the ketamine can alter the experience of the DMT experience to add a perceived "warmth" or "brightness" to the experience. In some embodiments, administering ketamine according to a disclosed method increases the euphoria associated with the DMT experience. In some embodiments, administering ketamine according to a disclosed method creates a dissociative effect in the subject, which can improve the overall experience of the DMT experience.

Measures of effect includes any outcome measure, endpoint, effect measure, or measure of effect which is used to assess the effect, both positive and negative, of a method, whether reported by the individual (e.g., questionnaires), based on other individual data (e.g., data monitoring), gathered through laboratory tests such as blood work, urine samples, etc., through examination by a medical or health professional or facilitator, or by digital tools or means, e.g., electronic tools such as online tools, smartphones, wireless devices, biosensors, or health apps.

In some embodiments, measuring the improvement in the DMT experience will include an assessment. "Assessment" refers to any means or method used with an individual, whether before, during, after, or unrelated in time to a specific treatment protocol, to measure, estimate, or evaluate a nature, ability, symptom, disorder, or other characteristic of the individual, whether qualitatively or quantitatively, and whether performed by a facilitator (e.g., an interview), by the individual his or herself (e.g., a self-reported questionnaire), by a third-party or by a computer, including a device (e.g., a medical sensor or biosensor, a watch or fitness tracker, or a "wearable"), and whether graded by a human decision-maker or an artificial intelligence, machine learning, or computer algorithm.

An assessment may be computer-assisted, and other computer-assisted assessments may be performed besides the assessments above. The term "computer-assisted" in "computer-assisted assessment" means an assessment comprising the use of electronic tools such as online tools, smartphones, wireless devices, or health apps (in some such examples, also known as "digital phenotyping"). Computer-assisted assessment will include the use of an electronic psychiatric notes system, where relevant clinical information will be recorded for the duration of the therapy by a therapist interacting face-to-face with an individual, and will also include the use of computer systems where the therapist and patient interact virtually (either synchronously or asynchronously), as well as where an individual only interacts with a computer ("computer" broadly meaning any electronic tool suitable for such purposes, including desktop, laptop, and notebook computers; tablets, smartphones, and other mobile devices; watches, fitness trackers, and personal electronic devices; and the like).

In some embodiments, an improvement of the DMT experience is measured by an increase in the score of any of the Mystical, Positive Mood, Transcendence of Time and Space, and Ineffability subscales of the 30-item revised Mystical Experience Questionnaire (MEQ30). The MEQ30 is considered to be an efficient measure of individual mystical experiences, and may be positively predictive of persisting change in attitudes, behavior, and well-being attributed to psychedelic experiences (Barrett et al. J Psychopharmacol. 2015; 29(11):1182-1190.).

In some embodiments, an individual administered DMT according to a disclosed method has a score on the Mystical subscale of at least 10, at least 15, at least 20, at least 25, at least 30, at least 35, at least 40, at least 45, at least 50, at least 55, at least 60, at least 65, at least 70, or 75. In some embodiments, an individual administered DMT according to a disclosed method has a score on the Mystical subscale of at least 40, at least 45, at least 50, at least 55, at least 60, at least 65, at least 70, or greater than 70. In some embodiments, an individual administered DMT according to a disclosed method has a score on the Mystical subscale of at least 50. In some embodiments, an individual administered DMT according to a disclosed method has a score on the Mystical subscale of at least 55. In some embodiments, an individual administered DMT according to a disclosed method has a score on the Mystical subscale of at least 60. In some embodiments, an individual administered DMT according to a disclosed method has a score on the Mystical subscale of at least 65. In some embodiments, an individual administered DMT according to a disclosed method has a score on the Mystical subscale of at least 70. In some embodiments, an individual administered DMT according to a disclosed method has a score on the Mystical subscale of 75.

In some embodiments, an individual administered DMT according to a disclosed method has a score on the Positive Mood subscale of at least 10, at least 15, at least 20, at least 25, or 30. In some embodiments, an individual administered DMT according to a disclosed method has a score on the Positive Mood subscale of at least 20, at least 21, at least 22, at least 23, at least 24, at least 25, at least 26, at least 27, at least 28, at least 29, or 30. In some embodiments, an individual administered DMT according to a disclosed method has a score on the Positive Mood subscale of at least 20. In some embodiments, an individual administered DMT according to a disclosed method has a score on the Positive Mood subscale of at least 21. In some embodiments, an individual administered DMT according to a disclosed method has a score on the Positive Mood subscale of at least 22. In some embodiments, an individual administered DMT according to a disclosed method has a score on the Positive Mood subscale of at least 23. In some embodiments, an individual administered DMT according to a disclosed method has a score on the Positive Mood subscale of at least 24. In some embodiments, an individual administered DMT according to a disclosed method has a score on the Positive Mood subscale of at least 25. In some embodiments, an individual administered DMT according to a disclosed method has a score on the Positive Mood subscale of at least 26. In some embodiments, an individual administered DMT according to a disclosed method has a score on the Positive Mood subscale of at least 27. In some embodiments, an individual administered DMT according to a disclosed method has a score on the Positive Mood subscale of at least 28. In some embodiments, an individual administered DMT according to a disclosed method has a score on the Positive Mood subscale of at least 29. In embodiments, an individual administered DMT according to a disclosed method has a score on the Positive Mood subscale of 30.

In some embodiments, an individual administered DMT according to a disclosed method has a score on the Transcendence of Time and Space subscale of at least 5, at least 10, at least 15, at least 20, at least 25, or greater than 25. In some embodiments, an individual administered DMT according to a disclosed method has a score on the Transcendence of Time and Space subscale of at least 15, at least 20, at least 25, or greater than 25. In some embodiments, an individual administered DMT according to a disclosed method has a score on the Transcendence of Time and Space subscale of at least 15. In some embodiments, an individual administered DMT according to a disclosed method has a score on the Transcendence of Time and Space subscale of at least 20. In some embodiments, an individual administered DMT according to a disclosed method has a score on the Transcendence of Time and Space subscale of at least 25. In some embodiments, an individual administered DMT according to a disclosed method has a score on the Transcendence of Time and Space subscale of 30.

In some embodiments, an individual administered DMT according to a disclosed method has a score on the Ineffability subscale of at least 5, at least 6, at least 7, at least 8, at least 9, at least 10, at least 11, at least 12, at least 13, at least 14, or 15. In some embodiments, an individual administered DMT according to a disclosed method has a score on the Ineffability subscale of at least 9, at least 10, at least 11, at least 12, at least 13, at least 14, or 15. In some embodiments, an individual administered DMT according to a disclosed method has a score on the Ineffability subscale of at least 9. In some embodiments, an individual administered DMT according to a disclosed method has a score on the Ineffability subscale of at least 10. In some embodiments, an individual administered DMT according to a disclosed method has a score on the Ineffability subscale of at least 11. In some embodiments, an individual administered DMT according to a disclosed method has a score on the Ineffability subscale of at least 12. In some embodiments, an individual administered DMT according to a disclosed method has a score on the Ineffability subscale of at least 13. In some embodiments, an individual administered DMT according to a disclosed method has a score on the Ineffability subscale of at least 14. In some embodiments, an individual administered DMT according to a disclosed method has a score on the Ineffability subscale of 15.

In some embodiments, the score of any of the Mystical, Positive Mood, Transcendence of Time and Space, and Ineffability subscales for an individual administered DMT according to a disclosed method is at least 50% of the maximum possible score. In some embodiments, the score of any of the Mystical, Positive Mood, Transcendence of Time and Space, and Ineffability subscales for an individual administered DMT according to a disclosed method is at least 55% of the maximum possible score. In some embodiments, the score of any of the Mystical, Positive Mood, Transcendence of Time and Space, and Ineffability subscales for an individual administered DMT according to a disclosed method is at least 60% of the maximum possible score. In some embodiments, the score of any of the Mystical, Positive Mood, Transcendence of Time and Space, and Ineffability subscales for an individual administered DMT according to a disclosed method is at least 75% of the maximum possible score. In some embodiments, the score of all of the Mystical, Positive Mood, Transcendence of Time and Space, and Ineffability subscales for an individual administered DMT according to a disclosed method is at least 60% of the maximum possible score. In some embodiments, the score of any of the Mystical, Positive Mood, Transcendence of Time and Space, and Ineffability subscales for an individual administered DMT according to a disclosed method is at least 75% of the maximum possible score.

In some embodiments, an individual administered DMT according to a disclosed method scores at least 60% of the maximum score in all MEQ30 dimensions (e.g., Mysticism, Positive Mood, Transcendence, and Ineffability), indicating a "mystical-type experience." In some embodiments, an individual administered DMT according to a disclosed method scores at least 65% of the maximum score in all MEQ30 dimensions (e.g., Mysticism, Positive Mood, Transcendence, and Ineffability), indicating a "mystical-type experience." In some embodiments, an individual administered DMT according to a disclosed method scores at least 70% of the maximum score in all MEQ30 dimensions (e.g., Mysticism, Positive Mood, Transcendence, and Ineffability), indicating a "mystical-type experience." In some embodiments, an individual administered DMT according to a disclosed method scores at least 75% of the maximum score in all MEQ30 dimensions (e.g., Mysticism, Positive Mood, Transcendence, and Ineffability), indicating a "mystical-type experience." In some embodiments, an individual administered DMT according to a disclosed method scores at least 80% of the maximum score in all MEQ30 dimensions (e.g., Mysticism, Positive Mood, Transcendence, and Ineffability), indicating a "mystical-type experience."

In some embodiments, an improvement of the DMT experience is measured by a decrease in the score of any of the Fear, Grief, Physical Distress, Insanity, Isolation, Death, and Paranoia subscales of the Challenging Experience Questionnaire (CEQ). The CEQ is a validated research tool used to evaluate acute adverse psychological reactions that occur during a psychedelic experience (Barrett et al. J. Psychopharmacol. 2016; 30(12):1279-1295).

In some embodiments, an individual administered DMT according to a disclosed method has a score on any of the Fear, Grief, Physical Distress, Insanity, Isolation, Death, and Paranoia subscales that is less than 30%, 20%, 15%, 10%, 9%, 8%, 7%, 6%, 5%, 4%, 3%, 2%, or 1% of the maximum score for the subscale. In some embodiments, an individual administered DMT according to a disclosed method has a score on any of the Fear, Grief, Physical Distress, Insanity, Isolation, Death, and Paranoia subscales that is less than 10%, 9%, 8%, 7%, 6%, 5%, 4%, 3%, 2%, or 1% of the maximum score for the subscale. In some embodiments, an individual administered DMT according to a disclosed method has a score on all of the Fear, Grief, Physical Distress, Insanity, Isolation, Death, and Paranoia subscales that is less than 30%, 20%, 15%, 10%, 9%, 8%, 7%, 6%, 5%, 4%, 3%, 2%, or 1% of the maximum score for the subscale. In some embodiments, an individual administered DMT according to a disclosed method has a score on all of the Fear, Grief, Physical Distress, Insanity, Isolation, Death, and Paranoia subscales that is less than 10%, 9%, 8%, 7%, 6%, 5%, 4%, 3%, 2%, or 1% of the maximum score for the subscale.

In some embodiments, an individual administered DMT according to a disclosed method has a score on the CEQ Fear subscale of less than 10% of the maximum value for the subscale. In some embodiments, an individual administered DMT according to a disclosed method has a score on the CEQ Grief subscale of less than 10% of the maximum value for the subscale. In some embodiments, an individual administered DMT according to a disclosed method has a score on the CEQ Physical Distress subscale of less than 10% of the maximum value for the subscale. In some embodiments, an individual administered DMT according to a disclosed method has a score on the CEQ Insanity subscale of less than 10% of the maximum value for the subscale. In some embodiments, an individual administered DMT according to a disclosed method has a score on the CEQ Isolation subscale of less than 10% of the maximum value for the subscale. In some embodiments, an individual administered DMT according to a disclosed method has a score on the CEQ Death subscale of less than 10% of the maximum value for the subscale. In some embodiments, an individual administered DMT according to a disclosed method has a score on the CEQ Paranoia subscale of less than 10% of the maximum value for the subscale.

In some embodiments, an individual administered DMT according to a disclosed method has a score on the CEQ Fear subscale of less than 6, less than 5, less than 4, less than 3, less than 2, or less than 1. In some embodiments, an individual administered DMT according to a disclosed method has a score on the Fear subscale of less than 3, less than 2, or less than 1.

In some embodiments, an individual administered DMT according to a disclosed method has a score on the CEQ Grief subscale of less than 13, less than 12, less than 10, less than 9, less than 8, less than 7, less than 6, less than 5, less than 4, less than 3, less than 2, or less than 1. In some embodiments, an individual administered DMT according to a disclosed method has a score on the Grief subscale of less than 6, less than 5, less than 4, less than 3, less than 2, or less than 1.

In some embodiments, an individual administered DMT according to a disclosed method has a score on the CEQ Physical Distress subscale of less than 6, less than 5, less than 4, less than 3, less than 2, or less than 1. In some embodiments, an individual administered DMT according to a disclosed method has a score on the Physical Distress subscale of less than 2 or less than 1.

In some embodiments, an individual administered DMT according to a disclosed method has a score on the CEQ Insanity subscale of less than 4, less than 3, less than 2, or less than 1. In some embodiments, an individual administered DMT according to a disclosed method has a score on the Insanity subscale of less than 3, less than 2, or less than 1.

In some embodiments, an individual administered DMT according to a disclosed method has a score on the CEQ Isolation subscale of less than 5, less than 4, less than 3, less than 2, or less than 1. In some embodiments, an individual administered DMT according to a disclosed method has a score on the Isolation subscale of less than 2 or less than 1.

In some embodiments, an individual administered DMT according to a disclosed method has a score on the CEQ Death subscale of less than 3, less than 2, or less than 1. In some embodiments, an individual administered DMT according to a disclosed method has a score on the Death subscale of less than 2 or less than 1.

In some embodiments, an individual administered DMT according to a disclosed method has a score on the CEQ Paranoia subscale of less than 3, less than 2, or less than 1. In some embodiments, an individual administered DMT according to a disclosed method has a score on the Paranoia subscale of less than 2 or less than 1.

In some embodiments, an individual administered DMT according to a disclosed method has an increased score on the MEQ30 Mysticism subscale compared to an individual administered DMT alone. In some embodiments, an individual administered DMT according to a disclosed method has a score on the Mysticism subscale that is at least 1 point, 5 points, 10 points, 15 points, 20 points, 25 points, 30 points, 35 points, 40 points, 45 points, or 50 points higher than the score of an individual administered DMT alone.

In some embodiments, an individual administered DMT according to a disclosed method has an increased score on the MEQ30 Positive Mood subscale compared to an individual administered DMT alone. In some embodiments, an individual administered DMT according to a disclosed method has a score on the Positive Mood subscale that is at least 1 point, 5 points, 10 points, 15 points, or 20 points points higher than the score of an individual administered DMT alone.

In some embodiments, an individual administered DMT according to a disclosed method has an increased score on the MEQ30 Transcendence subscale compared to an individual administered DMT alone. In some embodiments, an individual administered DMT according to a disclosed method has a score on the Transcendence subscale that is at least 1 point, 5 points, 10 points, 15 points, or 20 points higher than the score of an individual administered DMT alone.

In some embodiments, an individual administered DMT according to a disclosed method has an increased score on the MEQ30 Ineffability subscale compared to an individual administered DMT alone. In some embodiments, an individual administered DMT according to a disclosed method has a score on the Ineffability subscale that is at least 1 point, 2 points, 3 points, 4 points, 5 points, 6 points, 7 points, 8 points, 9 points, or 10 points higher than the score of an individual administered DMT alone.

In some embodiments, an individual administered DMT according to a disclosed method has a decreased score on the CEQ Fear subscale compared to an individual administered DMT alone. In some embodiments, an individual administered DMT according to a disclosed method has a score on the Fear subscale that is 1 point, 2 points, 3 points, 4 points, or more than 4 points lower than the score of an individual administered DMT alone.

In some embodiments, an individual administered DMT according to a disclosed method has a decreased score on the CEQ Grief subscale compared to an individual administered DMT alone. In some embodiments, an individual administered DMT according to a disclosed method has a score on the Grief subscale that is 1 point, 2 points, 3 points, 4 points, 5 points, 6 points, 7 points, 8 points, 9 points, 10 points, 11 points, or more than 11 points lower than the score of an individual administered DMT alone.

In some embodiments, an individual administered DMT according to a disclosed method has a decreased score on the CEQ Physical Distress subscale compared to an individual administered DMT alone. In some embodiments, an individual administered DMT according to a disclosed method has a score on the Physical Distress subscale that is 1 point, 2 points, 3 points, 4 points, or more than 4 points lower than the score of an individual administered DMT alone.

In some embodiments, an individual administered DMT according to a disclosed method has a decreased score on the CEQ Insanity subscale compared to an individual administered DMT alone. In some embodiments, an individual administered DMT according to a disclosed method has a score on the Insanity subscale that is 1 point, 2 points, 3 points, or more than 3 points lower than the score of an individual administered DMT alone.

In some embodiments, an individual administered DMT according to a disclosed method has a decreased score on the CEQ Isolation subscale compared to an individual administered DMT alone. In some embodiments, an individual administered DMT according to a disclosed method has a score on the Isolation subscale that is 1 point, 2 points, 3 points, 4 points, or more than 4 points lower than the score of an individual administered DMT alone.

In some embodiments, an individual administered DMT according to a disclosed method has a decreased score on the CEQ Death subscale compared to an individual administered DMT alone. In some embodiments, an individual administered DMT according to a disclosed method has a score on the Death subscale that is 1 point, 2 points, or more than 2 points lower than the score of an individual administered DMT alone.

In some embodiments, an individual administered DMT according to a disclosed method has a decreased score on the CEQ Paranoia subscale compared to an individual administered DMT alone. In some embodiments, an individual administered DMT according to a disclosed method has a score on the Paranoia subscale that is 1 point, 2 points, or more than 2 points lower than the score of an individual administered DMT alone.

b. Treating Disorders and Improving Health and Overall Wellbeing

In some aspects, a disclosed method is useful for improving the health and/or overall wellbeing of an individual. In some embodiments, the subject can be a person who suffers from a specific disease or disorder that negatively influences their quality of life. In some embodiments, the disease or disorder has been diagnosed by a medical professional. In other embodiments, the subject may individually and independently seek a therapeutic remedy for symptoms they are experiencing, whether or not these symptoms are associated with a specific, diagnosed medical condition. In other embodiments, the subject can also be a healthy person who does not suffer from such a disease or disorder (i.e., a person who does not experience symptoms associated with a diagnosed medical condition).

In some embodiments, improving the health and/or overall wellbeing of an individual refers to treating a healthy subject (a "healthy normal"; i.e., a disclosed method can be used for the betterment of the well). In some embodiments, improving the health and/or overall wellbeing of an individual refers to treating an individual having a disease or disorder, such as a diagnosed disease or disorder, or a disease or disorder which is treated by the practice of a disclosed method.

In some embodiments, disclosed methods are useful in the treatment of a disease or disorder. In some embodiments, "treating" or "treatment" refers to treating a disease or disorder in a mammal, and preferably in a human, and includes causing a desired biological or pharmacological effect, such as: (a) preventing a disorder from occurring in an individual who may be predisposed to the disorder but has not yet been diagnosed with it; (b) inhibiting a disorder, i.e., arresting its development; (c) relieving a disorder, i.e., causing regression thereof; (d) protecting from or relieving a symptom or pathology caused by or related to a disorder; (e) reducing, decreasing, inhibiting, ameliorating, or preventing the onset, severity, duration, progression, frequency or probability of one or more symptoms or pathologies associated with a disorder; and (f) preventing or inhibiting of a worsening or progression of symptoms or pathologies associated with a disorder or comorbid with a disorder. Other such measurements, benefits, and surrogate or clinical endpoints, alone or in combination, will be understood to one of ordinary skill based on the teachings herein and the knowledge in the art.

In some embodiments, the disease or disorder is a mental health disorder. In some embodiments, a disclosed method treats the mental health disorder. In general, mental health disorders are characterized by clinically significant disturbances in an individual's cognition, emotion, behavior, or a combination thereof, resulting in impaired functioning, distress, or increased risk of suffering. Although the terms "mental disorder" and "mental health disorder," as well as terms that define specific diseases and disorders, generally shall refer to the criteria in the ICD-11, or a patient with a diagnosis based thereon, it will be appreciated that disclosed methods are equally applicable to patients having an equivalent underlying disorder, whether that disorder is diagnosed based on the criteria in ICD-11, ICD-10, DSM-5, or DSM-IV (each of which is incorporated by reference herein in its entirety) whether the diagnosis is based on other clinically acceptable criteria, or whether the patient has not yet had a formal clinical diagnosis.

In some embodiments, the disease or disorder is a neurodegenerative disorder. In some embodiments, a disclosed method treats the neurodegenerative disorder. In some embodiments, the neurodegenerative disorder is any of Alzheimer's disease (AD), corticobasal degeneration (CBD), a form of dementia, Huntington's disease, Lytico-Bodig disease, mild cognitive impairment (MCI), a motor neuron disease, progressive supranuclear palsy (PSP), multiple sclerosis, Parkinson's disease, and traumatic brain injury (TBI). In some embodiments, the form of dementia is any of frontotemporal dementia (FTD), Lewy body dementia, tangle-predominant senile dementia, Pick's disease (PiD), argyrophilic grain disease, Guam parkinsonism-dementia complex, frontotemporal dementia with parkinsonism-17 (FTDP-17), and vascular dementia. In some embodiments, the motor neuron disease is any of amyotrophic lateral sclerosis (ALS), progressive bulbar palsy (PBP), pseudobulbar palsy, progressive muscular atrophy (PMA), primary lateral sclerosis (PLS), spinal muscular atrophy (SMA) and monomelic amyotrophy (MMA). In some embodiments, the disease or disorder is stroke.

In some embodiments, improving the health and/or overall wellbeing of an individual refers to improving the therapeutic effects or therapeutic efficacy of psychedelic-assisted therapy. "Therapeutic effect" or "therapeutic efficacy" means the responses(s) in a mammal, and preferably a human, after treatment that are judged to be desirable and beneficial. Depending on the disorder to be treated, or improvement in mental health or functioning sought, and depending on the therapeutic substance administered, those responses may therefore differ, but would be readily understood by those of ordinary skill. Measures of therapeutic effect includes any outcome measure, endpoint, effect measure, or measure of effect within clinical or medical practice or research which is used to assess the effect, both positive and negative, of an intervention or treatment, whether patient-reported (e.g., questionnaires), based on other patient data (e.g., patient monitoring), gathered through laboratory tests such as blood work, urine samples, etc., through medical examination by a doctor or other medical professional, or by digital tools or means, e.g., electronic tools such as online tools, smartphones, wireless devices, biosensors, or health apps.

In some embodiments, a disclosed method is useful for improving the overall wellbeing of an individual. "Wellbeing" refers to a positive state of health or comfort, e.g., relative to a reference population. As used herein "mental wellbeing" refers to a positive mental state, relative to a reference population. For example, in an individual experiencing depression (whether or not medically diagnosed, or rising to the level of a clinical diagnosis), low self-esteem, addiction, compulsion, or anxiety may experience an improvement in mental wellbeing in response to therapy aimed at improving mood, self-esteem, addiction, compulsion, or anxiety, respectively. As used herein, "physical wellbeing" refers to one or more positive aspects of an individual's physical health. For example, an improvement of physical wellbeing includes alleviation of somatic symptoms associated with a psychological disorder, depression, addiction, compulsion, anxiety, or sexual dysfunction. Such symptoms include, for example, chronic pain, pain disorder, relational disorder, body dysmorphia, conversion (e.g., loss of bodily function due to anxiety), hysteria, neurological conditions without identifiable cause, or psychosomatic illness).

In some embodiments, where a disclosed method is useful for improving the overall wellbeing of an individual, the disclosed method decreases depression, decreases a symptom of depression or of a depressive disorder (e.g., major depressive disorder (MDD), treatment-resistant depression (TRD), atypical depression, postpartum depression, catatonic depression, premenstrual dysphoric disorder, a depressive disorder due to a medical condition, or the like), or provides an antidepressant effect. In some embodiments, the disclosed method decreases depression, decreases a symptom of depression or of a depressive disorder, or provides an antidepressant effect that is greater than a comparator treatment, such as a known pharmacotherapy (e.g., an SSRI, SNRI, TCA, MAOI, or the like), a known intervention (e.g., EMDR, psychotherapy, a specific psychotherapy such as CBT or ACT), another psychedelic or entactogen, or a combination of any of the foregoing. In some embodiments, a decrease in depression, decrease in a symptom of depression or of a depressive disorder, or increase in an antidepressant effect may be a synergistic effect. Other advantages may be demonstrated over such a comparator, such as disclosed herein or known in view of this disclosure to one of skill.

A comparator also may be a drug combination having less than all of the drugs of a disclosed combination. For example, a comparator for a combination of a long-acting tryptamine, DMT, and a benzodiazepine, may be only one or two of such agents. A comparator for a combination of a long-acting tryptamine, DMT, a benzodiazepine, and ketamine, may be only one, two, or three of such agents. For example, a combination of psilocybin, DMT, and lorazepam may be just psilocybin and lorazepam. A combination of psilacetin, DMT, and lorazepam also may be just psilocybin and lorazepam, as it will be understood that comparator combinations may have certain like agents. In some embodiments, a disclosed combination or method using, as examples, psilacetin, DMT, and lorazepam, or psilacetin, DMT, lorazepam, and ketamine, will show superiority to a combination of psilacetin and lorazepam, or for example psilocybin and lorazepam. For example, a disclosed combination or method using, as examples, psilacetin, DMT, and lorazepam, or psilacetin, DMT, lorazepam, and ketamine, may show persistent antidepressant effects that are greater than a treatment of only psilacetin and lorazepam, or psilocybin and lorazepam, such as greater efficacy, longevity, and/or durability.

In some embodiments, a disclosed method is useful for improving the health and/or wellbeing in an individual. In some embodiments, a disclosed method is useful for improving a subjective drug experience, or for purposes of improving a subjective drug experience. In some embodiments, a disclosed method is useful solely for improving a subjective drug experience, or solely for purposes of improving a subjective drug experience, without reference to an improvement in a disease state or in the overall health of an individual.

In some embodiments, measuring the efficacy of a disclosed method for improving the health and/or overall wellbeing of an individual will include an assessment. "Assessment" refers to any means or method used with an individual, whether before, during, after, or unrelated in time to a specific treatment protocol, to measure, estimate, or evaluate a nature, ability, symptom, disorder, or other characteristic of the individual, whether qualitatively or quantitatively, and whether performed by a facilitator (e.g., an interview), by the individual his or herself (e.g., a self-reported questionnaire), by a third-party or by a computer, including a device (e.g., a medical sensor or biosensor, a watch or fitness tracker, or a "wearable"), and whether graded by a human decision-maker or an artificial intelligence, machine learning, or computer algorithm.

In some embodiments, efficacy of a disclosed method for improving the health and/or overall wellbeing of an individual is assessed by self-rated measures. Self-rated measures include but are not limited to the Quick Inventory for Depressive Symptomatology (QIDS-SR16), the trait scale of the State-Trait Anxiety Inventory (STAI-T), the Neuroticism scale from the Neuroticism-Extraversion-Openness Five-Factor Inventory (NEO-FFI), the World Health Organization-Five Well-Being Index (WHO-5), the Life Orientation Test-Revised (LOT-R; a measure of optimism), the Gratitude Questionnaire (GQ-6), and/or the Meaning in Life Questionnaire (MLQ) (Timmermann et al. Sci Rep. 2024; 14(1):3097).

In some embodiments, a disclosed method is effective at improving the health and/or overall wellbeing of an individual because the subject has a complete mystical-type experience Mystical-type experiences are in some embodiments measured by the Mystical Experience Questionnaire (MEQ30) (Barrett et al. J. Psychopharm 2015; 29(11):1182-90) and can be defined for an individual rating their experience as >60% of the total maximum score among four dimensions of the questionnaire. Mystical-type experiences are correlated with symptom reduction amongst diverse pathologies (Ko et al. Front Psychiatry. 2022; 13: 917199). Beyond symptom reduction, mystical-type experiences are often considered to be highly personally and spiritually meaningful (Griffiths et al. J Psychopharmacol. 2008; 22(6): 621-32), and may be correlated with enduring positive changes in psychological functioning and in trait measures of prosocial attitudes and behaviors (Griffiths et al. J Psychopharmacol. 2018; 32(1):49-69), which indicates that they may contribute to improving general health and wellbeing.

In general, all of the disclosed methods will be appreciated to work for all individuals, although individual variation is to be expected, and will be readily appreciated. Where there is variation between individuals, modification to a disclosed method will be understood based on the teachings herein in combination with general knowledge in the art. In some embodiments, certain personalized approaches (i.e., "personalized" or "precision" medicine) may be utilized, based on individual characteristics, such as drug metabolism (e.g., genetic variation relating to CYP2D6 or CYP3A4 enzymes, or one or more other CYP enzymes) or susceptibility to treatment (e.g., the SIGMAR1 gene for the non-opioid sigma-1 receptor).

c. Synergistic Effects of Disclosed Methods and Combinations

In some embodiments, administration of DMT in combination with other agents according to disclosed methods provides synergistic effects. "Synergistic effects" refers to the effects of multiple (i.e., two or more) administered compounds that are greater than the additive contributions of the compounds acting alone, thereby producing "1+1>2" (likewise, "1+1+1>3" or "1+1+1+1>4"). "Greater" may refer to an amount that is an "increase" or a "reduction" depending on how the effect is described, and both may be an "improvement" (e.g., an "increase" in anxiolytic effects may be the same as a "reduction" in anxiety, and both may be the result of a synergy that produces "greater" than expected additive effects). Numerous methods will be known to those of skill to determine whether there are synergistic effects (equivalently, "synergy" or "synergism"). Suitable methods include isobologram (or contour) analysis (Huang et al. 2019, Front. Pharmacol. 10:1222), or the equation of Loewe additivity (Loewe & Muischnek, 1926, Arch. Exp. Pathol Pharmacol. 114: 313-326). A synergistic effect also may be calculated using methods such as the Sigmoid-Emax equation (Holford & Scheiner, 1981, Clin. Pharmacokinet. 6: 429-453) and the median-effect equation (Chou & Talalay, 1984, Adv. Enzyme Regul. 22:27-55). The corresponding graphs associated with the equations referred to above are the concentration-effect curve and combination index curve, respectively. Each equation referred to above may be applied to experimental data to generate a corresponding graph to aid in assessing the effects of the drug combination.

Non-limiting examples of synergistic effects of disclosed methods and combinations include increased and/or prolonged receptor (e.g., serotonin receptor) activation, enhanced pharmacological and/or therapeutic efficacy, reduced side effects, increased and/or modulated signaling pathway activation, effects resulting from the simultaneous activation of different receptor systems and/or subtypes, and effects resulting from a combination of such factors. In some embodiments, the synergistic effect is a pharmacokinetic effect. In some embodiments, the synergistic effect is a pharmacodynamic effect.

In some embodiments, a disclosed method has synergistic effects that result from increased receptor activation compared to when DMT is administered alone. In some embodiments, the simultaneous binding of DMT and another disclosed compound to the same receptor may potentiate the receptor for activation by a direct agonist. In other embodiments, the simultaneous binding of DMT and another disclosed compound to the same receptor may result in increased receptor occupancy. As an example, and without being bound by theory: Tropomyosin receptor kinase B (TrkB) is a receptor tyrosine kinase whose signaling has been implicated in the plasticity-promoting properties of psychedelics (Ly et al. Cell Rep. 2018; 23(11):3170-3182.). It was recently reported that DMT and other psychedelics do not bind TrkB directly (i.e., they typically do not function as TrkB agonists)—rather, they can act allosterically by facilitating the effects of endogenous BDNF released in active synapses, similar to classical antidepressants (Moliner et al. Nat Neurosci. 2023; 26:1032-1041). Ketamine, however, does directly bind to TrkB, and 2R,6R-hydroxynorketamine, an active metabolite of ketamine, binds to TrkB but shows low affinity to NMDA receptors (id.). Hence, the coadministration of DMT and a long-acting psychedelic (both of which may exert allosteric effects on TrkB), in some embodiments further in combination with ketamine, may result in synergistic effects that result from modulating TrkB signaling through multiple molecular mechanisms. In some embodiments, such synergistic mechanisms may enhance TrkB-mediated neuroplasticity and antidepressant effects, which may be useful for treating certain mental health disorders (e.g., depression), as well as improving the subjective DMT experience and general health and wellbeing of an individual subjected to a disclosed method.

In some embodiments, synergistic effects may result from convergent effects on cellular signaling through simultaneous activation of different receptor types and/or subtypes. As an example, the serotonin receptor profiles of psilocin (i.e., a primary psychoactive metabolite of psilocybin and psilacetin) and DMT were summarized in a 2011 report by Halberstadt A L & Geyer M A (Neuropharmacology. 2011; 61(3):364-381), which are reproduced below:

| Receptor | Psilocin Ki (nM) | DMT Ki (nM) |
|---|---|---|
| 5-HT$_{1A}$ | 567.4 | 183 |
| 5-HT$_{1B}$ | 219.6 | 129 |
| 5-HT$_{1D}$ | 36.4 | 39 |
| 5-HT$_{1E}$ | N.R.* | 517 |
| 5-HT$_{2A}$ | 107.2 | 127 |
| 5-HT$_{2B}$ | 4.6 | 184 |
| 5-HT$_{2C}$ | 97.3 | 360 |
| 5-HT$_{5A}$ | N.R.* | 2135 |
| 5-HT$_6$ | 57.0 | 464 |
| 5-HT$_7$ | 3.5 | 206 |

N.R. = not reported

Although the affinities of psilocin and DMT are similar for certain receptors, such as the 5-HT$_{2A}$ receptor, DMT is binds to other serotonin receptors with higher affinity than psilocin, such as the 5-HT$_{1A}$ and 5-HT$_{1B}$ receptors. Differences in receptor binding profile extend beyond serotonin receptors. For example, DMT binds to the sigma-1 receptor, for which psilocin reportedly has no affinity (Fontanilla et al. Science. 2009; 323(5916):934-937; Ray TS. PLoS One. 2010; 5(2):e9019).

Without being bound by theory in a discussion of the effects of activating any specific receptors, these data show that coadministration of DMT and a long-acting tryptamine (e.g., psilocin, psilocybin, psilacetin, or another compound of the disclosure) according to a disclosed method likely results in a pattern of receptor activation that is different from what is achieved by administering DMT or the long-acting tryptamine alone. This effect may result in amplification or interference of signaling pathways associated with these receptors. For example, 5-HT$_{2A}$ and 5-HT$_2$c receptor activation reportedly exerts opposing effects on locomotor activity in mice (Halberstadt et al. Neuropsychopharmacol. 2009; 34(8):1958-1967). As another example, activation of 5-HT$_{2A}$ and 5-HT$_2$c receptors counteracts the regulation of NMDA receptor channels by the 5-HT$_{1A}$ receptor in the prefrontal cortex (Yuen et al. J Biol Chem. 2008; 283(25): 17194-17204), which itself may be influenced by administration of a disclosed NMDA antagonist (e.g., ketamine). The results emphasize potential synergy between DMT, long-acting psychedelics, and other components of disclosed combinations and methods; by targeting multiple receptor systems and/or subtypes and consequent amplification or attenuation of associated signaling pathways, synergistic effects may be achieved that exceed those that would result from separate administration of the disclosed compounds.

Synergistic effects may also result from changes in drug metabolism, which can manifest through altered pharmacokinetics and/or altered elimination rates. For example, the DMT and the long-acting tryptamine may be metabolized at different rates, which can further alter the pattern of receptor engagement resulting from administration of a disclosed combination. In some embodiments, the DMT can alter the metabolism (e.g., elimination rate) of another component of a disclosed combination. In some embodiments, the long-acting tryptamine (or another component of a disclosed combination) can alter the elimination rate of the DMT. These effects may be further enhanced if a component of a disclosed combination interacts with (e.g., inhibits) an enzyme responsible for tryptamine metabolism (e.g., MAO). For example, if a component of a disclosed combination inhibits a MAO, the elimination rate of DMT may be decreased. In other embodiments, a component of a disclosed combination may not directly inhibit MAO, but may nonetheless decrease the elimination rate of DMT (or another component of a disclosed combination) by competing with DMT as a MAO substrate. Such factors, and others indicative of potentially synergistic drug-drug interactions, can be measured according to standard techniques, for instance HPLC analysis of metabolite profiles in serum, plasma, blood, or urine.

The foregoing examples are merely illustrative of potential mechanisms that may contribute to synergistic effects of disclosed methods and combinations. Experimentally investigating the effects of disclosed methods and combinations to assess the presence or absence of synergy is within the capabilities of one of skill in the art; an exemplary study model is also provided in Example 4.

F. EXAMPLES

The following examples are included for illustrative purposes only and are not intended to limit the scope of the invention.

Example 1: Exemplary Protocols for Improving the Experience of Inhaled DMT

Exemplary administration protocols are described below for improving the subjective experience of inhaled DMT.

Protocol 1—Co-administration of psilacetin and DMT: A 20-25 mg dose of psilacetin, or a pharmaceutically acceptable salt thereof, is orally administered to a human subject (t=0). Once the subjective peak of the long-acting tryptamine has elapsed, e.g., after about 90 minutes post-administration (t=1.5 hr) of the psilacetin, a 15-75 mg dose of DMT is vaporized and administered via inhalation. The dose of DMT is consumed in its entirety in one inhalation, or consumed in multiple smaller inhalations spread over a period of time, according to individual preferences.

The subjective effects of inhaled DMT last about 45 minutes to an hour. If subsequent administrations of DMT are desired, a minimum time interval of about 40 minutes from the end of the subjective effects of DMT to the subsequent administration is allowed to pass. Inhaled DMT can be administered throughout the duration of the psilacetin, such that the DMT is administered up to a total of about 4-5 times in this protocol.

Protocol 2—Co-administration of psilacetin and DMT with lorazepam: A 0.5-1 mg dose of lorazepam is orally administered to a human subject (t=0). About 45 minutes after administration of the benzodiazepine, 20-25 mg of psilacetin is orally administered to the subject. Once the subjective peak of the long-acting tryptamine has elapsed, e.g., after about 90 minutes post-administration (t=2.25 hr) of the psilacetin, a 15-75 mg dose of DMT is vaporized and administered via inhalation. The dose of DMT is consumed in its entirety in one inhalation, or consumed in multiple smaller inhalations spread over a period of time, according to individual preferences, and according to the disclosure.

The subjective effects of DMT last about 45 minutes to an hour. If subsequent administrations of DMT are desired, a minimum time interval of about 40 minutes from the end of the subjective effects of DMT to the subsequent administration is allowed to pass. Inhaled DMT can be administered throughout the duration of the psilacetin, such that the DMT is administered up to a total of about 4-5 times in this protocol.

Protocol 3—Co-administration of psilacetin and DMT with ketamine: A 20-25 mg of psilacetin is orally administered to a human subject (t=0). Once the subjective peak of the long-acting tryptamine has elapsed, e.g., after about 90 minutes post-administration (t=1.5 hr) of the psilacetin, a 15-75 mg dose of DMT is vaporized and administered via inhalation. The dose of DMT is consumed in its entirety in one inhalation, or consumed in multiple smaller inhalations spread over a period of time, according to individual preference. Ketamine is administered based on subjective preference to modulate the experience, e.g., at a dose of 20-30 mg by insufflation about once an hour throughout the duration of the effects of psilacetin, or as desired, and according to the disclosure.

The subjective effects of DMT last about 45 minutes to an hour. If subsequent administrations of DMT are desired, a minimum time interval of about 40 minutes from the end of the subjective effects of DMT to the subsequent administration is allowed to pass. Inhaled DMT can be administered throughout the duration of the psilacetin, such that the DMT is administered up to a total of about 4-5 times in this protocol.

Protocol 4—Co-administration of psilacetin and DMT with lorazepam and ketamine: A 0.5-1 mg dose of lorazepam (or in other embodiments, an equivalent dose of another benzodiazepine) is orally administered to a human subject (t=0). About 45 minutes after administration of the benzodiazepine, 20-25 mg of psilacetin is orally administered to the subject. Once the subjective peak of the long-acting tryptamine has elapsed, e.g., after about 90 minutes post-administration of the psilacetin (t=2.25 h), a 15-75 mg dose of DMT is vaporized and administered via inhalation. The dose of DMT is consumed in its entirety in one inhalation, or consumed in multiple smaller inhalations spread over a period of time, according to individual preferences, and according to the disclosure.

The subjective effects of DMT last about 45 minutes to an hour. If subsequent administrations of DMT are desired, a minimum time interval of about 40 minutes from the end of the subjective effects of DMT to the subsequent administration is allowed to pass. Inhaled DMT can be administered throughout the duration of the psilacetin, such that the DMT is administered up to a total of about 4-5 times in this protocol. Ketamine is administered based on subjective preference to modulate the experience, e.g., at a dose of 20-30 mg by insufflation about once an hour throughout the duration of the effects of psilacetin, or as desired and according to the disclosure.

The table below shows a timeline for the administration of compounds in some disclosed methods, according to certain exemplary and non-limiting protocols (I.N.=intranasal).

TABLE 1

Exemplary protocols for administration of DMT according to disclosed methods.

| Time | Exemplary Protocols | | | |
|---|---|---|---|---|
| | 1 | 2 | 3 | 4 |
| t = −0.75 h | | lorazepam (oral; 0.5-1 mg) | | lorazepam (oral; 0.5-1 mg) |
| t = 0 h | psilacetin (oral; 20-25 mg) | psilacetin (oral; 20-25 mg) | psilacetin (oral; 20-25 mg) | psilacetin (oral; 20-25 mg) |
| t = 1.25 h | | | | optionally: ketamine (I.N.; 15-25 mg) |
| t = 1.5 h | DMT (inhaled; 15-25 mg) | DMT (inhaled; 15-25 mg) | DMT (inhaled; 15-25 mg) | DMT (inhaled; 15-25 mg) |
| t = 3.0 h | optionally: DMT (inhaled; 15-25 mg) | optionally: DMT (inhaled; 15-25 mg) | optionally: ketamine (I.N.; 15-25 mg) | |
| t = 3.5 h | | | | optionally: ketamine (I.N.; 15-25 mg) |
| t = 3.75 h | optionally: DMT (inhaled; 15-25 mg) | | | optionally: DMT (inhaled; 15-25 mg) |
| t = 4.5 h | optionally: DMT (inhaled; 15-25 mg) | | optionally: ketamine (I.N.; 15-25 mg) | optionally: ketamine (I.N.; 15-25 mg) |

Additional exemplary protocols are provided below:

| Time | Exemplary Protocols | | | |
|---|---|---|---|---|
| | 5 | 6 | 7 | 8 |
| t = −1.00 h | prazepam (oral; 5-10 mg) | lorazepam (oral; 1-1.5 mg) | | lorazepam (oral; 0.5-1 mg) |
| t = 0 h | psilacetin (oral; 20-25 mg) | psilacetin (oral; 10-15 mg) & 4-HO-MET (oral; 10-15 mg) | psilacetin (oral; 10-15 mg) & 4-HO-MiPT (oral; 10-15 mg) | psilocybin (oral; 20-25 mg) |
| t = 1.25 h | optionally: ketamine (I.N.; 15-25 mg) | optionally: ketamine (I.N.; 15-25 mg) | optionally: ketamine (I.N.; 15-25 mg) | optionally: ketamine (I.N.; 15-25 mg) |
| t = 1.5 h | DMT (inhaled; 10-20 mg) | DMT (inhaled; 15-25 mg) | DMT (inhaled; 15-25 mg) | DMT (inhaled; 15-25 mg) |
| t = 2.75 h | | optionally: ketamine (I.N.; 15-25 mg) | optionally: ketamine (I.N.; 15-25 mg) | |
| t = 3.0 h | | optionally: DMT (inhaled; 15-25 mg) | optionally: DMT (inhaled; 15-25 mg) | optionally: ketamine (I.N.; 15-25 mg) |
| t = 3.5 h | optionally: DMT (inhaled; 15-25 mg) | optionally: ketamine (I.N.; 15-25 mg) | optionally: ketamine (I.N.; 15-25 mg) | |
| t = 4.75 h | optionally: DMT (inhaled; 5-10 mg) | optionally: ketamine (I.N.; 15-25 mg) | optionally: ketamine (I.N.; 15-25 mg) | optionally: ketamine (I.N.; 15-25 mg) |

The preceding protocols are illustrative in nature and should not be construed as limiting. Additional variations on the above described protocols will be understood, e.g., substituting comparable doses of another long-acting tryptamine for a specified long-acting tryptamine, substituting comparable doses of another short-acting tryptamine for DMT, substituting comparable doses of another NMDA antagonist or NMDA antagonist dissociative anesthetic for a specified NMDA antagonist, such as ketamine, substituting comparable doses of another benzodiazepine for a specified benzodiazepine, such as lorazepam, which will be understood by one of ordinary skill in the art. Additionally, various routes of administration may be used as substitutes for the above described.

Example 2: Assessing Improvements to the DMT Experience

A study was conducted to assess the effects of administering DMT according to a disclosed method. The study included nine participants with the following demographic characteristics:

| Participant No. | Gender | Age |
|---|---|---|
| 1 | Male | 48 |
| 2 | Female | 35 |
| 3 | Male | (not recorded) |
| 4 | Male | 41 |
| 5 | Male | mid 40s |
| 6 | Female | 40 |
| 7 | Male | 49 |
| 8 | Male | 47 |
| 9 | Female | 40 |

After inhaling DMT according to a disclosed method (e.g., a protocol described in Example 1), each subject was provided with a questionnaire that included questions from the Mystical Experience Questionnaire (MEQ30) and the Challenging Experience Questionnaire (CEQ). For the MEQ and CEQ higher scores indicate a more mystical experience and a more challenging experience, respectively.

Results

Table 2 summarizes participant responses for MEQ30 and CEQ dimensions evaluated in this study.

TABLE 2

Participant responses to post-DMT questionnaire

| Questionnaire Factor | Participant Score | | | | | | | | |
|---|---|---|---|---|---|---|---|---|---|
|  | 1 | 2 | 3 | 4 | 5 | 6 | 7 | 8 | 9 |
| 1.1 Freedom from the limitations of your personal self and feeling a unity or bond with what was felt to be greater than your personal self. | 2 | 3 | 4 | 2 | 4 | 5 | 4 | 5 | 5 |
| 1.2 Experience of pure being and pure awareness (beyond the world of sense impressions). | 2 | 5 | 4 | 2 | 4 | 5 | 4 | 4 | 5 |
| 1.3 Experience of oneness in relation to an "inner world" within. | 2 | 4 | 4 | 2 | 0 | 5 | 3 | 4 | 5 |
| 1.4 Experience of the fusion of your personal self into a larger whole. | 2 | 3 | 4 | 2 | 4 | 5 | 3 | 4 | 5 |
| 1.5 Experience of unity with ultimate reality. | 1 | 2 | 4 | 2 | 4 | 5 | 4 | 4 | 5 |
| 1.6 Feeling that you experienced eternity or infinity. | 0 | 2 | 4 | 1 | 0 | 5 | 2 | 3 | 5 |
| 1.7 Experience of oneness or unity with objects and/or persons perceived in your surroundings. | 1 | 3 | 4 | 4 | 4 | 5 | 2 | 4 | 3 |
| 1.8 Experience of the insight that "all is One". | 1 | 4 | 4 | 3 | 5 | 5 | 3 | 2 | 4 |
| 1.9 Awareness of the life or living presence in all things. | 1 | 5 | 4 | 4 | 5 | 5 | 4 | 3 | 4 |
| 1.10 Gain of insightful knowledge experienced at an intuitive level. | 2 | 4 | 4 | 4 | 5 | 5 | 5 | 4 | 5 |
| 1.11 Certainty of encounter with ultimate reality (in the sense of being able to "know" and "see" what is really real at some point during your experience. | 1 | 4 | 4 | 3 | 0 | 5 | 5 | 4 | 5 |
| 1.12 You are convinced now, as you look back on your experience, that in it you encountered ultimate reality (i.e., that you "knew" and "saw" what was really real). | 1 | 4 | 4 | 1 | 0 | 5 | 4 | 4 | 5 |
| 1.13 Sense of being at a spiritual height. | 1 | 3 | 4 | 2 | 5 | 5 | 5 | 5 | 5 |
| 1.14 Sense of reverence. | 2 | 4 | 4 | 2 | 5 | 5 | 5 | 5 | 5 |
| 1.15 Feeling that you experienced something profoundly sacred and holy. | 1 | 4 | 4 | 4 | 5 | 5 | 5 | 5 | 5 |
| 2.1 Experience of amazement. | 3 | 5 | 3 | 5 | 4 | 5 | 5 | 4 | 5 |
| 2.2 Feelings of tenderness and gentleness. | 2 | 4 | 3 | 4 | 2 | 5 | 3 | 1 | 5 |
| 2.3 Feelings of peace and tranquility. | 2 | 3 | 4 | 5 | 3 | 5 | 4 | 1 | 5 |
| 2.4 Experience of ecstasy. | 3 | 5 | 3 | 3 | 4 | 5 | 5 | 3 | 5 |
| 2.5 Sense of awe or awesomeness. | 3 | 5 | 4 | 5 | 4 | 5 | 5 | 4 | 5 |
| 2.6 Feelings of joy. | 3 | 4 | 4 | 4 | 4 | 4 | 5 | 3 | 5 |
| 3.1 Loss of your usual sense of time. | 2 | 3 | 4 | 5 | 3 | 5 | 4 | 4 | 5 |
| 3.2 Loss of your usual sense of space. | 2 | 4 | 4 | 5 | 5 | 5 | 4 | 4 | 5 |
| 3.3 Loss of usual awareness of where you were. | 0 | 2 | 3 | 3 | 3 | 5 | 4 | 4 | 5 |
| 3.4 Sense of being "outside of" time, beyond past and future. | 2 | 2 | 3 | 1 | 0 | 5 | 4 | 4 | 5 |
| 3.5 Being in a realm with no space boundaries. | 1 | 2 | 4 | 1 | 0 | 5 | 4 | 4 | 5 |
| 3.6 Experience of timelessness. | 2 | 3 | 3 | 2 | 0 | 5 | 3 | 4 | 5 |
| 4.1 Sense that the experience cannot be described adequately in words. | 2 | 3 | 4 | 5 | 4 | 5 | 5 | 4 | 5 |

TABLE 2-continued

Participant responses to post-DMT questionnaire

| Questionnaire Factor | Participant Score | | | | | | | | |
|---|---|---|---|---|---|---|---|---|---|
| | 1 | 2 | 3 | 4 | 5 | 6 | 7 | 8 | 9 |
| 4.2 Feeling that you could not do justice to your experience by describing it in words. | 4 | 3 | 4 | 5 | 4 | 5 | 5 | 4 | 5 |
| 4.3 Feeling that it would be difficult to communicate your own experience to others who have not had similar experiences. | 3 | 3 | 4 | 5 | 4 | 5 | 5 | 4 | 5 |
| 5.1 Isolation and loneliness. | 0 | 2 | 0 | 1 | 0 | 0 | 0 | 0 | 0 |
| 5.2 Sadness. | 1 | 2 | 1 | 1 | 0 | 4 | 0 | 0 | 0 |
| 5.3 Feeling my heart beating. | 0 | 1 | 1 | 1 | 0 | 0 | 1 | 0 | 0 |
| 5.4 I had the feeling something horrible would happen. | 1 | 0 | 0 | 1 | 0 | 0 | 0 | 1 | 0 |
| 5.5 Feeling my body shake/tremble. | 0 | 0 | 0 | 1 | 0 | 0 | 0 | 0 | 0 |
| 5.6 Feelings of grief. | 0 | 1 | 0 | 1 | 0 | 4 | 0 | 0 | 0 |
| 5.7 Experience of fear. | 1 | 2 | 0 | 1 | 0 | 0 | 0 | 1 | 0 |
| 5.8 Fear that I might lose my mind or go insane. | 1 | 0 | 0 | 1 | 0 | 0 | 0 | 2 | 0 |
| 5.9 I felt like crying. | 0 | 0 | 0 | 1 | 0 | 4 | 0 | 0 | 0 |
| 5.10 Feeling of isolation from people and things. | 0 | 1 | 0 | 1 | 0 | 0 | 0 | 0 | 0 |
| 5.11 Feelings of despair. | 0 | 1 | 0 | 1 | 0 | 0 | 0 | 0 | 0 |
| 5.12 I had the feeling that people were plotting against me. | 0 | 1 | 0 | 1 | 0 | 0 | 0 | 0 | 0 |
| 5.13 I was afraid that the state I was in would last forever. | 0 | 0 | 0 | 1 | 0 | 0 | 0 | 0 | 0 |
| 5.14 Anxiousness. | 1 | 2 | 0 | 1 | 0 | 0 | 0 | 0 | 0 |
| 5.15 I felt shaky inside. | 0 | 0 | 0 | 1 | 0 | 0 | 0 | 0 | 0 |
| 5.16 I had the profound experience of my own death. | 0 | 0 | 1 | 1 | 0 | 0 | 0 | 0 | 0 |
| 5.17 I felt my heart beating irregularly or skipping beats. | 0 | 0 | 0 | 1 | 0 | 0 | 0 | 0 | 0 |
| 5.18 Pressure or weight in my chest or abdomen. | 0 | 0 | 0 | 1 | 0 | 0 | 0 | 0 | 0 |
| 5.19 I experienced a decreased sense of sanity. | 1 | 1 | 0 | 1 | 0 | 0 | 0 | 0 | 0 |
| 5.20 I felt as if I was dead or dying. | 0 | 1 | 0 | 1 | 0 | 0 | 0 | 0 | 0 |
| 5.21 Panic. | 0 | 0 | 0 | 1 | 0 | 0 | 0 | 0 | 0 |
| 5.22 Experience of antagonism toward people around me. | 0 | 1 | 0 | 1 | 0 | 0 | 0 | 0 | 0 |
| 5.23 Despair. | 0 | 1 | 0 | 1 | 0 | 0 | 0 | 0 | 0 |
| 5.24 I felt isolated from everything and everyone. | 0 | 1 | 0 | 1 | 0 | 0 | 0 | 0 | 0 |
| 5.25 Emotional and/or physical suffering. | 2 | 1 | 0 | 1 | 0 | 0 | 0 | 0 | 0 |
| 5.26 I felt frightened. | 2 | 1 | 0 | 1 | 0 | 0 | 0 | 0 | 0 |

Table 3 shows each participant's total score for the four MEQ30 subscales.

TABLE 3

Total scores for each participant for the Mysticism, Positive Mood, Transcendence, and Ineffability subscales of the MEQ30.

| Participant No. | Mysticism | Positive Mood | Transcendence | Ineffability |
|---|---|---|---|---|
| 1 | 20 | 16 | 9 | 9 |
| 2 | 54 | 26 | 16 | 9 |
| 3 | 60 | 21 | 21 | 12 |
| 4 | 38 | 26 | 17 | 15 |
| 5 | 50 | 21 | 11 | 12 |
| 6 | 75 | 29 | 30 | 15 |
| 7 | 58 | 27 | 23 | 15 |
| 8 | 60 | 16 | 24 | 12 |
| 9 | 71 | 30 | 30 | 15 |

Tables 4 and 5 show participant scores for MEQ30 and CEQ dimensions determined from the data shown in Table 3.

TABLE 4

Mean participant scores for the Mysticism, Positive Mood, Transcendence, and Ineffability dimensions of the MEQ30.

| Participant No. | Mysticism | Positive Mood | Transcendence | Ineffability |
|---|---|---|---|---|
| 1 | 1.33 | 2.67 | 1.50 | 3.00 |
| 2 | 3.60 | 4.33 | 2.67 | 3.00 |
| 3 | 4.00 | 3.50 | 3.50 | 4.00 |
| 4 | 2.53 | 4.33 | 2.83 | 5.00 |
| 5 | 3.33 | 3.50 | 1.83 | 4.00 |
| 6 | 5.00 | 4.83 | 5.00 | 5.00 |
| 7 | 3.87 | 4.50 | 3.83 | 5.00 |
| 8 | 4.00 | 2.67 | 4.00 | 4.00 |
| 9 | 4.73 | 5.00 | 5.00 | 5.00 |
| Mean | 3.60 | 3.93 | 3.35 | 4.22 |

TABLE 5

Individual participant scores and mean values for dimensions of the CEQ.

| Participant No. | Fear | Grief | Physical Distress | Insanity | Isolation | Death | Paranoia |
|---|---|---|---|---|---|---|---|
| 1 | 5 | 3 | 0 | 2 | 0 | 0 | 0 |
| 2 | 5 | 6 | 1 | 1 | 4 | 1 | 2 |
| 3 | 0 | 1 | 1 | 0 | 0 | 1 | 0 |
| 4 | 5 | 6 | 5 | 3 | 3 | 2 | 2 |
| 5 | 0 | 0 | 0 | 0 | 0 | 0 | 0 |

TABLE 5-continued

Individual participant scores and mean values for dimensions of the CEQ.

| Participant No. | Fear | Grief | Physical Distress | Insanity | Isolation | Death | Paranoia |
|---|---|---|---|---|---|---|---|
| 6 | 0 | 12 | 0 | 0 | 0 | 0 | 0 |
| 7 | 0 | 0 | 1 | 0 | 0 | 0 | 0 |
| 8 | 2 | 0 | 0 | 2 | 0 | 0 | 0 |
| 9 | 0 | 0 | 0 | 0 | 0 | 0 | 0 |
| Mean | 1.889 | 3.11 | 0.89 | 0.89 | 0.78 | 0.44 | 0.44 |

Conclusions

Results demonstrate that all participants had a score of greater than or equal to 60% on at least one of the Mystical, Positive Mood, Transcendence of Time and Space, and Ineffability MEQ30 subscales. 78% of participants had a score of greater than or equal to 60% of the maximum score on the Mystical and Positive Mood subscales, and 55% of the participants had a score of greater than or equal to 75% of the maximum scores. 55% of participants had a score of greater than or equal to 60% of the maximum score on the Transcendence of Time and Space subscale, and 44% of participants had a score of greater than or equal to 75% of the maximum score. 100% of participants had a score of greater than or equal to 60% of the maximum score on the Ineffability subscale, and 78% of participants had a score of greater than or equal to 75% of the maximum score. Furthermore, 4400 of participants had a "mystical-type experience" as defined by a score of >60% of the maximum score for all four MEQ30 subscales.

There were few challenging experiences. On each of the CEQ subscales, the mean participant score did not exceed 10% of the maximum possible score. For the Fear, Physical Distress, Insanity, Isolation, Death, and Paranoia subscales, the mean participant score was less than about 6% of the maximum score.

Example 3: Additional Study to Assess Improvements to the DMT Experience

A study is conducted to compare the effects of inhaled DMT alone with the effects of a inhaled DMT according to a disclosed method. The doses of DMT used in each study are equivalent for the purposes of comparison. After inhaling DMT, subjects are administered any of the Mystical Experience Questionnaire (MEQ30), the Challenging Experience Questionnaire (CEQ), or the Hallucinogen Rating Scale (HRS), or like questionnaires known to those in the art, such as the Mysticism Scale (M-scale) or Hood Mysticism Scale (HMS), the Five Dimensional or 11 Dimensional Altered States of Consciousness Questionnaire (5D-ASC or 11D-ASC), the States of Consciousness Questionnaire (SOCQ), the Ego Dissolution Inventory (EDI), and the Phenomenology of Consciousness Inventory (PCI). Additional measures may be used to assess the qualities of each subjective experience, as would be understood and available to one of skill in the art. Regarding MEQ, CEQ, and the HRS, higher scores indicate a more mystical experience, a more challenging experience, and a more intense psychedelic experience, respectively. Preferably, subjects who have participated in a modulated DMT experience will experience reduced anxiety, reduced intensity, e.g., a more navigable and controlled experience, and enhanced desirable and pleasurable effects.

Subjects may also further evaluate the impact of a modulated DMT experience using the Persisting Effects Questionnaire (PEQ), Satisfaction with Life Scale (SWL), State-Trait Anxiety Inventory, WHO Quality of Life Assessment Instrument, and Positive and Negative Affect Schedule (PANAS) by comparing results of such assessments prior to and after ingestion of DMT and prior to and after co-administration of DMT, a long-acting tryptamine, and optionally a benzodiazepine (e.g., lorazepam) and/or an NMDA antagonist (e.g., ketamine), as described herein. Subjects who have engaged in a modulated DMT experience are expected to express having positive persisting psychological changes, e.g., improvements in attitudes about life, attitudes about self, mood changes, social effects, behavioral changes, and spirituality, greater satisfaction with life, reduced anxiety, and enhanced positive affect.

Example 4: Assessing Synergistic Effects of Disclosed Combinations and Methods

Synergistic effects of disclosed combinations and methods are assessed in a clinical study in which DMT, a long-acting psychedelic, a benzodiazepine, and ketamine are administered to different participant groups in the following combinations:

|  | Group 1 | Group 2 | Group 3 | Group 4 | Group 5 |
|---|---|---|---|---|---|
| Drug(s) | DMT | DMT Long-acting tryptamine | DMT Long-acting tryptamine Benzodiazepine | DMT Long-acting tryptamine Ketamine | DMT Long-acting tryptamine Benzodiazepine Ketamine |

The doses of DMT used in each study are equivalent for the purposes of comparison. After inhaling DMT, synergistic effects of disclosed combinations are assessed by administered a questionnaire to participants in each group, such as the Mystical Experience Questionnaire (MEQ30), the Challenging Experience Questionnaire (CEQ), or the Hallucinogen Rating Scale (HRS), the Mysticism Scale (M-scale) or Hood Mysticism Scale (HMS), the Five Dimensional or 11-Dimensional Altered States of Consciousness Questionnaire (5D-ASC or 11D-ASC), the States of Consciousness Questionnaire (SOCQ), the Ego Dissolution Inventory (EDI), or the Phenomenology of Consciousness Inventory (PCI).

Assessing synergistic effects can also include obtaining objective health measurements from the patient, (herein, "objective measurements,") including but not limited to weight, body temperature, heart rate (HR), respiratory rate, blood oxygenation, blood pressure (BP) and its variables, including, but not limited to: systolic (SBP), diastolic (DBP), mean arterial (MAP), and pulse (PP); continuous non-invasive beat-by-beat blood pressure (CNIBP); measurements from an electrocardiogram (ECG), including RR interval or its variability, QT interval or its variability, heart rate variability (HRV) (or measured by devices other than an ECG); hemodynamic response (HR), and levels of glucose, cortisol, serotonin, dopamine, cholesterol; electroencephalography (EEG) measures such as quantitative EEG (qEEG); electrocochleogram (ECochG), electromyography (EMG), electrooculography (EOG), magnetoencephalography (MEG); electrocorticography (ECoG); magnetic resonance imaging (MRI); functional MRI (fMRI); computed tomography (CT); positron emission tomography (PET); nuclear magnetic resonance (NMR) spectroscopy or magnetic resonance spectroscopy (MSR); single-photon emission computed tomography (SPECT); near infrared spectroscopy (NIRS); event-related optical signal (EROS); computed axial tomography; diffuse optical imaging (DOI); cranial ultrasound; or functional ultrasound imaging (fUS) (together, "EEG measures").

Synergistic effects may also result from changes in drug metabolism, which can manifest through altered pharmacokinetics and altered elimination rates. Such factors, and others indicative of potentially synergistic drug-drug interactions, can be measured according to standard techniques, for instance HPLC analysis of metabolite profiles in serum, plasma, blood, or urine.

Results may show that administering DMT according to a disclosed method (e.g., in combination with a long-acting tryptamine, and optionally further in combination with a benzodiazepine, ketamine, and any additional active agents) results in synergistic effects. Such synergistic effects may improve the subjective DMT experience, as well as manifest as advantageous pharmacokinetic and/or pharmacodynamic properties, as described in embodiments herein.

Example 5: Natural Language Processing to Assess Improvements to the DMT Experience A study is conducted to compare the experience of inhaled DMT alone with the effects of a inhaled DMT according to a disclosed method. Subjects will be divided into four treatment groups; (1) DMT administered alone, (2) DMT administered with a long-acting psychedelic, (3) DMT administered with a long-acting psychedelic and a benzodiazepine, and (4) DMT administered with a long-acting psychedelic, a benzodiazepine, and an NMDAR antagonist. The dosage of each compound and timing at which they are administered relative to one another will be equivalent for purposes of comparison. The data collected from this study to draw comparisons between the treatment groups will consist of the spoken and written language produced by the subjects during and after their treatment.

During their treatment, subjects will be asked a series of questions designed to prompt the subject to describe their subjective experience, including but not limited to their mood, level of anxiety, level of fear, phenomenology of their experience, visual sensations, auditory sensations, tactile sensations, etc. On the day after their treatment, subjects will be asked to write about their experience in the form of an experience report. Experience reports will include a subjective narrative of their experience.

The spoken and written language from each participant will be analyzed by natural language processing (NLP). Specifically, semantic analyses will be performed to infer the meaning intended by the subject. Semantic analyses consist of grouping words into categories and assessing their co-occurrence with other words or categories. This technique effectively transforms language into psychologically meaningful variables which can be compared across treatment groups. The semantic analysis performed here will be designed to analyze subjects' language for the prevalence of word categories representing certain emotional states and cognitive function, and compare the results between treatment groups. For example, the analysis will compare affective words reflecting emotional states such as positive emotion, negative emotion, anxiety, and sadness between treatment groups. It will also examine words reflective of cognitive processes, creative thinking and analytical thinking between groups. Additionally, it will assess semantic similarity of subjects' language to established scales capturing psychedelic or mystical experiences (Hood. J Sci Study Relig. 1975; 14:29-41; Studerus et al. PLoS One. 2010; 5(8):e12412).

Subjects who have been administered DMT according to a disclosed method are expected to have expressed language that reflects more positive emotion, and less negative emotion, anxiety, and sadness than in subjects who engaged in the DMT-only treatment group. Further, subjects who have been administered DMT according to a disclosed method may express language reflecting improved cognitive, creative, and analytical thinking abilities than subjects in the DMT-only group. Subjects who have been administered DMT according to a disclosed method may also be expected to express language corresponding to an improved DMT experience, which can be measured, for instance, by a higher scores on established scales of psychedelic or mystical experiences (e.g., the MEQ30), and/or lower scores on scales that assess negative experiences (e.g., the CEQ) than subjects in the DMT-only treatment group, as described in embodiments herein.

G. EXEMPLARY ASPECTS AND EMBODIMENTS

Among the various aspects and embodiments of the disclosure are the following, which will be understood to be exemplary and not limiting.

In one exemplary aspect, provided is a method of improving the DMT experience, comprising administering to an individual an effective amount of: (i) a long-acting tryptamine, or a pharmaceutically acceptable salt thereof; (ii) DMT, or a pharmaceutically acceptable salt thereof; (iii) optionally, a benzodiazepine, or a pharmaceutically acceptable salt thereof; and (iv) optionally, ketamine, or a pharmaceutically acceptable salt thereof; wherein administering the long-acting tryptamine is prior to administering the DMT.

In some embodiments, the DMT is freebase DMT. In some embodiments, the DMT is a pharmaceutically acceptable salt of DMT. In some embodiments, the DMT is DMT fumarate.

In some embodiments the long-acting tryptamine has the structure of Formula (1):

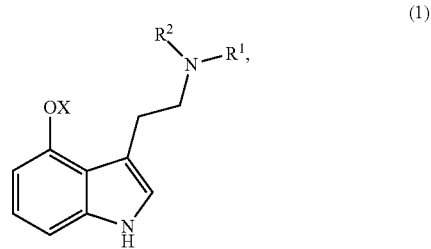

or a pharmaceutically acceptable salt thereof, wherein $R^1$ and $R^2$ are each independently H or alkyl; and X is H, —$PO_3H_2$, or —C(O)-alkyl.

In some embodiments, the long-acting tryptamine is selected from the group consisting of:
4-hydroxy-N,N-dimethyltryptamine (psilocin),
4-phosphoryloxy-N,N-dimethyltryptamine (psilocybin),
4-acetoxy-N,N-dimethyltryptamine (psilacetin),
4-hydroxy-N,N-diethyltryptamine (4-HO-DET),
4-phosphoryloxy-N,N-diethyltryptamine (4-OPO$_3$H$_2$-DET),
4-acetoxy-N,N-diethyltryptamine (4-AcO-DET),
4-hydroxy-N,N-diisopropyltryptamine (4-HO-DiPT),
4-phosphoryloxy-N,N-diisopropyltryptamine (4-OPO$_3$H$_2$-DiPT),
4-acetoxy-N,N-diisopropyltryptamine (4-AcO-DiPT),
4-hydroxy-N,N-dipropyltryptamine (4-HO-DPT),
4-phosphoryloxy-N,N-dipropyltryptamine (4-OPO$_3$H$_2$-DPT),
4-acetoxy-N,N-dipropyltryptamine (4-AcO-DPT),
4-hydroxy-N,N-dibutyltryptamine (4-HO-DBT),
4-phosphoryloxy-N,N-dibutyltryptamine (4-OPO$_3$H$_2$-DBT),
4-acetoxy-N,N-dibutyltryptamine (4-AcO-DBT),
4-hydroxy-N-methyl-N-ethyltryptamine (4-HO-MET),
4-phosphoryloxy-N-methyl-N-ethyltryptamine (4-OPO$_3$H$_2$-MET),
4-acetoxy-N-methyl-N-ethyltryptamine (4-AcO-MET),
4-hydroxy-N-methyl-N-isopropyltryptamine (4-HO-MiPT),
4-phosphoryloxy-N-methyl-N-isopropyltryptamine (4-OPO$_3$H$_2$-MiPT),
4-acetoxy-N-methyl-N-isopropyltryptamine (4-AcO-MiPT),
4-hydroxy-N-methyl-N-propyltryptamine (4-HO-MPT), and
4-phosphoryloxy-N-methyl-N-propyltryptamine (4-OPO$_3$H$_2$-MPT);
and pharmaceutically acceptable salts thereof.

In some embodiments, the long-acting tryptamine is psilacetin, psilocybin, or psilocin, or a pharmaceutically acceptable salt thereof.

In some embodiments, the long-acting tryptamine is psilacetin, or a pharmaceutically acceptable salt thereof.

In some embodiments, the optional benzodiazepine is administered to the subject. In some embodiments, the benzodiazepine is selected from the group consisting of alprazolam, bromazepam, chlordiazepoxide, clobazam, clonazepam, clorazepate, diazepam, estazolam, etizolam, flunitrazepam, flurazepam, flutoprazepam, halazepam, ketazolam, loprazolam, lorazepam, lormetazepam, midazolam, nimetazepam, nitrazepam, oxazepam, prazepam, quazepam, temazepam, tetrazepam, and triazolam; or a pharmaceutically acceptable salt thereof.

In some embodiments, the benzodiazepine is lorazepam, or a pharmaceutically acceptable salt thereof.

In some embodiments, the benzodiazepine is administered prior to the long-acting tryptamine. In some embodiments, the benzodiazepine is administered prior to the DMT.

In some embodiments, the optional ketamine is administered to the subject.

In some embodiments, the long-acting tryptamine, or a pharmaceutically acceptable salt thereof, is administered at a dose of about 5 to 50 mg, 10 to 40 mg, 15 to 30 mg, 20 to 25 mg.

In some embodiments, the long-acting tryptamine, or a pharmaceutically acceptable salt thereof, is administered at a dose of about 0.1 to 1.0 mg/kg, 0.2 to 0.7 mg/kg, 0.2 to 0.5 mg/kg, or 0.3 to 0.4 mg/kg.

In some embodiments, the DMT, or a pharmaceutically acceptable salt thereof, is administered at a dose of about 5 to 50 mg, 10 to 40 mg, 15 to 30 mg, 20 to 25 mg.

In some embodiments, the DMT, or a pharmaceutically acceptable salt thereof, is administered at a dose of about 0.1 to 1.0 mg/kg, 0.2 to 0.7 mg/kg, 0.2 to 0.5 mg/kg, or 0.3 to 0.4 mg/kg.

In some embodiments, the benzodiazepine, or a pharmaceutically acceptable salt thereof, is administered at a dose of about 0.5 to 2 mg, about 0.5 to 1.5 mg, about 0.5 to 1 mg, about 0.5 mg, about 1.0 mg, about 1.5 mg, or about 2.0 mg.

In some embodiments, the ketamine, or a pharmaceutically acceptable salt thereof, is administered at a dose of about 10 to 50 mg, 10 to 30 mg, 10 to 20 mg, 15 to 30 mg, 15 to 20 mg, or 20 to 30 mg.

In some embodiments, the ketamine, or a pharmaceutically acceptable salt thereof, is administered at a dose of about 0.1 to 2.0 mg/kg, 0.15 to 1.5 mg/kg, 0.15 to 1.0 mg/kg, 0.15 to 0.5 mg/kg, 0.15 to 0.4 mg/kg, 0.2 to 1.5 mg/kg, 0.2 to 1.0 mg/kg, 0.2 to 0.5 mg/kg, or 0.2 to 0.4 mg/kg.

In some embodiments, the long-acting tryptamine, or a pharmaceutically acceptable salt thereof, is administered orally.

In some embodiments, the benzodiazepine, or a pharmaceutically acceptable salt thereof, is administered orally.

In some embodiments, the DMT, or a pharmaceutically acceptable salt thereof, is administered intravenously, intramuscularly, or by inhalation. In some embodiments, the DMT, or a pharmaceutically acceptable salt thereof, is administered by inhalation.

In some embodiments, the ketamine, or a pharmaceutically acceptable salt thereof, is administered intranasally.

In some embodiments, the method comprises administering to the subject a therapeutically effective amount of: (i) psilacetin, psilocin, or psilocybin, or a pharmaceutically acceptable salt thereof; and (ii) DMT, or a pharmaceutically acceptable salt thereof; wherein the psilacetin, psilocin, or psilocybin is administered prior to the DMT.

In some embodiments, the method comprises administering to the subject a therapeutically effective amount of: (i) psilacetin, or a pharmaceutically acceptable salt thereof; (ii) DMT, or a pharmaceutically acceptable salt thereof; and (iii) lorazepam, or a pharmaceutically acceptable salt thereof; wherein the psilacetin is administered prior to the DMT.

In some embodiments, the method comprises administering to the subject a therapeutically effective amount of: (i) psilacetin, or a pharmaceutically acceptable salt thereof; (ii) DMT, or a pharmaceutically acceptable salt thereof; and (iii) ketamine, or a pharmaceutically acceptable salt thereof; wherein the psilacetin is administered prior to the DMT.

In some embodiments, the method comprises administering to the subject a therapeutically effective amount of: (i) psilacetin, or a pharmaceutically acceptable salt thereof; (ii) DMT, or a pharmaceutically acceptable salt thereof; (iii) lorazepam, or a pharmaceutically acceptable salt thereof; and (iv) ketamine, or a pharmaceutically acceptable salt thereof; wherein the psilacetin is administered prior to the DMT.

The foregoing description, for purposes of explanation, uses specific nomenclature to provide a thorough understanding of the invention. However, it will be apparent to one in the art that specific details are not required in order to practice the invention. Thus, the foregoing description of specific embodiments of the invention is presented for purposes of illustration and description. It is not intended to be exhaustive or to limit the invention to the precise compositions, formulations, methods, or the like disclosed; many modifications and variations are possible in view of the above teachings. The embodiments were chosen and described in order to best explain the principles of the invention and its practical applications, through the elucidation of specific examples, and to thereby enable others skilled in the art to best utilize the invention and various embodiments with various modifications as are suited to the particular use contemplated, when such uses are beyond the specific examples disclosed.

Accordingly, the scope of the invention shall be defined solely by the following claims and their equivalents.

The invention claimed is:

1. A method of providing an improved subjective experience of DMT to an individual, comprising administering to the individual:
   i. psilacetin, or a pharmaceutically acceptable salt thereof; and
   ii. DMT, or a pharmaceutically acceptable salt thereof; wherein:
   iii. administering the psilacetin is at least about 90 minutes prior to administering the DMT;
   iv. the DMT is administered by inhalation; and
   V. the DMT is administered from 1 to 5 times during the 5 hours following the peak of the psychedelic effects of the psilacetin; and
   wherein the method results in, compared to administering an equal amount of DMT alone, any of:
   a. a reduction in the intensity of the subjective experience of DMT;
   b. a reduction in a physical or psychological side effect of DMT;
   c. an increase in the individual's ability to keep their eyes open; and
   d. an increase in the individual's sense of control.

2. The method of claim 1, wherein the psilacetin is administered at a dose of from about 5 to 50 mg, about 10 to 40 mg, about 15 to 30 mg, or about 20 to 25 mg.

3. The method of claim 1, wherein the DMT is administered about 90 minutes after the administration of the psilacetin.

4. The method of claim 1, wherein the DMT is administered 2 times during the 2 hours, 3 times during the 3 hours, or 4 times during the 4 hours following the peak of the psychedelic effects of the psilacetin.

5. The method of claim 4, wherein each dose of DMT is from about 5 to 50 mg, about 10 to 30 mg, or about 15 to 25 mg.

6. The method of claim 1, further comprising administering to the individual a benzodiazepine, or a pharmaceutically acceptable salt thereof.

7. The method claim 6, wherein the benzodiazepine is any of alprazolam, bromazepam, chlordiazepoxide, clobazam, clonazepam, clorazepate, diazepam, estazolam, etizolam, flunitrazepam, flurazepam, flutoprazepam, halazepam, ketazolam, loprazolam, lorazepam, lormetazepam, midazolam, nimetazepam, nitrazepam, oxazepam, prazepam, quazepam, temazepam, tetrazepam, and triazolam.

8. The method of claim 7, wherein the benzodiazepine is lorazepam.

9. The method of claim 8, wherein the lorazepam is administered at a dose of from about 0.5 to 2 mg.

10. The method of claim 6, wherein the benzodiazepine is administered prior to the psilacetin.

11. The method of claim 1, further comprising administering to the individual ketamine, or a pharmaceutically acceptable salt thereof.

12. The method of claim 11, wherein the ketamine is administered from 1 to 5 times during the 5 hours following administering to the individual the psilacetin.

13. The method of claim 12, wherein each dose of ketamine is from about 5 to 50 mg, about 10 to 30 mg, or about 15 to 25 mg.

14. The method of claim 11, wherein the ketamine is administered intranasally.

15. The method of claim 1, further comprising administering to the individual a long-acting psychedelic, or a pharmaceutically acceptable salt thereof.

16. The method of claim 15, wherein the long-acting psychedelic is 4-hydroxy-N-methyl-N-ethyltryptamine (4-HO-MET) or 4-hydroxy-N-methyl-N-isopropyltryptamine (4-HO-MiPT).

17. The method of claim 1, wherein the reduction in a physical or psychological side effect of DMT is determined by individual reporting or data monitoring, and comprises a reduction in any of disorientation, acute anxiety, emotional distress, diarrhea, nausea, vomiting, elevated heart rate, elevated blood pressure, dizziness, agitation, and muscle incoordination, compared to administering an equal amount of DMT alone to the individual.

18. The method of claim 1, further comprising an increase in a positive effect of DMT, wherein the increase in a positive effect of DMT is determined by individual reporting or data monitoring, and comprises an increase in any of feelings of euphoria, positive mood, internal unity, external unity, transcendence of time and space, ineffability, paradoxicality, sacredness, and noetic quality, compared to administering an equal amount of DMT alone to the individual.

19. The method of claim 1, further comprising an increase in a positive effect of DMT, wherein the increase in a positive effect of DMT is determined by individual reporting or data monitoring, and comprises an increase in the score of any of the Mystical, Positive Mood, Transcendence of Time and Space, and Ineffability subscales of the 30-item revised Mystical Experience Questionnaire (MEQ30), compared to administering an equal amount of DMT alone to the individual.

20. The method of claim 1, wherein the reduction in a physical or psychological side effect of DMT is determined by individual reporting or data monitoring, and comprises a reduction in the score of any of the Fear, Grief, Physical Distress, Insanity, Isolation, Death, and Paranoia subscales of the Challenging Experience Questionnaire (CEQ), compared to administering an equal amount of DMT alone to the individual.

21. A method of providing an improved subjective experience of DMT to an individual, comprising administering to the individual:
   i. psilacetin, or a pharmaceutically acceptable salt thereof;
   ii. DMT, or a pharmaceutically acceptable salt thereof;
   iii. lorazepam, or a pharmaceutically acceptable salt thereof; and
   iv. ketamine, or a pharmaceutically acceptable salt thereof;
   wherein:
   iii. administering the psilacetin is at least about 90 minutes prior to administering the DMT;
   iv. the DMT is administered by inhalation; and v. the DMT is administered from 1 to 5 times during the 5 hours following the peak of the psychedelic effects of the psilacetin; and wherein the method results in, compared to administering an equal amount of DMT alone, any of:
a. a reduction in the intensity of the subjective experience of DMT;
b. a reduction in a physical or psychological side effect of DMT;
c. an increase in the individual's ability to keep their eyes open; and
d. an increase in the individual's sense of control.

22. The method of claim 1, wherein the reduction in the intensity of the subjective experience of DMT is determined by individual reporting or data monitoring, and comprises a more navigable and controlled experience, compared to administering an equal amount of DMT alone to the individual.

23. The method of claim 1, wherein the increase in the individual's ability to keep their eyes open is determined by individual reporting or data monitoring, compared to administering an equal amount of DMT alone to the individual.

24. The method of claim 1, wherein the increase in the individual's sense of control is determined by individual reporting or data monitoring, compared to administering an equal amount of DMT alone to the individual.

25. The method of claim 1, wherein the method results in, compared to administering an equal amount of DMT alone, a reduction in the intensity of the subjective experience of DMT and a reduction in a physical or psychological side effect of DMT.

26. The method of claim 1, wherein the method results in, compared to administering an equal amount of DMT alone, an increase in the individual's ability to keep their eyes open and an increase in the individual's sense of control.

27. The method of claim 1, wherein the method results in, compared to administering an equal amount of DMT alone, a reduction in the intensity of the subjective experience of DMT, a reduction in a physical or psychological side effect of DMT, an increase in the individual's ability to keep their eyes open, and an increase in the individual's sense of control.

28. The method of claim 1, further comprising determining, by individual reporting or data monitoring, the reduction in the intensity of the subjective experience of DMT, the reduction in a physical or psychological side effect of DMT, the increase in the individual's ability to keep their eyes open, or the increase in the individual's sense of control, compared to administering an equal amount of DMT alone to the individual.

* * * * *